(12) United States Patent
Jones et al.

(10) Patent No.: US 10,980,491 B1
(45) Date of Patent: Apr. 20, 2021

(54) TREND ANALYSIS FOR HYDRATION MONITORING

(71) Applicant: Halo Wearables, LLC, Morgan, UT (US)

(72) Inventors: Michael Jones, Morgan, UT (US); Devin Miller, Morgan, UT (US); David Miller, Morgan, UT (US)

(73) Assignee: Halo Wearables, LLC, Morgan, UT (US)

( * ) Notice: Subject to any disclaimer, the term of this patent is extended or adjusted under 35 U.S.C. 154(b) by 318 days.

(21) Appl. No.: 15/295,598

(22) Filed: Oct. 17, 2016

Related U.S. Application Data

(60) Provisional application No. 62/242,923, filed on Oct. 16, 2015.

(51) Int. Cl.
*A61B 5/00* (2006.01)
*A61B 5/0205* (2006.01)
(Continued)

(52) U.S. Cl.
CPC .......... *A61B 5/7275* (2013.01); *A61B 5/0022* (2013.01); *A61B 5/0024* (2013.01); *A61B 5/02055* (2013.01); *A61B 5/0535* (2013.01); *A61B 5/067* (2013.01); *A61B 5/068* (2013.01); *A61B 5/1112* (2013.01); *A61B 5/14551* (2013.01); *A61B 5/4875* (2013.01); *A61B 5/681* (2013.01); *A61B 5/6824* (2013.01); *G16H 15/00* (2018.01); *A61B 5/021* (2013.01); *A61B 5/024* (2013.01); *A61B 5/0245* (2013.01); *A61B 5/0816* (2013.01)

(58) Field of Classification Search
CPC .... G16H 15/00; A61B 5/7275; A61B 5/0022; A61B 5/0024; A61B 5/02055; A61B 5/0535; A61B 5/067; A61B 5/068; A61B 5/1112; A61B 5/14551; A61B 5/4875; A61B 5/681; A61B 5/6824; A61B 5/021; A61B 5/024; A61B 5/0245; A61B 5/0816
See application file for complete search history.

(56) References Cited

U.S. PATENT DOCUMENTS

2011/0245633 A1* 10/2011 Goldberg ............... A61B 5/681
600/301
2011/0245711 A1* 10/2011 Katra .................. A61B 5/1072
600/547
(Continued)

*Primary Examiner* — Lynsey C Eiseman
*Assistant Examiner* — Jessandra F Hough
(74) *Attorney, Agent, or Firm* — Miller IP Law, LLC

(57) ABSTRACT

A method, system, or device for hydration monitoring using trend analysis. The method may include measuring a physiological measurement of an individual with a sensor to obtain trend data correlating to a hydration level of the individual. The method may include removing an abnormal shift or an abnormal change from the trend data. The method may include removing abnormal shifts and changes from the raw trend data. The method may include identifying a trend parameter for the trend data, the trend parameter indicating a change in the hydration level of the body. The method may include determining a reference value for the trend parameter. The method may include identifying a change in the trend data for the trend parameter, the change in the trend data indicating a change in the hydration level of the individual.

20 Claims, 34 Drawing Sheets

(51) Int. Cl.
  *A61B 5/1455* (2006.01)
  *A61B 5/06* (2006.01)
  *A61B 5/053* (2006.01)
  *A61B 5/11* (2006.01)
  *G16H 15/00* (2018.01)
  *A61B 5/08* (2006.01)
  *A61B 5/024* (2006.01)
  *A61B 5/0245* (2006.01)
  *A61B 5/021* (2006.01)
  *A61B 5/0535* (2021.01)

(56) References Cited

U.S. PATENT DOCUMENTS

| | | | | |
|---|---|---|---|---|
| 2011/0251513 | A1* | 10/2011 | Chetham | A61B 5/0537 |
| | | | | 600/547 |
| 2014/0316287 | A1* | 10/2014 | Watson | A61B 5/7275 |
| | | | | 600/485 |
| 2016/0029958 | A1* | 2/2016 | Le | A61B 5/6835 |
| | | | | 600/383 |
| 2016/0374588 | A1* | 12/2016 | Shariff | A61B 5/7475 |
| | | | | 600/547 |

\* cited by examiner

TREND ANALYSIS FOR HYDRATION MONITORING

RELATED APPLICATIONS

This application claims the benefit of U.S. Provisional Application No. 62/242,923, filed Oct. 16, 2015, the entire contents of which are incorporated by this reference.

BACKGROUND

Dehydration is a condition in which fluid in a living body decreases below a living body's normal functioning level. Dehydration can occur when an individual is exercising for extended periods of time, intakes little or no fluids, or an ambient temperature rises to a point where an individual cannot excrete enough sweat to cool their body and maintain a normal body temperature. Individuals that regularly exert themselves in high humidity environments, high-temperature environments, or for extended periods of time are prone to experience dehydration or symptoms of dehydration. Elderly individuals and children are also prone to experiencing dehydration or symptoms of dehydration.

In less severe cases of dehydration, an individual's ability to perform tasks will begin to deteriorate. For example, in the case of long distance endurance athletes, an athlete that becomes dehydrated by a loss of as little as 2% body weight may begin to have their performance impaired. Losses in excess of 5% of body weight can decrease the capacity of an individual to perform a task by as much as 30%.

Another group of people in danger of dehydration are individuals with dysentery. Dysentery is a gastrointestinal disorder characterized by inflammation of the intestines, particularly the colon. Diarrhea and vomiting are typical side effects of patients with dysentery, especially in the case of small children. As dysentery patients suffer from diarrhea and vomiting, they are unable to maintain a proper hydration level, causing them to become dehydrated. Such a dehydrated state exasperates the patient's condition, causing their health to further deteriorate and prolong recovery time.

BRIEF DESCRIPTION OF THE DRAWINGS

The disclosure will be understood more fully from the detailed description given below and from the accompanying drawings of various embodiments of the disclosure. The drawings, however, should not be taken to limit the disclosure to the specific embodiments, but are for explanation and understanding only.

DESCRIPTION OF EMBODIMENTS

Figure 1:
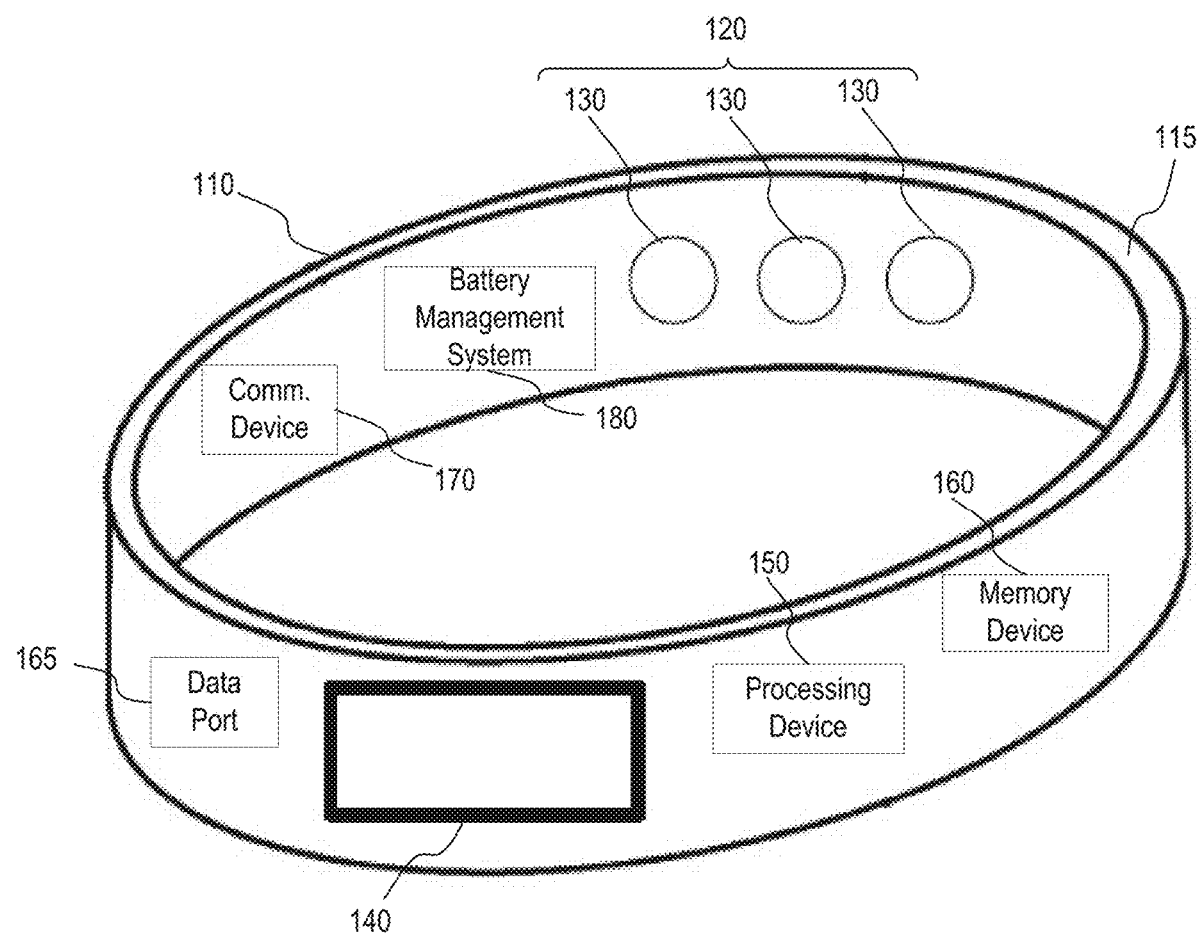
FIG. 1 depicts an electronic device according to one embodiment.

Dehydration, if left untreated or unaddressed, will progressively become worse until an individual is in a serious dehydrated condition. Typically when at least one-third of the fluid in a living body is lost, a temperature regulating function of the living body ceases to work correctly. This dysfunction causes a body temperature of the living body to increase, which causes the fluid level in the living body to be further reduced. The increase in body temperature and reduced fluid level can cause an uncontrolled spiral. As the living body becomes more dehydrated, illnesses such as heat cramping, heat stroke, heat exhaustion, desert syndrome, and heatstroke can occur. In severe cases of dehydration, organs do not function properly or may fail entirely.

The embodiments and examples described herein are methods, systems, and devices for monitoring and determining a hydration condition of an individual. In one example, the hydration condition is a measure of a hydration level of the individual compared to an average hydration level or typical hydration level of the individual, e.g., a baseline hydration level of the individual. The hydration levels can include: hyponatremia (i.e., overhydrated), fully hydrated, partially dehydrated, and severely dehydrated. In another example, the hydration condition is an indicator of symptoms level of the individual experiencing various degrees of hydration. The symptom levels can include: dry mouth for slight dehydration, physical fatigue or mental fatigue for mild dehydration, sunken eyes or shriveled and dry skin for severe dehydration, and so forth.

An electronic device can monitor trending of measurement information to determine a hydration condition of a user. The electronic device can be a wearable measurement device with processing logic coupled to a sensor interface. The processing logic that includes hardware (e.g., circuitry, dedicated logic, programmable logic, microcode, etc.), software (e.g., instructions executed by a processing device), firmware, or a combination thereof. The sensor can also be coupled to an impedance sensor. The sensor interface can use the impedance sensor to take impedance measurements. The processing logic can monitor changes (e.g., trending) the impedances measurements taken from a user. A change in the trending of the impedance measurements can indicate a change or shift of a hydration level of the user. One advantage of monitoring a hydration condition of a user is that dehydration can be detected in the early stages before an individual's performance levels are impacted or they become dangerously dehydrated. For example, typically people are unaware of dehydration symptoms at early stages, based on self-awareness. As a result, dehydration symptoms can go untreated until an individual feels dizzy or weak and realizes something is wrong. By the time an individual feels dizzy or weak, they are already in a serious dehydration condition. When an individual reaches a serious dehydration condition, medical treatment may be required and the window to treat the individual may become severely shortened. Monitoring a user's hydration condition can detect early stages of dehydration and alert the user or third party to respond to a change in the user's hydration condition.

FIG. 1 depicts an electronic device 110 according to one embodiment. In one embodiment, the electronic device 110, also referred to herein as a wearable user measurement (UMD) device, can be a wristband, a headband, an armband, a chest band, a leg band, an ankle band, a strap, a garment, piece of clothing (such as a shirt), an accessory, or other object that can be shaped to attach or couple to an individual at a desired location on the individual. In another embodiment, the electronic device 110 can be integrated into other wearable objects such as a hard hat, a safety harness, a safety lockout device, shoes, a bag, and so forth. In another embodiment, the electronic device 110 can be a computer device or processing device that is incorporated into an accessory worn on the body or an item of clothing.

In one example, a desired location can be a location on the individual that is comfortable for the individual to wear the electronic device 110 for an extended period of time, such as a 24-hour period. For example, as many individuals are accustom to wearing wristwatches, a desired location of the electronic device 110 may be the wrist. In another example, a desired location is a location on the individual that will provide an optimal or higher measurement accuracy level than other locations, such as a location on the individual that is the most sensitive to a selected physiological measurement. For example, the underside of the wrist may be an optimal location to make physiological measurements. In one embodiment, the electronic device 110 can include an impedance sensor or an optical sensor. The underside of the wrist can be an optimal location because a user's veins and arteries are closer to the skin surface than at many other locations on the body. When the electronic device 110 takes impedance measurements or light spectroscopy measurements to monitor a hydration condition, the blood of the user can be used to take non-invasive impedance measurements or light spectroscopy measurements. The veins and arteries may be closer to the skin surface can increase the accuracy of the measurements. The electronic device 110 can be shaped to attach to the individual at a desired location.

The electronic device 110 can include a housing 115 with an inner compartment or chamber. The chamber can include space to house: a sensor array 120, a sensor 130, a display 140, a processing device 150, a memory device 160, a communication device 170, and/or a battery management system (BMS) 180. In one embodiment, the processing device 150 can include a sensor interface coupled to the sensor array 120 or the sensor 130.

The housing 115 can be hermetically sealed, e.g., airtight, waterproof, sweat proof, dust proof, and so forth. In another example, the housing can be a unibody (e.g., a single unit), where components such as the sensor 130 can be sealed with the unibody. In another embodiment, the housing 115 can include multiple pieces, such as a first housing piece and a second housing piece, that are sealed together to form a hermetically sealed housing 115.

In one example, the electronic device 110 can be an invasive device attachable to (or implantable within) a body of a user to obtain invasive physiological measurements from the user. In another example, the electronic device 110 can be a non-invasive device attachable to the body of the user to obtain non-invasive measurements from the user.

The electronic device 110 can include a sensor 130 or a sensor array 120 with one or more sensors 130. In one example, the sensor 130 or the sensor array 120 can be integrated into the electronic device 110. In another example, the sensor 130 or the sensor array 120 can be coupled to the sensor interface of the processing device 150. In one example, the sensor 130 can be a physiological sensor. The physiological sensor can include: a pulse oximeter, an electrocardiography (ECG) sensor, a fluid level sensor, an oxygen saturation sensor, a body temperature sensor (skin temperature or core temperature), a plethysmographic sensor, a respiration sensor, a breath rate sensor, a cardiac sensor, an optical sensor, an impedance sensor, a bio-impedance sensor, a spectrometer, a heart rate sensor, a blood pressure sensor, or other physiological sensors. In another example, the sensor 130 can be a Newtonian sensor. The Newtonian sensor can include: a two-dimensional (2D) accelerometer, a three-dimensional (3D) accelerometer, a gyroscope, a magnetometer, a vibration sensor, a force sensor, a pedometer, a strain gauge, and so forth. In another example, the sensor 130 can be a location sensor, a plethysmograph sensor, a breath sensor, or an oxygen level measurement. The location sensor can include: a global positioning system (GPS); a triangulation system; and so forth. In another example, the sensor 130 can be an environmental sensor. The environmental sensor can include: a humidity sensor, an ambient temperature sensor, an altitude sensor, a barometer, a weather sensor, and so forth. In one embodiment, the sensor 130 can be a non-invasive sensor. In one embodiment, one or more of the physiological sensors, the Newtonian sensors, or the environmental sensors can be integrated into the electronic device 110 or physically coupled to the electronic device 110. In another example, one or more of the physiological sensors, the Newtonian sensors, or the environmental sensors can be physically separated from the electronic device 110 and can communicate data with the electronic device, either directly or indirectly as discussed herein.

The electronic device 110 can include a display 140 to show information to a user or a third party based on the measurements from the sensor 130 or the sensor array 120. In one embodiment, the display 140 can show the time, e.g., a clock. In another embodiment, the information shown on the display 140 may include measurement information, such as: a heart rate of an individual, a breathing rate of the individual, a blood pressure of the individual, a bio-impedance level of the individual, a hydration level of the individual, a hydration score or index indicating an overall hydration condition of the individual, a performance score or index indicating an overall effect of a hydration condition on physical or mental performance of the individual, and so forth. In another example, the information shown on the display 140 may include recommendations, such as: a recommendation to take a break; a recommendation to go home; a recommendation to go to a hospital; a recommendation to drink fluids; or other recommendations. In another example, the information shown on the display 140 may include alerts, such as: a medical alert that the user may be experiencing a medical episode; an alert to take medication; an alert that an environment adjacent the user may not be safe; an alert that the user has fallen down; or other alerts. In another example, the information shown on the display 140 may include: health status information, health risk information, medication information, and other information. In one example, the alert can be sent another device (such as a caregiver or supervisor's device). The alert can be a text message, email, telephone call, and so forth.

In another embodiment, the display 140 can display information to a user or a third party based on information from other devices in communication with the electronic device 110. For example, the electronic device 110 can receive information from an automobile or a smart home device of a user or a third party. In this example, the information from the automobile or the smart home device can include ambient temperatures, humidity information, weather information, and so forth. The electronic device 110 can display the information from the automobile or the smart home device or use it in combination with measurements taken using the sensor 130 or the sensor array 120 to determine and display other information, such as a hydration level of the user.

In another example, the electronic device 110 can communicate instructions to other devices based on sensor measurements of the device. For example, the electronic device 110 can take skin temperature measurements using a skin temperature sensor of the electronic device 110 and determine that an individual's skin temperature indicates that their body temperature exceeds or is below a body temperature range. When the individual's body temperature exceeds or is below a body temperature range, the electronic device 110 can determine that the ambient temperature for the location of the individual is exceeded or is below an ambient temperature range. The electronic device 110 can send an instruction to another device, such as a heating, ventilating, and air conditioning control unit (HVAC), that request that the other device adjusts the ambient temperature to be within an ambient temperature range.

In another embodiment, the processing device 150 can determine an error with the sensor 130 or the sensor array 120 and display the error to the user or the third party using the display 140. For example, the processing device 150 can determine that the sensor 130 or the sensor array 120 is not interfacing with the user properly and can use the display 140 to display an error message to the user. In one embodiment, the sensor 130 or the sensor array 120 is not interfacing with the user properly when the sensor 130 or the sensor array 120 is only partially contacting the body of the individual or is not completely contacting the body of the individual. In another embodiment, the sensor 130 or the sensor array 120 is not interfacing with the user properly when an object or particle is interfering with the processing device 150 using the sensor 130 or the sensor array 120 to take physiological measurements of the user, environmental measurements, Newtonian measurements, or other measurements. In one example, the processing device 150 can determine that object or particle is interfering with taking measurements when measurement information is outside a defined measurement range or there is a discontinuity in the measurement information that exceeds a threshold level for the discontinuity. For example, when dirt comes between the sensor 130 or the sensor array 120 and the body of the user, the dirt can cause a discontinuity in the measurement information. When the processing device 150 determines the discontinuity in the measurement information, the processing logic can use the display 140 to display an error message associated with the discontinuity.

In another embodiment, the sensor 130 or the sensor array 120 is not interfacing with the user properly when the electronic device 110, the sensor 130, or the sensor array 120 has become dislocated or displaced. For example, measurements taken using the sensor 130 or the sensor array 120 with a first orientation can have a higher accuracy level than measurements taken using the sensor 130 or the sensor array 120 with a second orientation. In one example, the first orientation is an orientation where the user is wearing the electronic device 110 in a correct orientation and the second orientation is an orientation when the electronic device 110 has slipped or shifted to a different orientation. When the electronic device 110 has slipped or shifted the second orientation, the processing device 150 identifies that a measurement is outside a defined measurement range or there is a discontinuity in measurement information and uses the display 140 to display an error message associated with the slippage or shifting.

In one example, the display 140 can be a touch screen display, such as a capacitive touch screen or a resistive touch screen. In another example, the display 140 can display a graphical user interface (GUI) to receive information. In another example, the electronic device 110 can include a data port 165, such as a universal serial bus (USB) port, a mini-USB port, a micro-USB port, a Lightning® port, and so forth. In another example, the electronic device 110 can include a wireless communications device 170 (as discussed in the proceeding paragraphs) to send or receive information.

The processing device 150 can analyze or process measurements, received information, user input data, and/or other types of data. In one example, the electronic device 110 can monitor stress on a respiratory system of the individual. For example, the electronic device 110 can use the sensor 130, such as an oxygen saturation sensor, to monitor the stress on a respiratory system of the individual.

In another example, the electronic device 110 can use one or more sensors 130 in the sensor array 120 to monitor stress on a plurality of systems of an individual, such as a biological system or a body system. The biological system may include a respiratory system, a cardiovascular system, a nervous system, an integumentary system, a urinary system, an excretory system, a digestive system, an immune system, an endocrine system, a lymphatic system, a muscular system, a skeletal system, a reproductive system, and other systems. The body system may include two or more organs working together in the execution of a specific bodily function, e.g., a neuroendocrine system, a musculoskeletal system, etc. For example, the electronic device 110 can monitor stress on the cardiac system of an individual using a blood pressure sensor of the sensor array 120 and can monitor the stress on the respiratory system of the individual using an oxygen saturation sensor of the sensor array 120.

The electronic device 110 can monitor biological systems, organs, body parts, body system, or other areas of an individual. In one example, the electronic device 110 can monitor or aggregate stress measurements from the sensors of the sensor array with other measurements, such as a lung capacity of an individual, a hematocrit (HCT), an oxygen saturation level, and/or other medical measurements. In another example, the electronic device 110 can analyze the aggregated measurements to determine stress on one or more biological systems, organs, body parts, and/or body system and use the aggregated measurements to determine medical, health, hydration, and/or safety conditions.

In one example, the electronic device 110 can use the sensor array 120 to monitor a medical condition of an individual, such as a cardiac condition, under various environments or conditions for continuous, semi-continuous, or a periodic period of time on a long-term or protracted basis. In one example, sensor measurements can be collected using the sensor 130 in the sensor array 120. In another example, the sensor measurements can be stored on a non-tangible computer readable medium device 160 (e.g., a memory device) coupled to the processing device 150 or in communication with the processing device 150.

The battery management system (BMS) 180 can include: one or more batteries (such as a rechargeable battery), a charger, and a management device. The management device can manage and control power, e.g., power to and from the one or more batteries or regulate power of the electronic device 110. For example, the management device can direct power received from an external power source, such as wall outlet, via the data port 165 (e.g., a USB port) and can recharge the one or more batteries. The BMS 180 can include a wireless power system with a wireless power coil to receive power. The management device can direct power received via the wireless power system to the one or more batteries. In one example, the management device can direct power to components or systems of the electronic device 110, such as the sensor array 120, the sensor 130, the display 140, the processing device 150, the memory device 160, and/or the communication device 170. In another example, the management device can be a processor or another processing device, independent of the processing device 150, that can manage and control the power. In another example, the management device can be software executed by the processing device 150 or processing logic to manage the power.

In one embodiment, the BMS 180 can determine when a charge level the one or more batteries are below a threshold amount and can send a notification to the user indicating that the electronic device 110 needs to be charged. In one example, the electronic device can send the notification to the user using a sensory device such as a vibrator, a speaker, a display, and so forth.

Figure 2:
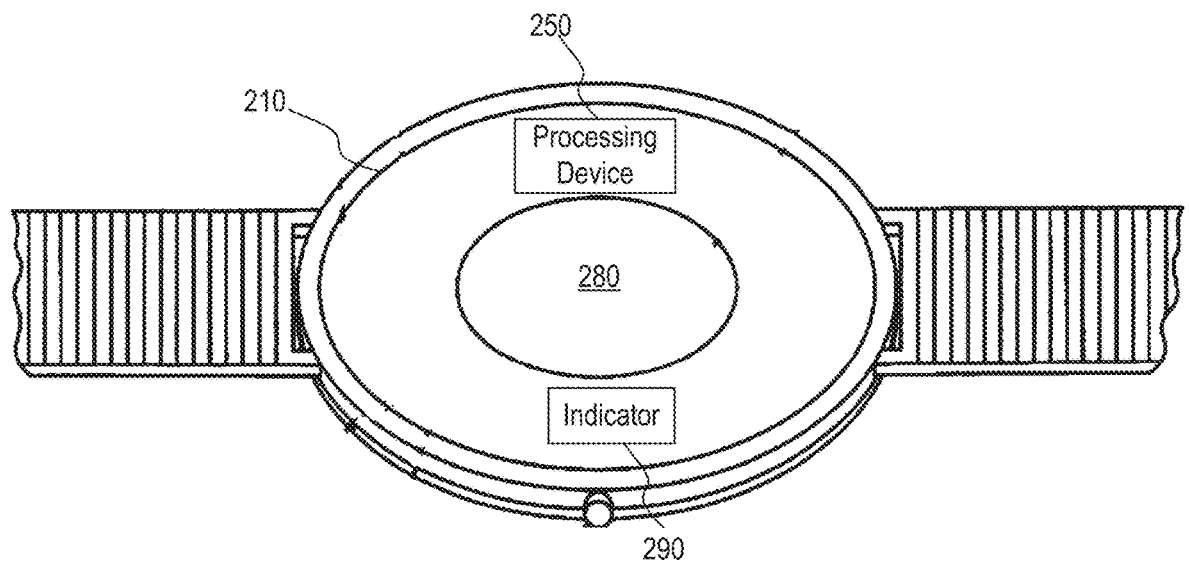
FIG. 2 illustrates an underside view or interior view of the electronic device according to one embodiment.

FIG. 2 illustrates an underside view or interior view of the electronic device 210 according to one embodiment. The electronic device 210 can take selected measurements using one or more sensors 280 and a processing device 250, according to one embodiment. The electronic device 210 may also include one or more indicators 290 used to alert the user of the electronic device 210 of an event. The indicator 290 may be located at various locations of the electronic device 210 based on a type of the indicator 290. For example, the indicator 290 can be a display or light located on the top of the electronic device 210. In another example, the indicator 290 can be a vibrator on the bottom of the electronic device 210. In another example, the indicator 290 can be a speaker integrated within the electronic device 210. The processing device 250 may receive measurement information from the one or more sensors 280 and can analyze the measurement information to determine selected information, such as physiological information, medical information, safety event information, alert information, and so forth. In one example, the selected information can be hydration level information, cardiac information (e.g., blood pressure or heart rate), blood oxygen level information, skin luminosity information, or other user information.

Figure 3:
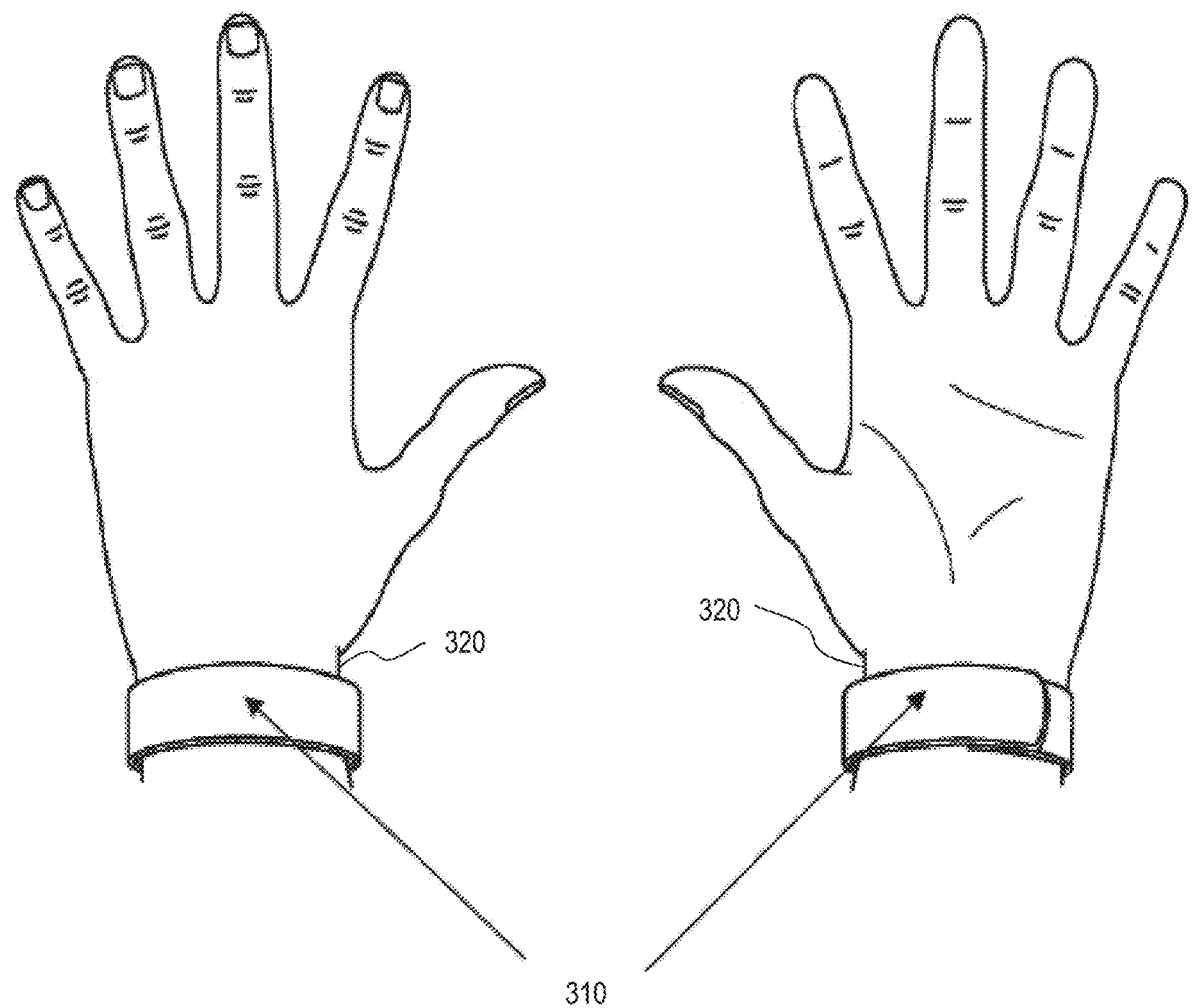
FIG. 3 depicts a top and a bottom perspective of an electronic device attached to a wrist of an individual according to one embodiment.

FIG. 3 depicts a top and a bottom perspective of an electronic device 310 attached to a wrist 320 of an individual according to one embodiment. The electronic device 310 may be located on the wrist of an individual and may take one or more measurements at the wrist location. In one example, the electronic device 310 can cover or wrap around the circumference of the wrist 320 of the individual. In another example, the electronic device can be a detachable device that can be coupled or attached to a holder (such as a wristband or chest strap).

Figure 4:
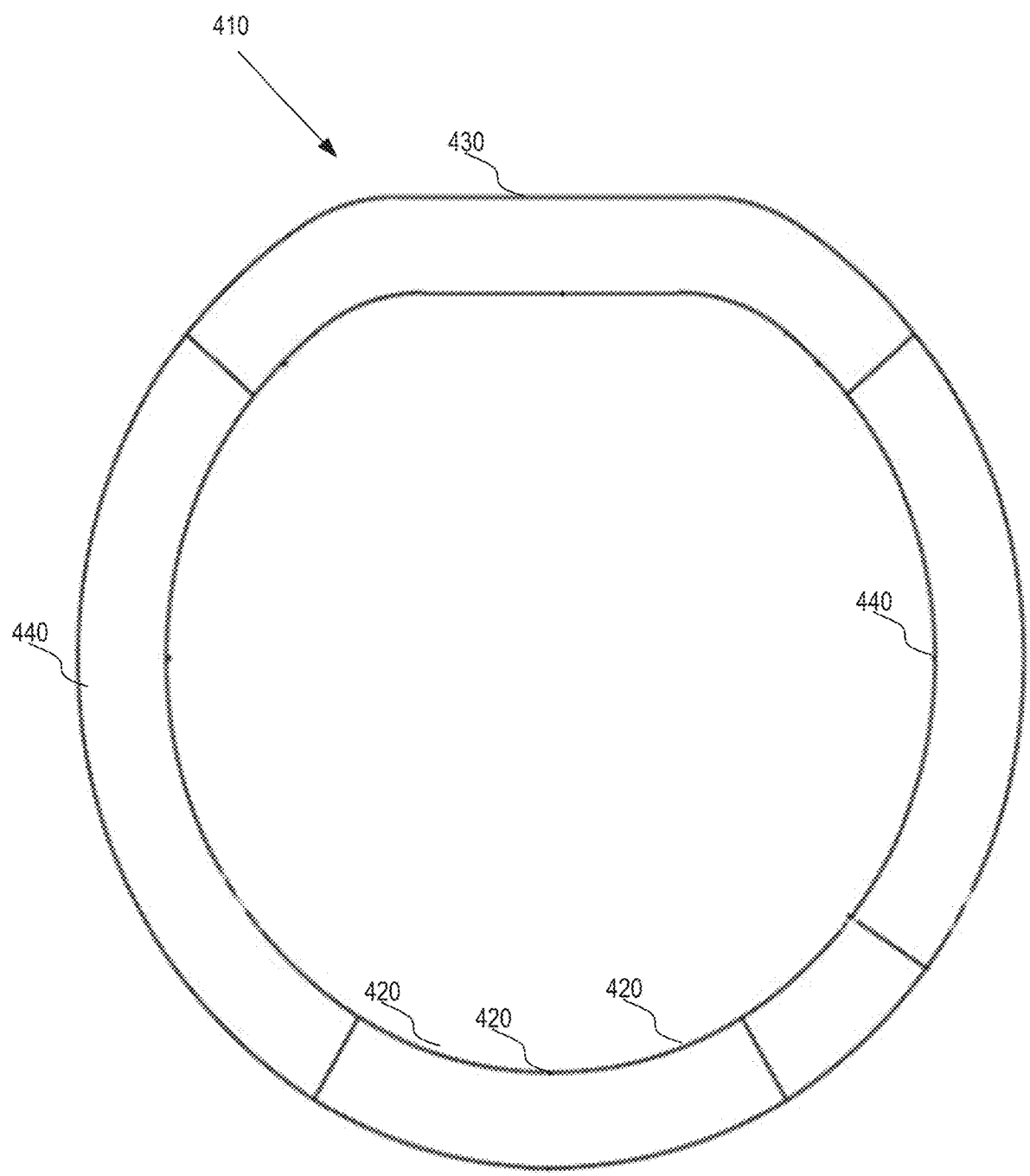
FIG. 4 depicts a side view of an electronic device according to one embodiment.

FIG. 4 depicts a side view of an electronic device 410 according to one embodiment. The electronic device 410 may be the same as the electronic devices as shown in figures discussed herein. The electronic device 410 can include one or more integrated sensors 420. In one example, the electronic device can have a circular shape, a square shape, or other shapes. In another example, the electronic device 410 can have a flat top portion 430 and a circular remaining portion 440 to fit the contour or shape of a wrist on an individual. An advantage of the electronic device 410 fitting to contours of the wrist can be to align the sensors 420 of the electronic device 410 with a desired location on the wrist of the individual (such as a bottom, side, or top of the wrist). Another advantage of the electronic device 410 fitting to contours of the wrist can be to provide and/or maintain proper contact between the sensor 420 of the electronic device 410 and a body of the user. The location of the sensors 420 is not intended to be limiting. The sensor 420 can be located at different locations on the electronic device 410. Additionally, a shape of the electronic device 410 is not intended to be limiting. The electronic device 410 can be a variety of different shapes, such as oval, circular, rectangular, and so forth. The location on a body of the user that the electronic device 410 attaches is not intended to be limiting, as discussed in the preceding paragraphs.

Figure 5:
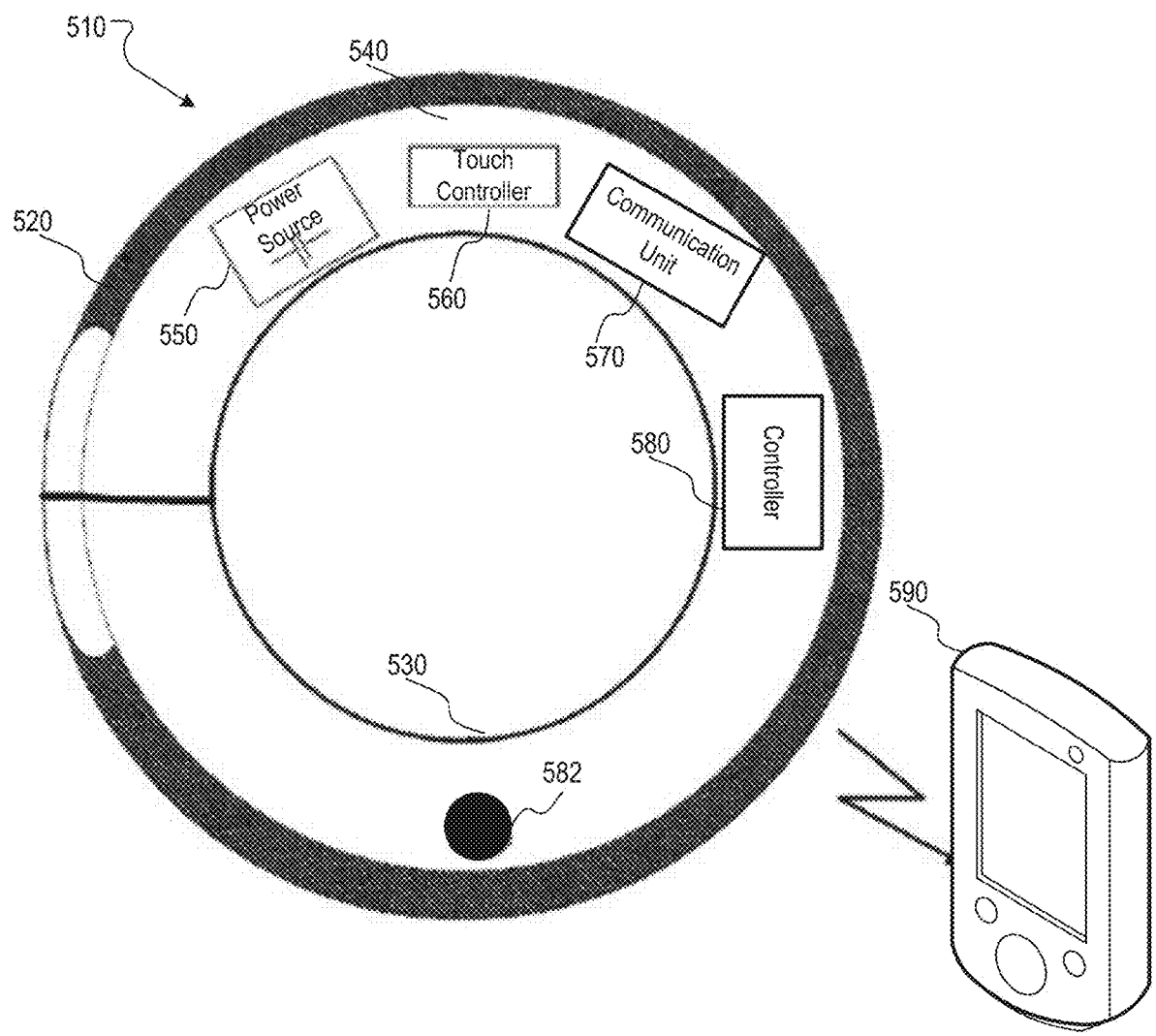
FIG. 5 depicts an electronic device according to one embodiment.

FIG. 5 depicts an electronic device 510 according to one embodiment. The electronic device 510 can be a substantially circular band with an outer surface 520 and an inner surface 530. In one example, the outer surface 520 or the inner surface 530 can be made of a flexible or non-rigid material, such as rubber, polyurethane, and so forth. In another example, the outer surface 520 or the inner surface 530 can be made of a semi-rigid or rigid material, such as plastic, metal, and so forth. In another example, a portion of the outer surface 520 or the inner surface 530 can be the flexible or non-rigid material and a portion of the outer surface 520 or the inner surface 530 can be the semi-rigid or rigid material. In another example, a portion of the inner surface 530 that contacts a body of the user is a conductive material. For example, one or more sensors 582 are bio-impedance sensors that are conductive rubber pads that contact the body of the user and are used by processing logic to make bio-impedance measurements.

In one example, a cavity or chamber 540 can be between the outer surface 520 and an inner surface 530. The cavity or chamber 540 can include modules, units, systems, subsystems, or devices of the electronic device 510. For example, the cavity or chamber 540 can house a power source 550, a graphical user interface or touch controller 560, a communication unit 570, a controller 580, one or more sensors 582, and/or other units. The communication unit 570 can wirelessly communicate with an external electronic device 590. The power source 550 can provide power to other units or modules of the electronic device 510. The touch controller 560 can receive user input from an input device. In one example, the input device can be a graphical user interface (GUI) or a touch display and be operable to receive input via the GUI or the touch display. The input device can receive communications from other devices via a communication network (e.g., a wireless network) or a communication connection (such as a universal serial bus). The controller 580 can control systems and subsystems of the electronic device 510.

The power source 550 can be a battery, such as a rechargeable battery. The power source 550 can receive power from another power source such as via a cord plugged into a power source or using wireless power such as inductive wireless charging or resonant wireless charging. The electronic device 510 can include one or multiple sensors 582 (e.g., a sensor array). In one example, the multiple sensors 582 can be different types of sensors.

The electronic device 510 can receive safety event information and/or health information of a user of the electronic device 510 from another device. For example, the electronic device 510 can have a touch controller 560 to receive user input safety event information and/or health information. In one example, the power source 550, the touch controller 560, the communication unit 570, the controller 580, or the one or more sensors 582 can be in direct or indirect communication with each other. For example, the touch controller 560 receives user input information from the input device and communicates the user input information to the controller 580. In this example, the controller 580 includes a processor or processing device to analyze or process the user input information. In another example, the sensor 582 can take a physiological measurement and communicate physiological information to the external electronic device 590 via the communication unit 570. In one embodiment, the external electronic device 590 is an electronic device with a processor, such as a smartphone, electronic tablet, or personal computer. In another embodiment, the external electronic device 590 is a cloud computing system or a server. The external electronic device 590 can analyze or process data or information received from the electronic device 510. In one example, the external electronic device 590 can store the processed data or information. In another example, the external electronic device 590 can send the processed data or information back to the electronic device 510.

Figure 6:
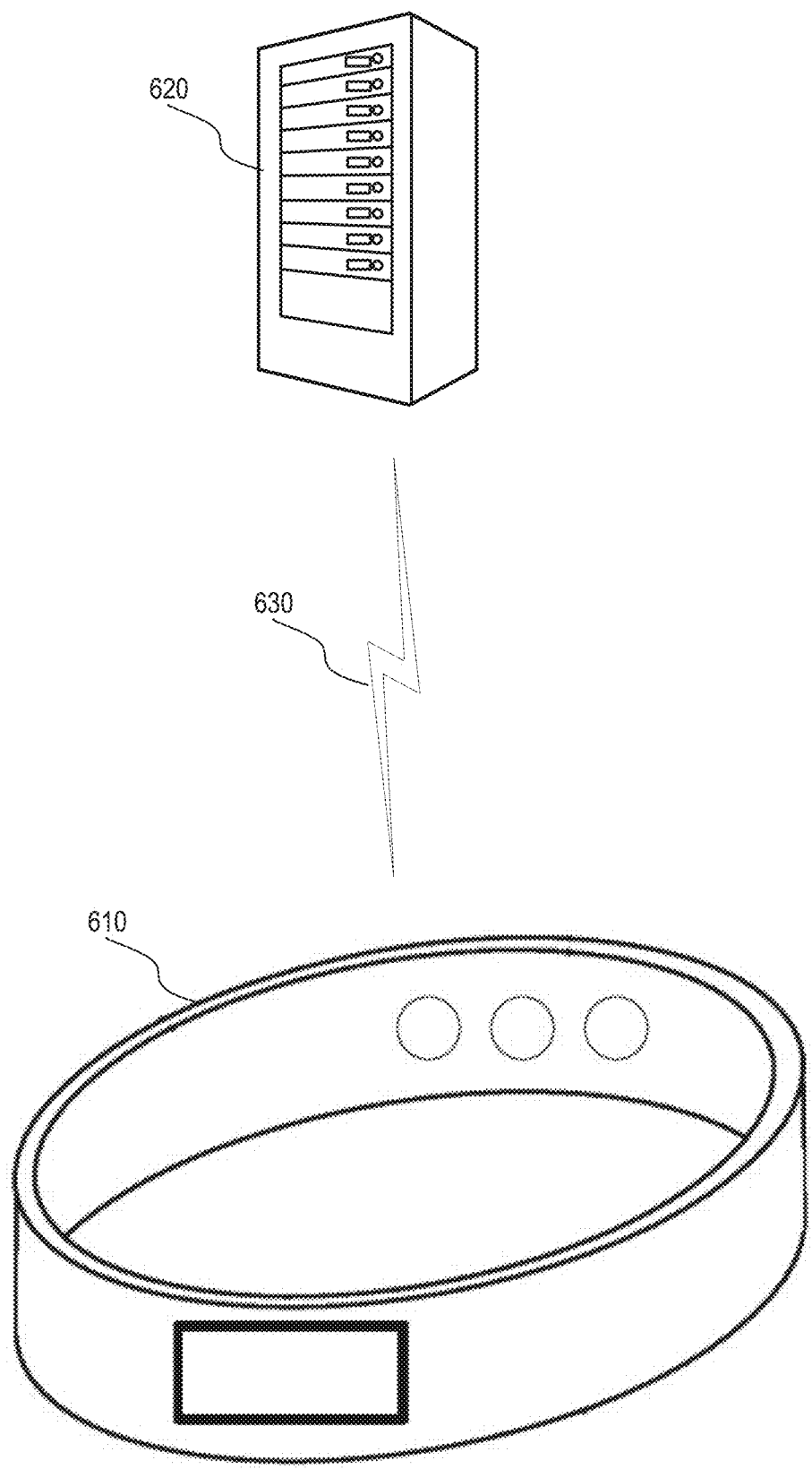
FIG. 6 depicts an electronic device in direct communications with a computing device according to one embodiment.

FIG. 6 depicts an electronic device 610 in direct communications with a computing device 620 according to one embodiment. In one example, sensor measurements collected and/or stored by the electronic device 610 can be processed or analyzed by a processor of the electronic device 610 and/or by a computing device 620 in communication with the electronic device 610. The electronic device 610 can be in direct communication 630 with the computing device 620. In one example, the direct communication 630 can be a Bluetooth® communication link, a Zigbee® communication link, radio signal, or other direct communication systems. In another example, the other computing device 620 can be a server that stores information, such as sensor measurements or safety event information previously taken by the electronic device 610 or sensor measurements or safety event information taken from a group of individuals, as discussed herein. In another example, the computing device 620 can be a mobile computer device, such as a laptop computer, tablet, or a smartphone. The electronic device 610 can communicate information, such as sensor measurements or safety event information, to the computing device 620. In one example, the computing device 620 can process and/or analyze the sensor measurements and/or information received from the electronic device 610. In another example, the computing device 620 can send processed data, analyzed data, measurement results, and/or other information to the electronic device 610. In another example, the computing device 620 can communicate calibration information to the electronic device 610.

Figure 7:
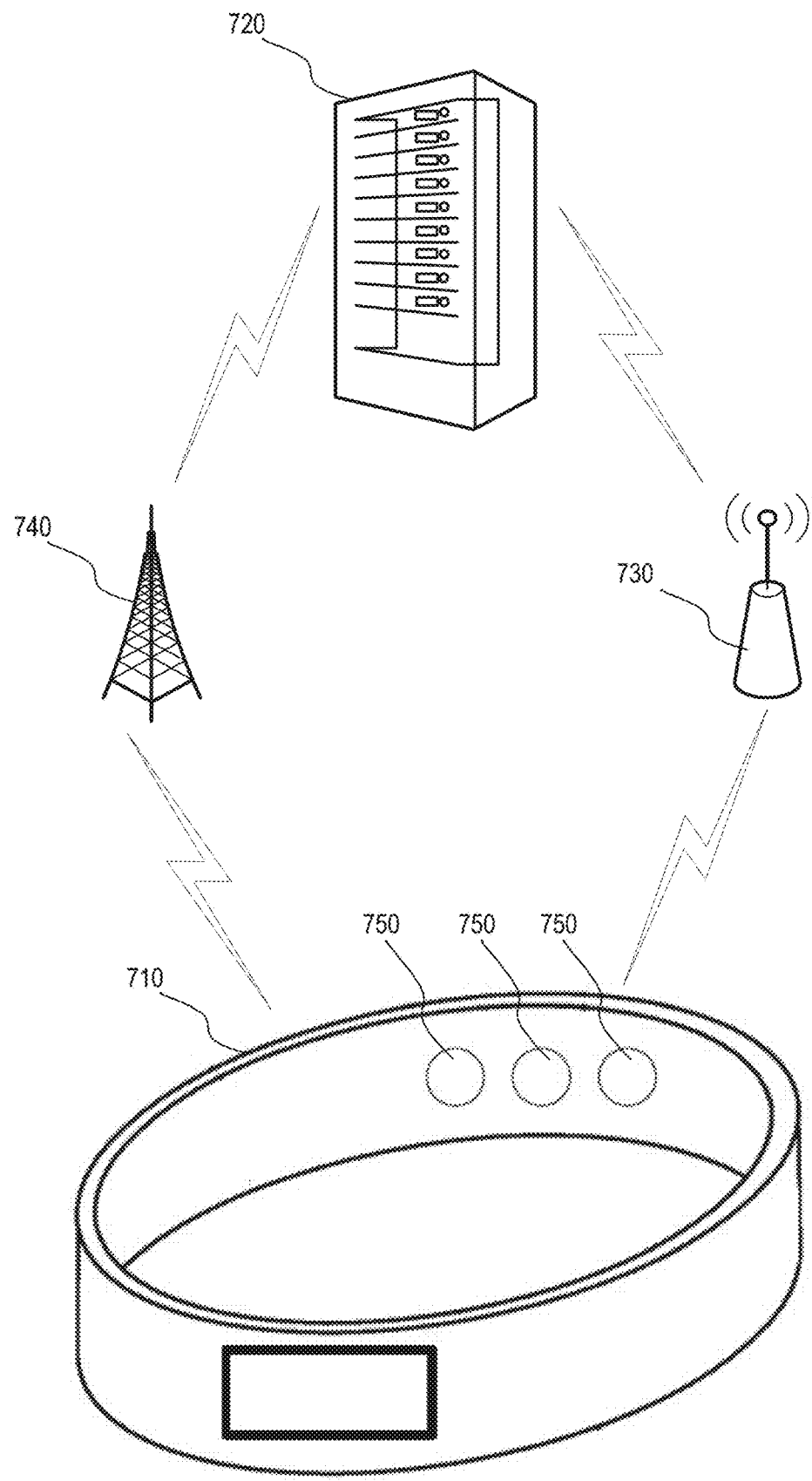
FIG. 7 depicts an electronic device and a computing device in indirect communication using a communications network according to one embodiment.

FIG. 7 depicts an electronic device 710 and a computing device 720 in indirect communication using a communications network according to one embodiment. In one embodiment, the electronic device 710 can be a standalone device with a processing device to analyze or process: information taken from one or more sensors 750 of the electronic device 710; information received from other devices; and/or information stored in a memory of the electronic device 710.

In another embodiment, the electronic device 710 communicates locally with the computing device 720 use a wireless communication network 730 or a cellular communication network 740. The local computing device 720 can be a smartphone, tablet device, personal computer, laptop, a local server, and so forth. In another embodiment, the electronic device 710 communicates with a non-local or remote computing device 720 using a wireless communication network 730 or a cellular communication network 740. The non-local or remote computing device 720 can be a remote server, a cloud-based server, a back-end server, or other remote electronic devices.

In one example, the wireless communication network 730 is a cellular network employing a third generation partnership project (3GPP) release 8, 9, 10, 11, or 12 or Institute of Electronics and Electrical Engineers (IEEE) 802.16p, 802.16n, 802.16m-2011, 802.16h-2010, 802.16j-2009, 802.16-2009. In another example, the electronic device 710 may provide a secure wireless area network (WLAN), a secure PAN, or a wireless fidelity Private Wireless Wide Area Network (PWAN) to communicate with the computing device 720. The electronic device 710 in the WLAN may use the Wi-Fi® technology and IEEE 802.11 standards defined by the Wi-Fi Alliance® such as the IEEE 802.11-2012, IEEE 802.11ac, or IEEE 802.11ad standards. Alternatively, the electronic device 710 and the computing device 720 in the WLAN may use other technologies and standards. Similarly, the electronic device 710 in the PAN or WPAN may use a Bluetooth® technology and IEEE 802.15 standards defined by the Bluetooth Special Interest Group, such as Bluetooth v1.0, Bluetooth v2.0, Bluetooth v3.0, or Bluetooth v4.0 (including Bluetooth low energy). Alternatively, the electronic device 110 in the secure PAN may use other technologies and standards. In another embodiment, the communications network may be a Zigbee® connection developed by the ZigBee Alliance such as IEEE 802.15.4-2003 (Zigbee 2003), IEEE 802.15.4-2006 (Zigbee 2006), IEEE 802.15.4-2007 (Zigbee Pro). The WAN or PWAN can be used to transmit data over long distances and between different LANs, WLANs, metropolitan area networks (MANs), or other localized computer networking architectures.

The electronic device 710 and the computing device 720 can be in indirect communication using a communications network such as wireless communication network 730 (such as a Wi-Fi® network) and/or using a cellular communication network 740 (such as a 3rd Generation Partnership Project (3GPP®) network) to communicate data or measurement information. In one example, the electronic device 710 can take sensor measurements using a sensor 750 and communicate the sensor measurements to the computing device 720 via the wireless communication network 730 and/or the cellular communication network 740. In another example, the computing device 720 can receive sensor measurements from the electronic device 710 via the wireless communication network 730 and/or the cellular communication network 740 and process the sensor measurements and/or analyze the sensor measurements. When the computing device 720 has processed the sensor measurements and/or analyzed the sensor measurements, the computing device 720 can communicate the processed sensor measurements, analyzed sensor measurements, sensor measurement results, or other information to the electronic device 710 via the wireless communication network 730 and/or the cellular communication network 740.

Figure 8:
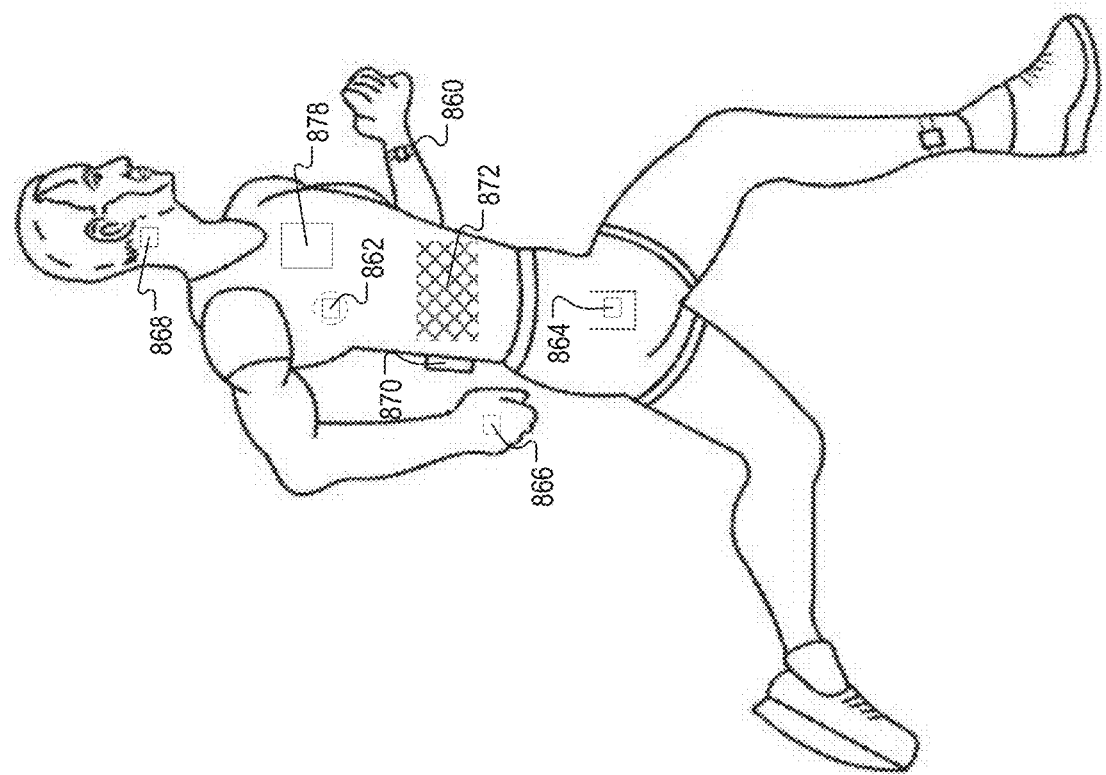
FIG. 8 depicts a body area network (BAN) devices communicating using a BAN according to one embodiment.
Figure 8:
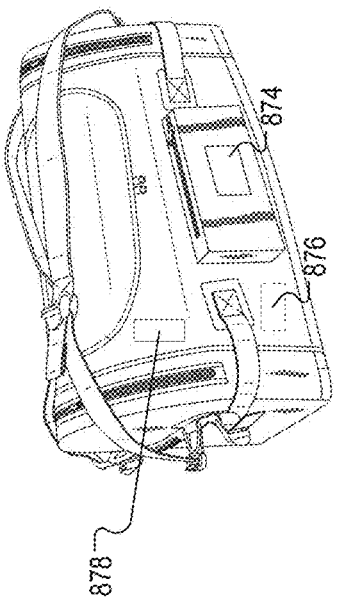

FIG. 8 depicts a body area network (BAN) devices 862-876 communicating using a BAN according to one embodiment. In one embodiment, the BAN can include a wired body area network, a wireless body area network (WBAN), and/or a body sensor network (BSN). The BAN can include multiple wearable computing devices or wearable sensor devices 862-876 that are in communication with each other to send and receive data and information. In one example, the BAN devices can include: a BAN device 860 that is attached or coupled to the body of the user; an BAN device 862 that is implanted into the body of the user; a BAN device 868 that is embedded into the body of a user; a BAN device 870 that is mounted on a surface of the body, and so forth. In another example, the BAN devices can include devices adjacent the user including: a BAN device 864 shaped to fit in a clothes pockets of the user, a BAN device 866 that a user can carry, such as a handheld device; a BAN device 872 that is integrated into clothes of the user; a BAN device 876 located in a user's bag, a BAN device 874 integrated into a user's bag, and so forth. In one embodiment, an electronic device is a BAN device. In another embodiment, the BAN devices 862-876 can be body sensor units (BSUs) that include a processing device, a sensor, and a communication device. The BSUs can communicate with a body central unit (BCU) 878 that is a hub for the BAN devices. The BCU 878 can be located at any of the locations discussed above for the BAN devices 862-876. The BCU 878 can include a processing device, memory, a communication device, and a display. The BCU 878 can receive data from a BAN device 862-876 and analyze the data. In one example, the BCU 878 can display the analyzed data using the display of the BCU 878. In another example, the BCU 878 can send the analyzed data to a BAN device 862-876 or another device. One advantage of the BCU 878 communicating with the BAN devices 862-878 is that the BAN devices 862-878 can be configured to be minimal sensor devices with low power consumption and a compact design where the BCU 878 performs the processing of the data.

In another embodiment, the BCU 878 can be a data hub or data gateway to manage the BAN devices 862-876. In another embodiment, the BCU 878 can provide a user interface to control the BAN devices 862-876. In another embodiment, the BAN devices 862-876 and/or the BCU 878 can use wireless private area networks (WPAN) technology as a gateway or relay to reach longer ranges. In one example, the BCU 878 can us a WPAN to connect the BAN device 862-876 on the body to the internet. For example, medical professionals can access patient data from the BAN devices 862-876 online using the internet independent of a location of a patient.

Figure 9:
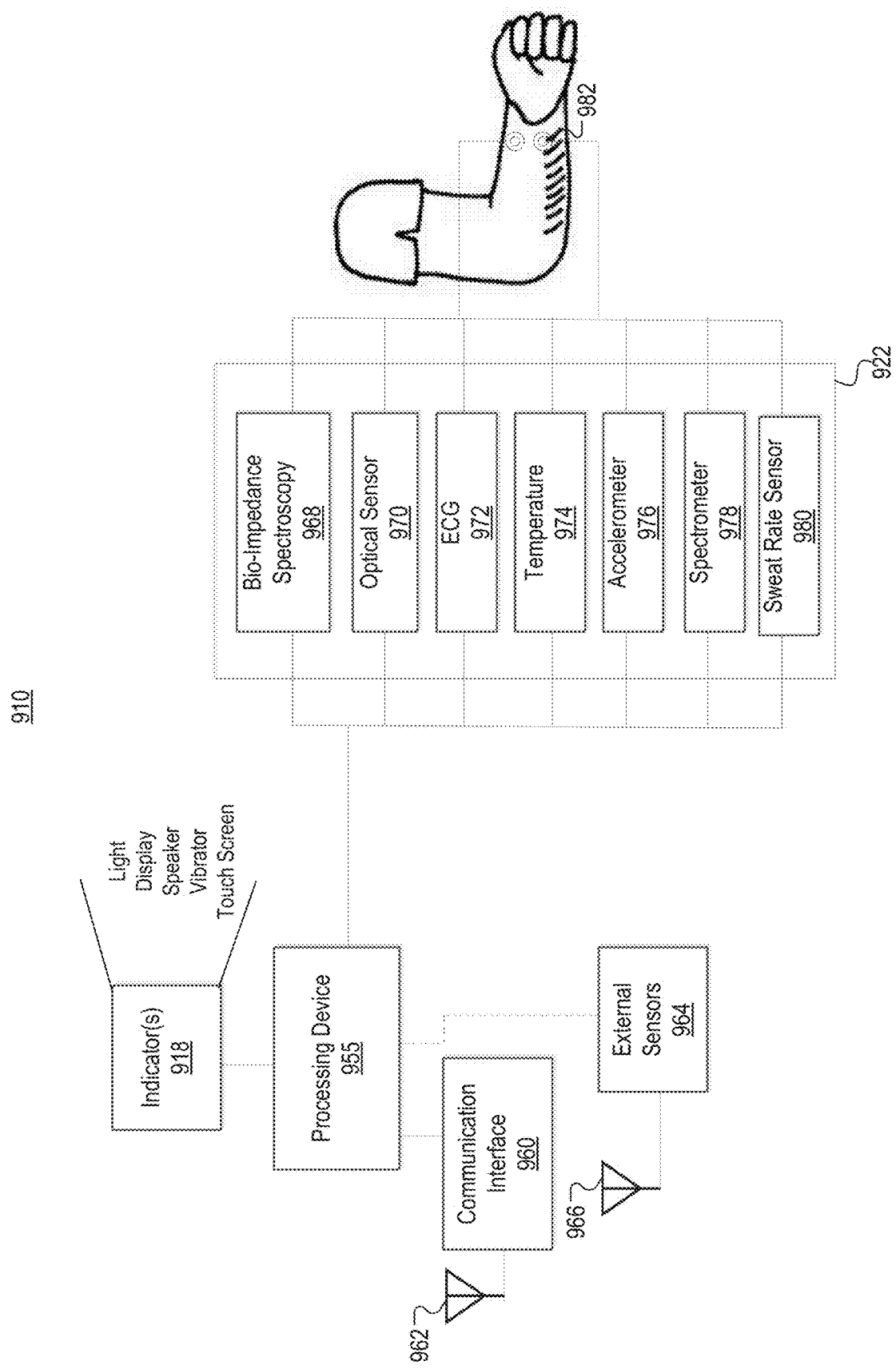
FIG. 9 illustrates a schematic view of an electronic device according to one embodiment.

FIG. 9 illustrates a schematic view of an electronic device 910 according to one embodiment. The electronic device 910 may include the indicators 918, a sensor array 922 (to include at least one of the sensors in FIG. 1, 2, 4, 5, or 7), a processing device 955, a communications interface 960, an antenna 962 coupled to the communications interface 960, external sensors 964, and accompanying antenna(s) 966. In one example, the sensor array 922 may include one or more physiological sensors to take physiological measurements (e.g., measurements related to the body of the individual or animal). The sensor array 922 may include one or more sensors to engage a user of the electronic device to take measurements. In various examples, the sensor array 922 may include, without limitation: a bio-impedance spectroscopy sensor 968 (or simply impedance sensor 968), an optical sensor 970, an electrocardiogram (ECG) sensor 972, a temperature sensor 974 (such as a thermometer or thermistor), an accelerometer 976, a spectrometer 978, a sweat rate sensor 980, and so forth. In one example, the sensor array 922 can contact or engage the body of the user at a location 982.

Figure 10:
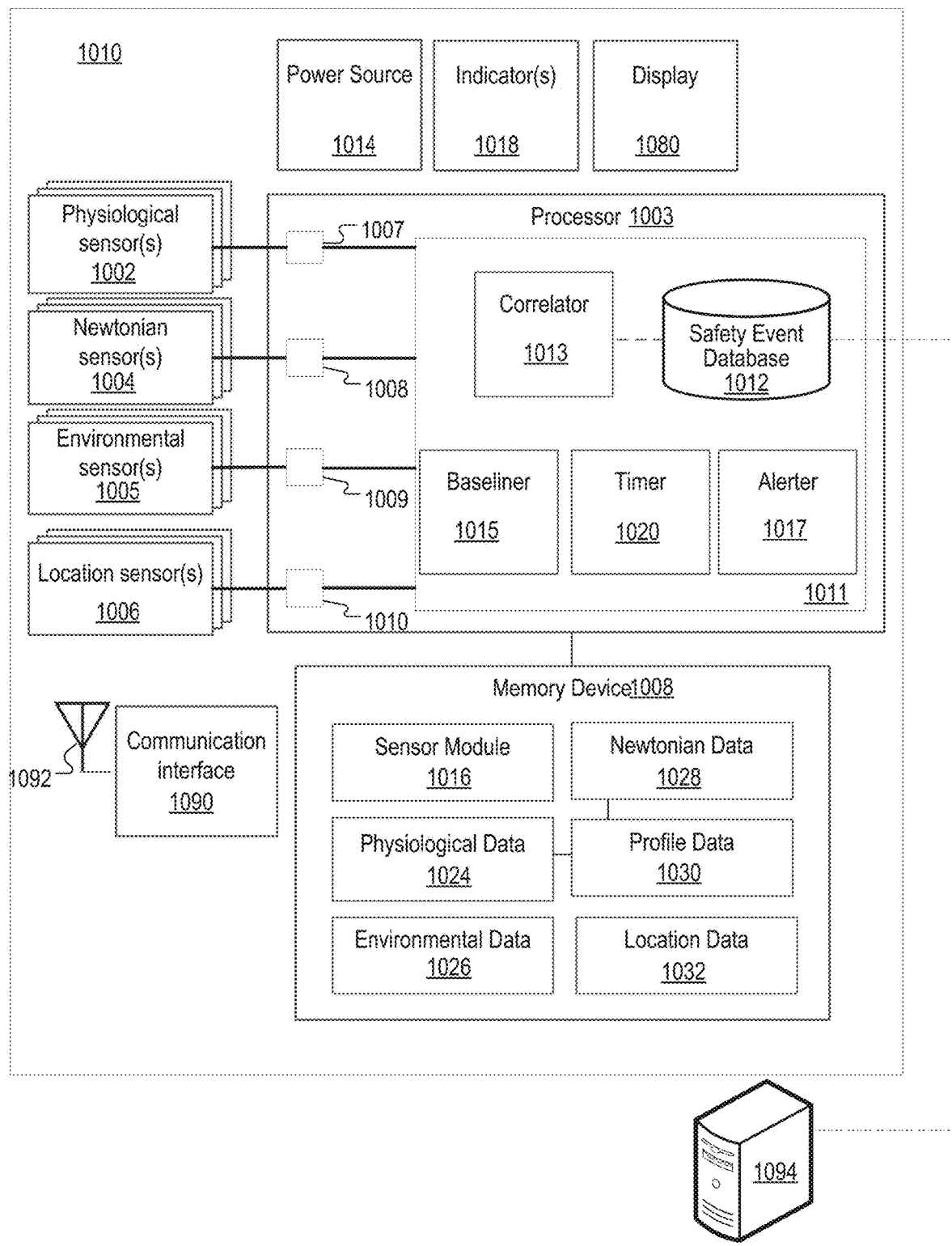
FIG. 10 is a block diagram of the electronic device with a correlator, a baseliner, and an alerter according to one embodiment.

FIG. 10 is a block diagram of the electronic device 1010 with a correlator 1013, a baseliner 1015, and an alerter 1017 according to one embodiment. The electronic device 1010 may include, without limitation, one or more physiological sensor(s) 1002, one or more Newtonian sensor(s) 1004, one or more environmental sensor(s) 1005, one or more location sensor(s) 1004, a processor 1003, a memory device 1008, a display 1080, a communication interface 1090 (such as a radio frequency (RF) circuit), and an antenna 1092 coupled to the communication interface 1090.

In one embodiment, the communication interface 1090 may communicate, via the antenna 1092, with an external electronic device 590 (FIG. 5), a computing device 620 or 720 (FIGS. 6 and 7), and with other wireless devices such as electronic devices 1010 of other users. In one example, the communication interface 1090 may communicate the information using a cellular network, a wireless network, or a combination thereof. In one example, the communications network can be a cellular network employing a third generation partnership project (3GPP) release 8, 9, 10, 11, or 12 or Institute of Electronics and Electrical Engineers (IEEE) 802.16p, 802.16n, 802.16m-2011, 802.16h-2010, 802.16j-2009, 802.16-2009. In another example, the electronic device 110 may provide a secure wireless area network (WLAN), a secure PAN, or a wireless fidelity (Wi-Fi) Private Wireless Wide Area Network (PWAN) to communicate with a device. The electronic device 110 in the WLAN may use the Wi-Fi® technology and IEEE 802.11 standards defined by the Wi-Fi Alliance® such as the IEEE 802.11-2012, IEEE 802.11ac, or IEEE 802.11ad standards. Alternatively, the devices in the WLAN may use other technologies and standards. Similarly, the electronic device 110 in the PAN or WPAN may use the Bluetooth® technology and IEEE 802.15 standards defined by the Bluetooth Special Interest Group, such as Bluetooth v1.0, Bluetooth v2.0, Bluetooth v3.0, or Bluetooth v4.0. Alternatively, the electronic device 110 in the secure PAN may use other technologies and standards. In another embodiment, the communications network may be a Zigbee® connection developed by the ZigBee Alliance such as IEEE 802.15.4-2003 (Zigbee 2003), IEEE 802.15.4-2006 (Zigbee 2006), IEEE 802.15.4-2007 (Zigbee Pro). The WAN or PWAN can be used to transmit data over long distances and between different LANs, WLANs, metropolitan area networks (MANs), or other localized computer networking architectures.

In one embodiment, the electronic device 1010 can communicate data with the other devices via another device, such as a smartphone or tablet computing device. For example, the communication interface 1090 can pair with a smartphone via the wireless network. The smartphone can receive data using the wireless network and can communicate the data to the other device. In another embodiment, the electronic device 1010 may communicate information with the other device via repeaters or a relay system. For example, a user of the electronic device 1010 can be outside of a coverage area for the cellular network or the wireless network, e.g., a farm worker out in the field. In this example, the electronic device 1010 can determine that it is outside the coverage area and switch to communicating via the repeaters or the relay system.

In one embodiment, the electronic device 1010 can determine it is outside a coverage area when it does not receive a signal from the cellular network or the wireless network. In another embodiment, the electronic device 1010 can ping the cellular network or the wireless network (such as a tower within the cellular network or the wireless network) and determine that it is outside the coverage area when the electronic device 1010 does not receive a reply to the ping. In another embodiment, multiple electronic devices 1010 can communicate with each other to form a piconet. In this embodiment, a first electronic device can determine it is outside the coverage area and can scan for a second electronic device, where the second electronic device is in the coverage area or in communication with another electronic device in the coverage area. When the first wearable safety finds the second electronic device, the first electronic device can communicate information to an end device or to the cellular network or the wireless network via the second electronic device.

The processor 1003 may include a first sensor interface 1007 for receiving sensor data from the physiological sensor(s) 1002, a second sensor interface 1008 for receiving sensor data from the Newtonian sensor(s) 1004, a third sensor interface 1009 for receiving sensor data from the environmental sensor(s) 1005, a fourth sensor interface 1010 for receiving sensor data from the location sensor(s) 1006, and a processing element 1011. The processing element 1011, in turn, may include a correlator 1013, a baseliner 1015 and/or an alerter 1017. The memory device 1008 may also include, without limitation, a sensor module 1016, physiological data 1024, environmental data 1026, Newtonian data 1028, and profile data 1030, location data 1032.

The electronic device 1010 may include the sensor array 120 (FIG. 1) with two or more sensors. In the depicted embodiment, the electronic device 1010 may include one or more physiological sensors 1002, one or more Newtonian sensors 1004, one or more environmental sensors 1005, one or more location sensors 1006, or a combination thereof. In some instances, the Newtonian sensors 1004 may be physiological sensors. That is, in some embodiment, the activity level may be determined from one or more physiological measurements.

A physiological measurement may be any measurement related to a living body, such as a human's body or an animal's body. The physiological measurement is a measurement made to assess body functions. Physiological measurements may be simple, such as the measurement of body or skin temperature, or they may be more complicated, for example measuring how well the heart is functioning by taking an ECG (electrocardiograph). Physiological measurements may also include motion and/or movement of the body. In some cases, these physiological measurements may be taken as an aggregate, e.g., as physiological data, with which to correlate to other physiological measurements, a physiological parameter, and/or an environmental parameter.

A parameter may be considered a measurable quantity (such as heart rate, temperature, altitude, and oxygen level, as just a few examples). When measurements of parameters are taken in the aggregate, the measurements may form data which may be analyzed and correlated to other data or parameters, to identify trends or to identify when meeting (or exceeding) certain thresholds that trigger alerts or other actions and the like.

The physiological sensors 1002 may include a pulse oximeter sensor, an electrocardiography (ECG) sensor, a fluid level sensor, an oxygen saturation sensor, a body core temperature sensor, a skin temperature sensor, a plethysmographic sensor, a respiration sensor, a breath rate sensor, a cardiac sensor (e.g., a blood pressure sensor, a heart rate sensor, a cardiac stress sensor, or the like), an impedance sensor (e.g., bio-impedance spectroscopy sensor), an optical sensor, a spectrographic sensor, an oxygen saturation sensor, or a sweat rate sensor. Alternatively, other types of sensors may be used to measure physiological measurements, including measurements to determine activity levels of a person wearing the electronic device.

The Newtonian sensors 1004 may be any of the physiological sensors described above, but in some cases, the Newtonian sensors 1004 are activity or motion sensors, such as, for example, a gyroscope sensor, a vibration sensor, an accelerometer sensor (e.g., a sensor that measures acceleration and de-acceleration), a three-dimensional (3D) accelerometer sensor (e.g., sensors that measure the acceleration and de-acceleration and the direction of such acceleration and de-acceleration), a force sensor, a pedometer, a strain gauge, a magnetometer, and a geomagnetic field sensor that may be used for activity level measurements; whereas the physiological sensors 1002 may be used for specific physiological measurements.

In one embodiment, an environmental measurement may be any measurement of an area approximate or adjacent a user. The environmental sensors 1005 may be a humidity sensor, an ambient temperature sensor, an altitude sensor, a barometer, and so forth. A location measurement may be any measurement of a location of the user or a movement of the user. The location sensor 1006 may be a global positioning system (GPS), a triangulation system, or a location sensor. One or a combination of the physiological data 1024, the environmental data 1026, the Newtonian data 1028, the profile data 1030, and the location data 1032 may be obtained from other sources such as through the network 115 from sources reachable in the cloud or online.

In another embodiment, the environmental measurement can be any measurement of a local or central location measurement of where a user is located. For example, one or more environmental sensors 1005 may be located at a location within a threshold radius of the user, such as a threshold radius from the user location. In this example, the environmental sensors 1005 can take environmental measurements and relay the information to the electronic device 1010 or to a communication hub that has a communication channel established with the electronic device 1010. Alternatively, the environmental sensors 1005 can take environmental measurements and relay the information to a processing hub that can analyze the environmental measurements to determine selected environmental factors (such as a humidity level, a heat index, and so forth) and can communicate the environmental factors to the electronic device 1010 or to another electronic device. In another embodiment, the processing hub can receive the environmental measurements from the environmental sensors 1005 and other measurements (such as physiological measurements) from the electronic device 1010. The processing hub can analyze the environmental measurements and the other measurements to determine selected result data, such as a hydration level of a user or a health level of the user. In another embodiment, the electronic device 1010 can take a first set of environmental measurements and the local environmental sensors 1005 can take a second set of environmental measurements. The first set of environmental measurements and the set of environmental measurements can be combined or aggregated and the processing hub and/or the electronic device 1010 can analyze the aggregated environmental measurements.

In another embodiment, the environmental measurements can be from an environmental information outlet or provider. For example, the environmental information outlet or provider is a weather station, a news station, a television station, an online website, a computer or software application (such as a weather channel application or a fitness application for a smartphone or tablet computer), and so forth. The electronic device 1010 or the processing hub can receive the environmental information from the environmental information outlet or provider can use the environmental information to determine selected physiological and/or environmental data or factors.

The first sensor interface 1007 may be coupled to the one or more physiological sensors 1002, a second sensor interface 1009 may be coupled to the one or more Newtonian sensors 1004, a third sensor interface 1009 may be coupled with the one or more environmental sensors 1005, and a fourth sensor interface 1010 may be coupled with the one or more location sensors 1006. The processing element 1011 may be operable to execute one or more instructions stored in the memory device 1008, which may be coupled with the processor 1003. In some cases, the processing element 1011 and memory device 1008 may be located on a common substrate or on a same integrated circuit die. Alternatively, the components described herein may be integrated into one or more integrated circuits as would be appreciated by one having the benefit of this disclosure. The memory device 1008 may be any type of memory device, including a non-volatile memory, volatile memory, or the like. Although not separately illustrated the memory device may be one or more types of memory configured in various types of memory hierarchies.

The memory device 1008 may store physiological data 1024, such as current and past physiological measurements, as well as profile data 1030, including user profile data, bibliographic data, demographic data, and the like. The physiological data 1024, and in some cases the profile data 1030, may also include processed data regarding the measurements, such as statistical information regarding the measurements, as well as data derived from the measurements, such as predictive indicators, results, and/or recommendations.

In one example, the profile data 1030 may also include information connected to user profiles of the users that wear the electronic devices 1010, such as a gender of the user, an age of the user, a body weight or mass of the user, a health status of the user, a fitness level of the user, or a family health history of the user. In another example, the profile data 1030 can include occupational information of the users that wear the electronic devices 1010, such as a job type, a job title, whether the job is performed indoors or outdoors, a danger level of the job, and so forth. For example, the job types can include an elderly live-at-home job, an oil driller, a construction worker, a railroad worker, a coal mine worker, a job in confined spaces, a fireman, a construction worker, an outdoor worker, an office worker, a truck driver, a child, or a disabled individual.

In one example, the electronic device 1010 can receive the profile data 1030 via a touch screen device integrated into the electronic device 1010 or coupled to the electronic device 1010. In another example, the electronic device 1010 can receive the profile data 1030 via a communication port of the electronic device 1010. For example, the electronic device 1010 can receive profile data 1030 from another device via a wired communication connection (e.g., a universal serial bus) or via a wireless communication connection (e.g., a Bluetooth® communication technology).

The profile data 1030 may also be linked to various physiological data 1024 and Newtonian data 1028 and be tracked over time for the users. The profile data 1030 may also include baselines of physiological parameters for respective users. In one example, the baselines are of a heart rate, a blood pressure, bio-impedance, skin temperature, oxygen levels, hydration levels, electrolyte levels and so forth. When the baselines are included with the user profiles, the user profiles may be referred to as baseline profiles for the respective users.

The memory device 1008 may also store one or a combination of the environmental data 1026, the Newtonian data 1028, the profile data 1030, and the location data 1032. The Newtonian data 1028, environmental data 1026, or location data 1032 may be current and past measurements, as well predictive data for predictive modeling of activity levels, environmental levels, or locations. The memory device 1008 may store instructions of the sensor module 1016 and instructions and data related to the correlator 1013, the baseliner 1015 and the alerter 1017, which perform various operations described below.

In particular, the sensor module 1016 may perform operations to control the physiological sensors 1002, Newtonian sensors 1004, environmental sensors 1005, and location sensors 1006, such as when to turn them on and off, when to take a measurement, how many measurements to take, how often to perform measurements, etc. For example, the sensor module 1016 may be programmed to measure a set of physiological measurements according to a default pattern or other adaptive patterns to adjust when and how often to take certain types of measurements. The measurements may be stored as the physiological data 1024, the environment data 1026, and the Newtonian data 1028, location data 1032, and some of them may also be integrated as a part of the profile data 1030, as discussed.

In the depicted embodiment, the processing element 1007 (e.g., one or more processor cores, a digital signal processor, or the like) executes the instructions of the sensor module 1016 and those related to the correlator 1013, the baseliner 1015, the alerter 1017 and possibly other modules or routines. Alternatively, the operations of the sensor module 1016 and the correlator 1013, the baseliner 1015, and the alerter 1017 may be integrated into an operating system that is executed by the processor 1003. In one embodiment, the processing element 1011 measures a physiological measurement via the first sensor interface 1007. The processing element 1011 may measure an amount of activity of the electronic device 1010 via the second sensor interface 1009. The amount of activity could be movement or motion of the electronic device 1010 (e.g., by tracking location), as well as other measurements indicative of the activity level of a user, such as heart rate, body temperature, skin luminosity, or the like. The processing element 1011 measures an environmental measurement via the third sensor interface 1009. The processing element 1011 measures a location measurement via the fourth sensor interface 1010.

In one embodiment, the Newtonian sensors 1004 may include a hardware motion sensor to measure at least one of movement or motion of the electronic device 1010. The processing element 1011 may determine the amount of activity based the movement or motion of the electronic device 1010. The hardware motion sensor may be an accelerometer sensor, a gyroscope sensor, a magnetometer, a GPS sensor, a location sensor, a vibration sensor, a 3D accelerometer sensor, a force sensor, a pedometer, a strain gauge, a magnetometer, and a geomagnetic field sensor.

The processor 1003 may further execute instructions to facilitate operations of the electronic device 1010 that receive, store and analyze measurement data, environmental data, location data, and profile data. The indicator(s) 1018 may include one or more of a light, a display, a speaker, a vibrator, and a touch display, usable to alert the user to take actions in response to trending levels of: physiological parameters during or after physical activity and/or prepare for undertaking anticipated physical activity; environmental parameters; activity parameters, or location parameters.

In some embodiments, for example, the correlator 1013 may analyze measurement data to correlate physiological data, environmental data, activity data, location data, or user experienced feedback with a physiological parameter, environmental parameter, activity parameter, a location parameter, or user experienced feedback to predict a change in a level of the physiological parameter, environmental parameter, activity parameter, or a location parameter. In one embodiment, the user experienced feedback can be physiological or psychological symptoms experienced by the user. For example the physiological or psychological symptoms can include: headaches, dizziness, tiredness, mental fatigue, increased thirst, dry mouth, swollen tongue, physical weakness, confusion, sluggishness, and so forth.

Such prediction may enable timely and accurate recommendations to a user in terms of hydrating, adjusting effort levels or other specific actions to address a trend or a change in the physiological parameter, the environmental parameter, the activity parameter, or the location parameter. The recommendations may be displayed in the display 1080, sent via an alert through one of the indicator(s) 1018 or displayed in another device such as a smartphone or tablet or other computing device.

In another embodiment, the correlator 1013 may also track and analyze Newtonian data of the user related to physiological or determined parameters (such as heart rate, oxygenation, skin luminosity, hydration, and the like), related to location and type of activity (such as activity levels associated with being at the gym, riding a bike, attending class, working at a desk, sleeping, or driving in traffic, and the like) and/or related to scheduling information (such as appointments on a calendar, invites received from friends, or messages related to travel and/or activity plans, and the like). Through this analysis, the electronic device 1010 may track activity data over time, intelligently and continuously (or periodically) analyze all of this information, and alert the user through the indicator(s) 1018 to take a specific action at a proper time before a start of a safety event. The specific action may include to hydrate extra hours before physical activity and to eat at least two hours before any physical activity, or other such timing that may be general to most users, or customized to a training or nutrition routine of a specific user.

In another embodiment, the correlator 1013 can build an individualized profile for the user. The correlator 1013 can receive the individualized profile information from an input device of the electronic device 1010. For example, the correlator 1013 can receive the individualized profile information from a touch screen of the electronic device 1010. In another example, the correlator 1013 can receive the individualized profile information from a device in communication with the electronic device (such as via a USB port or using a Bluetooth® technology). In another embodiment, the electronic device 1010 can include a memory that stores the individualized profile information for the user.

The individualized profile can include physiological information associated with the user. For example, the physiological information can include an average heart rate of the user, an age of the user, a health level of the user, and so forth. The individualized profile can also include information associated with a location or environment that the user is located. For example, the individualized profile can include: humidity level information, such as when the user is located in a dry climate or in a humid climate; altitude level information, such as when the user is located at a relatively high altitude or a relatively low altitude; seasonal information, such as if it is winter where the user is located or summer. The correlator 1013 can also determine an environmental effect on the user for the location where the user is located at. For example, if the user is located at their home that is at a high altitude with a dry climate and it is a winter season, the correlator 1013 can determine that the user is acclimated to high altitudes, dry climates, and the winter season. The correlator 1013 can also update the user profile when the user changes location. For example, when the user leaves their home location and goes on a vacation to a location that is at a low altitude, a humid climate, and it is a summer season, the correlator 1013 can determine that the user is not acclimated to the low altitude, humid climate, and summer season.

In one embodiment, the electronic device 1010 can alert the user of the changes to the individualized profile. In another embodiment, the electronic device 1010 can alert the user of the changes to effects associated with the changes to the individualized profile. For example, the electronic device 1010 can access a table of predetermining effects of the user changing their user profile. In one example, the table can indicate that when the user switches from a low altitude to a high altitude location, the user may experience altitude sickness. In another example, the table can indicate that when the user switches from a dry climate to a humid climate location, an ability of the user's body to cool itself down when an ambient temperature is relatively high. In another embodiment, the table can indicate when the current user profile indicates safety risks or physiological performance changes.

In another embodiment, the individualized profile can also include information associated with clothing or apparel worn by the user of the electronic device 1010. For example, the individualized profile can indicate that a user may wear different types of apparel for different environments including: a thickness of fabric; a type of a fabric, such as wool or cotton; a number of clothes layers worn by the client; accessories worn by the client, such as hard hats, steeled toed shoes, safety goggles, safety belts, and so forth; and gender types of apparel, such as women and men's apparel. In one example, the correlator can adjust measurement information or measurement results based on the different types of clothing or apparel. For example, the correlator 1013 can determine that the user is a firefighter and is wearing multiple layers of clothing to protect against fire. In this example, the correlator 1013 can determine that a cause of a hydration level of the user decreasing is the multiple layers of clothing cause the firefighter to sweat more and lose more fluid than a typical number of layers of clothing worn by the user.

In one embodiment, the alerter 1017 may decide the most appropriate timing and mode of alert, whether through one of the indicator(s) 1018, the display 1080 or another device such as a smartphone, tablet or the like. The type of indicator used to alert the user may also be customized to or by the user.

In one embodiment, the correlator 1013 may determine a correlation between different data points or data sets of the input data (such as data collected from different sensors, devices, or obtained from the cloud or online). The correlator 1013 may determine different types of correlations of the data points or data sets. In one example, the correlator 1013 may execute a Pearson product moment correlation coefficient algorithm to measure the extent to which two variables of input data may be related. In another example, the correlator 1013 may determine relations between variables of input data based on a similarity of rankings of different data points. In another example, the correlator 1013 may use multiple regression algorithms to determine a correlation between a data set or a data point that may be defined as a dependent variable and one or more other data sets or other data points defined as independent variables. In another example, the correlator 1013 may determine a correlation between different categories or information types in the input data.

In further examples, when the correlator 1013 determines a correlation between the different data points or data sets, the correlator 1013 may use the correlation information to predict when a first event or condition may occur based on a second event or condition occurring. In another example, when the correlator 1013 determines a correlation between the different data points or data sets, the correlator 1013 may use the correlation information to determine a safety event. As discussed in the preceding paragraphs, a safety event can be an event that negatively impacts a user's safety or health. For example, a safety event can be: a fall event where a user falls down, such as an elderly person falling down; an unconscious event where a user becomes unconscious, such as a farm worker losing consciousness due to heat stroke; a cognitive ability reduction event where a user's cognitive ability is reduced, such as when a user becomes confused or disoriented from low blood pressure or low blood oxygenation levels; a fatigue event where a user becomes fatigued, such as when a user is fatigued from dehydration; a sickness event where a user becomes physically sick; and so forth. In another example, when the correlator 1013 determines a correlation between the different data points or data sets, the correlator 1013 may use the correlation information to determine a cause of a condition and/or event, such as a safety event.

Additionally, or alternatively, the correlator 1013 may determine a correlation between physiological data 1024, environmental data 1026, Newtonian data 1028, profile data 1030, and location data 1032. For example, the input data may include hydration level data (physiological data) and ambient temperature data (environmental data). In this example, the correlator 1013 may identify a correlation between an increase in the ambient temperature, a decrease in a hydration level of a user, and a heat stroke safety event. The correlator 1013 may identify the correlation between the ambient temperature, the hydration level, and the heat stroke by using a regression algorithm with the heat stroke as an independent variable and the ambient temperature and the hydration level as dependent variables. When the correlator 1013 has identified the correlation between the heat stroke, the ambient temperature, and the hydration level, the correlator 1013 may predict a heat stroke safety event based on a change in a hydration level of a user or a rate of change of a hydration level of a user and a change in the ambient temperature or a rate of change in the ambient temperature.

Additionally, or alternatively, the correlator 1013 may determine a correlation between a fatigue event, an altitude level, and an oxygenation level of a user. For example, the correlator 1013 may determine a correlation between an increase in the altitude level, a decrease in the oxygenation level of the user, and an increase in a fatigue event. When the correlator 1013 determines the correlation between the altitude level, the oxygenation level, and the fatigue event, the correlator 1013 may predict an increase or decrease in a probability of a safety event based on a change in the oxygenation level of the user and the altitude level at which the user is currently at. In one example, the correlator 1013 can use the individualized profile information (as discussed in the preceding paragraphs) of the user to determine the predicted increase or decrease in the probability of a safety event. For example, the correlator 1013 can determine a change in altitude level of the user from a relatively low altitude to a relatively high altitude. The correlator 1013 can use the individualized profile information to determine that the user is acclimated to the relatively high altitude (such as if they live at a high altitude) and adjust the predicted increase or decrease in the probability of a safety event for the change in altitude in view of the individualized profile information. For example, the correlator 1013 can predict that the change from the low altitude to the high altitude will not increase or decrease the probability of the safety event occurring.

In a further example, the correlator 1013 may identify a correlation between location information and physiological data of a user. For example, the correlator 1013 may determine a location of a user for at a period of time, such as by using GPS sensor data or triangulation sensor data. In this example, the correlator 1013 may receive physiological measurement data (such as heart rate measurement data, optical spectroscopy data, hydration level measurement data, blood pressure measurement data, and so forth). The correlator 1013 may correlate the location of the user with the physiological measurement data to increase an accuracy of data analysis, a diagnosis, or result data and/or provide additional details regarding a cause of a safety event.

In one example, the correlator 1013 may determine that a user is at work in an office location. When the correlator 1013 detects an increase in a heart rate or a blood pressure of a user, the correlator 1013 may correlate heart rate or blood pressure data and the location information to determine a cause of the cognitive ability reduction event. For example, when a heart rate or blood pressure of an individual increases while at a work in an office, the correlator 1013 may determine that the heart rate or blood pressure increase may be due to psychological causes (such as stress) rather than physiological causes (such as exercising or working out) because the user is at a location where an individual is not likely to physically exert himself or herself.

In another example, the correlator 1013 may determine an occupation of the user, such as by using the profile data 1030. In one embodiment, the correlator 1013 can determinate that the occupation of the user is a higher risk occupation (e.g., a statistically more dangerous occupation). For example, the correlator 1013 can access a database or list (stored at the memory device 1008 or externally) that includes information associated with an occupation, such as a danger level or a safety event likelihood. When the correlator 1013 detects that the occupation of the user is a higher risk occupation (e.g., an occupation with a risk level that exceeds a threshold value), the correlator 1013 may correlate heart rate data, blood pressure data, hydration level data, with the occupational information to determine a cause of a safety event. For example, when a heart rate and blood pressure of an individual increases and a hydration level of the individual decreases while the individual is working at an oil refinery or on a farm, the correlator 1013 may determine that the heart rate or blood pressure increase may be due to physiological influences of the occupation (such as strenuous labor or no breaks) rather than psychological causes (such as stress) because the occupation where the individual is working at is likely to include physical exertion.

In a further example, the correlator 1013 may use multiple regression algorithms to determine a correlation between multiple data points or data sets and safety events. For example, the correlator 1013 may receive heart rate data, skin temperature, bio-impedance data, skin luminosity and hydration level data of a user. In this example, the correlator 1013 may determine a correlation between these types of physiological data and a dehydration event of the individual. For example, the physiological data could be from optical spectroscopy (skin luminosity) and/or bio-impedance data. The correlator 1013 may then determine that as the bio-impedance of an individual increases and skin luminosity decreases, a probability of a dehydration event occurring increases.

Additionally, or alternatively, the correlator 1013 may filter out a correlation determination (e.g., a determination that data points or data sets and safety events may be correlated) when a correlation level is below a threshold level. For example, when the correlator 1013 determines that there may be a 30 percent correlation between a skin temperature or a bio-impedance level of an individual and a fall event, the correlator 1013 may filter out or disregard the correlation information when determining a cause of the fall event. In another example, the correlator 1013 can use a learning algorithm or machine learning to determine when to filter out a correlation determination. For example, at a first instance of a fall, there may be a 30 percent correlation between a skin temperature or a bio-impedance level of an individual and a fall event The correlator 1013 can monitor multiple fall events and use machine learning to determine that the initial 30 percent correlation is actually a 60 percent correlation and adjust the filter to not filter out the correlation between the skin temperature or the bio-impedance level of an individual and a fall event or assign the correlation of the skin temperature or the bio-impedance level of an individual and a fall event a different weight.

Additionally, or alternatively, the correlator 1013 may filter out the correlation determination based on a schedule of an individual. For example, when the correlator 1013 determines that an individual is taking a lunch break, off of work, or sleeping, the correlator 1013 may filter out safety events that are associated with the occupation of the user, e.g., the correlator 1013 can filter out false positives.

Additionally, or alternatively, the correlator 1013 may discount or weight a correlation determination based on the correlation level of the correlation determination. For example, when the correlator 1013 determines that there may only be a 30 percent correlation between an occupation of an individual and a hydration level of an individual, the correlator 1013 may discount or assign a lower weight to the correlation determination (relative to a higher correlation percentage such as 90 percent) when determining a cause of a safety event.

Additionally, or alternatively, the correlator 1013 may assign weights to different factors, such as: physiological data 1024 (e.g., different types or qualities of physiological parameters), environmental data 1026 (e.g., different types or quality of environmental parameters), Newtonian data 1028 (e.g., different types or quality of Newtonian parameters), profile data 1030, location data 1032 (e.g., different types or quality of location parameters), a time of day, and so forth. In one example, the correlator 1013 may assign a first weight to hydration level data of an individual and a second weight to profile data of an individual when determining a probability of a safety event for an individual. In this example, when determining the safety event probability, the correlator 1013 may assign a higher weight to the hydration level data relative to the profile data, for example.

The correlator 1013 may additionally, or alternatively, use predetermined weights for the physiological data 1024, environmental data 1026, Newtonian data 1028, profile data 1030, and location data 1032. In another example, the correlator 1013 may receive user-defined or predefined weights from an input device indicating the weights for the different physiological and/or environmental data. In another example, the correlator 1013 may determine the weights to assign to the physiological data 1024, environmental data 1026, Newtonian data 1028, profile data 1030, and location data 1032 based on correlation levels of the physiological data 1024, environmental data 1026, Newtonian data 1028, profile data 1030, and location data 1032. For example, when a correlation level between a safety event and a heart rate of an individual may be relatively low over a threshold period of time and/or under a threshold number of different conditions, the correlator 1013 may assign a low weight to heart rate data when determining a cause of a safety event.

In one example, the correlator 1013 may assign different weights to one or more of the physiological data 1024, environmental data 1026, Newtonian data 1028, profile data 1030, and location data 1032 based on other physiological data 1024, environmental data 1026, Newtonian data 1028, profile data 1030, and location data 1032. For example, based on a location of an individual, the correlator 1013 may assign a first weight to environmental data 1026 and a second weight to profile data 1030. In another example, the correlator 1013 may assign weights to different safety events.

Additionally, or alternatively, the correlator 1013 may use environmental data 1026 or location data 1032 to determine a cause of a safety event. For example, when a user is located at a fitness facility working out, the correlator 1013 may increase a weight for a physical exertion-related safety event occurring because of in physical exertion of a user (such as an increase in a heart rate or decrease in a hydration level of a user). In another example, when a user is located at home in bed resting or sleeping, the correlator 1013 may correlate a location of the user with safety events of the user. In this example, the correlator 1013 may determine that a decrease in the probability of a safety event occurring due to an individual being is located in their bedroom for a threshold period of time (e.g., a safer environment).

In one embodiment, the correlator 1013 can determine a weighting of measurement information or physiological information using medical evaluation information. In one example, the medical evaluation information includes medical evaluation information of the user, such as a medical physical. The medical evaluation information can include: medical history and health history information, such as whether the user is a smoker or a non-smoker; a user's blood pressure information; hereditary diseases information; a user's sexual health information; a user's dietary information, a user's exercise routine information, such as how often the user exercises; a user's heart or lung examine information; and so forth. In one example, the correlator 1013 can use the medical evaluation information to set initial weight for different data types. The correlator can update or adjust the weights for the different data types using machine learning. For example, the physiological data 1024, environmental data 1026, and Newtonian data 1028 is assigned a first set of weights based on the medical evaluation information. As the electronic device 1010 uses the sensors to collect the physiological data 1024, environmental data 1026, and the Newtonian data 1028, the correlator 1013 can use the physiological data 1024, the environmental data 1026, and the Newtonian data 1028 to customize the weighting of the measurement information or physiological information to the individual. For example, the correlator 1013 can receive medical evaluation information for the user input device of the electronic device 1010 using an input device of the electronic device 1010.

The correlator 1013 may track, sort and/or filter input data. The input data may include: user schedule information, such as a daily schedule of the user; survey information, such as information received from surveys of individuals; research information, such as clinical research information or academic research information associated with one or more safety events of the electronic device; and so forth.

The correlator 1013 may use location-based tracking and/or scheduling information of the user in determining an expected or probable safety event occurring. For example, when a user is a member of a sports team, the user's schedule may include practice schedule information and/or game schedule information. In this example, the correlator 1013 may use the schedule information to anticipate that the user may be participating in physical activity and increase a probability that a safety event may occur.

The correlator 1013 may use timer information determining an expected or probable safety event occurring. For example, the correlator can monitor how long it may have been since a user took a break or consumed water. In this example, as the length of time increase between a break or water consumption, the probability that a safety event may occur increases. In another example, the correlator can use the timer information to periodically request a response from the user. For example, when a safety event has not occurred within a threshold amount of time that would trigger a user response, the electronic device can request a user response from the user when the threshold amount of time has been exceeded.

In another example, the correlator 1013 can have a work mode (the user is at work) and a home mode (the user is at home), where a type of safety event that the electronic device monitors for and/or a probability of a safety event occurring can increase or decrease when switching between the work mode and the home mode. For example, when the user has a high-risk occupation, the correlator 1013 can monitor for safety events related to the high-risk occupation when the correlator is in a work mode and switch to monitoring for safety events related to low risk activities when the correlator is in a home mode.

In another example, the correlator 1013 may use the scheduling information in correlation with a location of the user to determine an expected or probable safety event. For example, the scheduling information may indicate that the user may be scheduled to attend a lecture at a physical fitness facility and the correlator 1013 may adjust the types or probabilities of a safety event occurring in view of the scheduling information. In this example, while the correlator 1013 may typically increase a probability of a safety event occurring for the user in anticipation of physical activity based on the location information (e.g., the physical fitness facility), the correlator 1013 may adjust the adjust the types or probabilities of a safety event occurring in view of the scheduling information that the user may be attending a lecture rather than working out.

Additionally, or alternatively, the correlator 1013 may track and update activity levels of users and correlate these levels with safety events over time. For example, the GPS sensor of the electronic device 110 may indicate that the user usually works out at the gym on Monday, Wednesday and Friday at 7 a.m. and goes on a long bike ride on Saturday, usually starting about 8:30 a.m. Although these activities may not be available within the scheduling information or data of the electronic device 110 (or other tethered device), the correlator 1013 may execute machine learning to add to a user's activity data these events that normally occur.

The electronic device 1010 may store historical or previous safety event information of the user. In one example, the correlator 1013 may store the historical information on the memory device 1008 of the electronic device 110. In another example, the correlator 1013 may use the communication device 170 (FIG. 1), the communication unit 570 (FIG. 5), or the communication interface 1090 to store the safety event information on a memory device coupled to or in communication with the electronic device, such as a cloud-based storage device or a memory device of another computing device. In another example, the correlator 1013 may be part of a cloud-based system or the other computing device.

The correlator 1018 may filter and/or sort safety event information. In one example, the correlator 1018 may receive a filter or sort command from the electronic device or an input device to filter and/or sort the safety event information. In another example, the filter or sort command may include filter parameters and/or sort parameters. The filter parameters and/or sort parameters may include different types of safety events.

In another example, the correlator 1013 may sort and/or filter the input data based on a trending of safety events. For example, the correlator 1013 may sort safety events that may be trending in an increasing direction or a decreasing direction and may sort the safety events based on the trending. In this example, different safety events for a user may be trending in different directions, such as a dehydration events of a user may be increasing in trending and fall events may be stable or stagnant.

In one example, the correlator 1013 may sort or filter the safety events data on a group level. In another example, the correlator 1013 may sort or filter the safety events on an individual level.

In another embodiment, the baseliner 1015 may receive profile information from a new user to include any or a combination of gender, age, weight, health, fitness level, and family health histories. The health and fitness levels of the user may be based at least in part on physiological measurements received from the physiological sensor(s) 1002 and the activity data received from the Newtonian sensors 1004. The baseliner 1015 may then identify, from a plurality of baseline profiles of other users (e.g., a group of users), a baseline profile that is most similar to the user profile based on a correlation between the user profile information and baseline profile information. The baseline profiles can include baseline information of a probability of safety events occurring for a user. The user profiles can include information of the types of safety event that may be probable to occur for the user.

The baseliner 1015 may then be able to set a baseline against which to judge safety events. In an alternate embodiment, the baseline profile that is most similar to the user profile is identified from an aggregated baseline profile for a plurality of individuals corresponding to the plurality of baseline profiles. Alternatively, or additionally, the most similar profiles may look at safety events that occur for the individual as compared to the group. For example, the user may be most similar to another individual because they both react physiologically similarly to hot temperatures outside. In another example, the user may have a similar dehydration profile to the most similar profile, meaning, when the user works out the user may reach a dehydration level at a certain point in time that substantially matches the timing of the most-similar profile.

The electronic device 110 may further receive survey information and/or research information from an input device with which to build or add to the user and/or baseline profiles. For example, the electronic device 110 may receive survey information that includes: gender information, age information, physical weight information, general health information, family information, fitness level information, and so forth. In one example, the correlator 1013 may determine a correlation between the survey information and user input data. For example, the correlator 1013 may correlate the age, weight, fitness level, and general health level of a user with survey information from other individuals to determine a correlation between the survey information for the individual and the other individuals. In this example, the baseliner 1015 may set a baseline for a measurement of the electronic device 110 for the individual based on baselines for the other individuals with the same or similar survey information.

In another example, the correlator 1013 may correlate the user information with research information (such as research papers, clinical studies, and so forth). For example, the electronic device may retrieve research information related to a physiological parameter, the correlator 1013 may then correlate the research information with safety events for the user to generate a research correlation. The baseliner 1015 may then adjust the baseline set for the user related to the safety events in response to the research correlation.

The correlator 1013 can store safety event information in a safety event database 1012. In one embodiment, the correlator 1013 can determine parameters associated with a safety event (safety parameters). The safety parameters can include threshold values for measurements or data values, such as physiological sensor measurements, environmental sensor measurements, Newtonian sensor measurements, location sensor measurements, or profile data 1030. The correlator 1013 can store the safety event and the associated safety parameters in the safety event database 1012. For example, the correlator 1013 can determine that parameters for a heat stroke event can be a skin temperature above a 100-degree temperature, blood pressure above 150 systolic, and a bio-impedance level above 15000 ohms (e.g., a dehydration level threshold). In this example, the correlator 1013 can determine these parameters can store the safety event with the associated parameters in the safety event database 1012. In another example, the store predetermined safety events with the associated parameters. In another example, the safety event database 1012 can receive the safety events and the associated parameters from another device or server 1094.

The preceding examples are intended for purposes of illustration and are not intended to be limiting. The correlator 1013 may identify a correlation between various data points, data sets, data types, and/or safety events. After having a correlation that informs, for example, a heat stroke event, the hydration level, and/or oxygenation level of the user, and further in consideration of a present activity level of the user, the alerter 1017 may alert the user at the proper time when to hydrate or how to moderate activity levels to avoid or minimize a safety event. The alerter 1017 may alert the user, a third party (such as a caregiver, a supervisor, or a coach), or a combination thereof.

Figure 11:
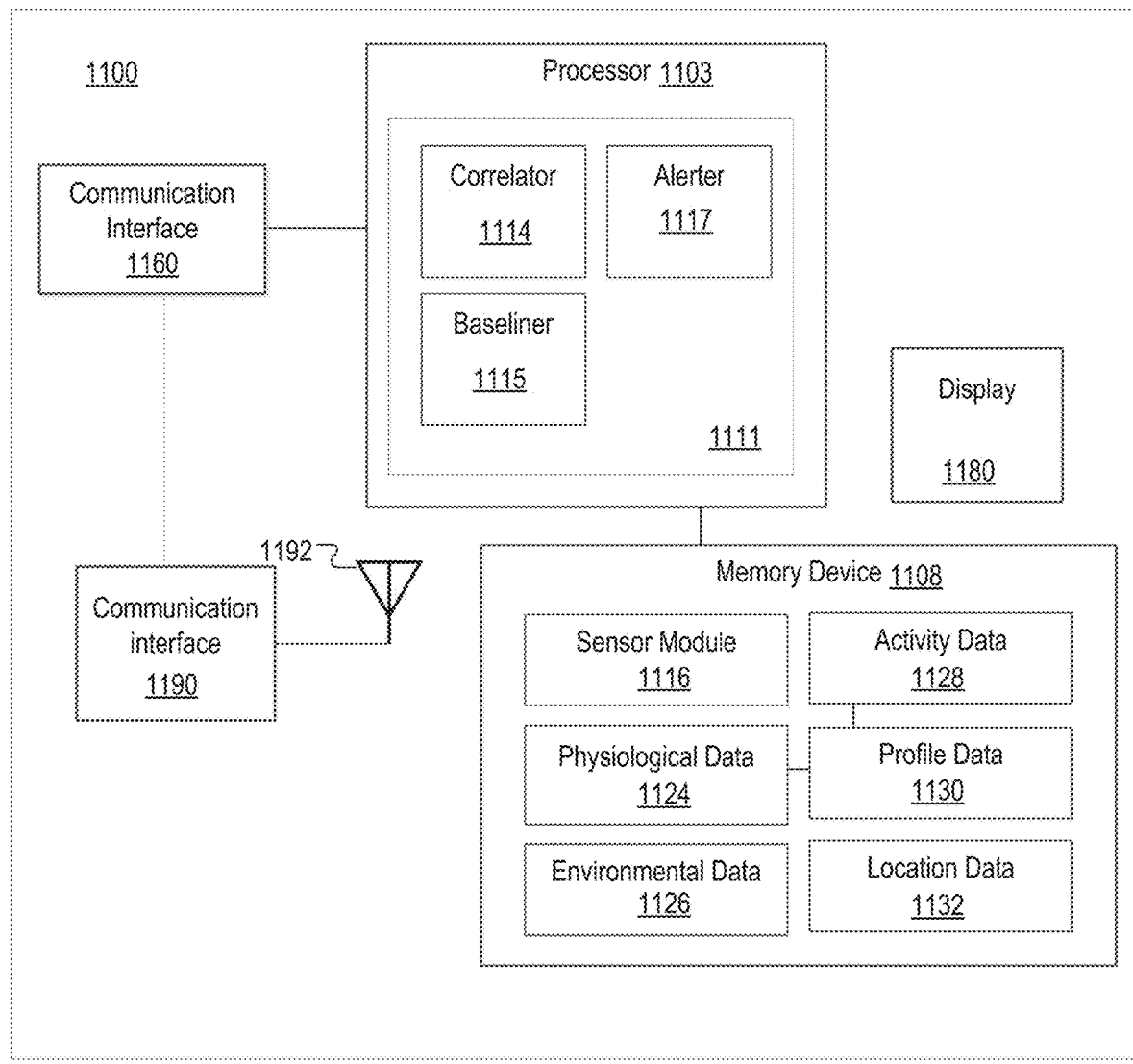
FIG. 11 is a block diagram of a networked device that communicates with an electronic device according to one embodiment.

FIG. 11 is a block diagram of a networked device 1100 that communicates with an electronic device according to one embodiment. In one embodiment, the network device 1100 may be a hub device (or base station), an external electronic device 590 (FIG. 5), a computing device 620 or 720 (FIGS. 6 and 7), and so forth. The network device 1100 can communicate with other wireless devices such as the electronic device 110 (FIG. 1), the electronic device 220 (FIG. 2), the electronic device 410 (FIG. 4), the electronic device 510 (FIG. 5), the electronic device 610 (FIG. 6), the electronic device 710 (FIG. 7), the electronic device 910 (FIG. 9), or the electronic device 1010 (FIG. 10). In another embodiment, the network device 1100 may be a server. As such, the networked device 1100 may include a communication interface 1160 which with to communicate over a communications network. In some cases, the communication may be with the help of a communication interface 1190 (such as an RF circuit) and an antenna 1192, to communicate wirelessly, e.g., as may be used by the hub (or a base station or a switch or the like that) at least in some implementations.

In one embodiment, the components of the networked device 1100 may be the same or similar to the components discussed in the preceding paragraphs with reference to the electronic device 1010 of FIG. 10, with the exception of the sensors 1002, 1004, 1005, and 1006 and indicator(s) 1018. Sensor data may be sent from the electronic devices to the networked device over the network and through the communications interface 1160. Furthermore, any alerts or information for the user may be sent back to the electronic device to initiate one of the indicator(s) 1018 or provide information to the user through the display 1080. The functions and capabilities of the electronic device 1010 of FIG. 10 may generally be replicated or enhanced by the functions and capabilities of the networked device 1100 in terms of processing power, data analytics, performing correlations, predictions, analyzing and setting baselines, and other algorithmic work.

Accordingly, in one embodiment, the network device 1100 may also include, without limitation, a processor 1103, a memory device 1108, and a display 1180. The processor 1103 may include a processing logic or a processing element 1111 that may have a correlator 1114, a baseliner 1115 and an alerter 1117. The memory device may include a sensor module 1116, physiological data 1124, environmental data 1126, activity data 1128, profile data 1130, and location data 1132 of and related to the users.

In one embodiment, the sensors 1002, 1004, 1005, and 1006 of the electronic device 1010 may generate measurements, information and data that is stored in the memory device 1008 of the electronic device 1010 as discussed herein. In another embodiment, the electronic device 1010 may send this data and information to the networked device 1100 to be stored as the physiological data 1124, the environmental data 1126, the activity data 1128, the profile data 1130, and/or the location data 1132. The user profiles and, optionally, baseline profiles of the users may also be stored with the profile data 1130. And, as discussed herein, historical information may be stored by the networked device 1100 that may help the networked device 1100 with machine learning and to perform more intense processing and statistical analysis that may be required to implement the processes and strategies disclosed herein.

For example, the processing element 1111 may function largely the same as the processing element 1011 discussed with reference to the electronic device 1010 of FIG. 10, but with perhaps greater processing power and speed. In other words, the correlator 1114 may function similarly to the correlator 1013 upon receipt of the physiological data, environmental data, activity data, profile data, and location data from the electronic device 110 and/or from other sources. Those other sources may include cloud or internet servers that provide weather, altitude, geographic and location information, calendar and scheduling information, and other such information or data. Some of these sources may include other devices of the user such as a smartphone, tablet, a scale, a refractometer, a plasma osmolality device or other computing device that may or may not be tethered to the electronic device 1010, in alternative embodiments.

Furthermore, the baseliner 1115 may function similarly to the baseliner 1015 of the electronic device 1010 of FIG. 10 based on sensor data and other information received from the electronic device 1010 or the other sources. Additionally, the alerter 1117 may function similarly to the alerter 1017 of the electronic device 1010 of FIG. 10, based on sensor data and other information received from the electronic device 1010 or other sources.

In one embodiment, the electronic device 1010 may generate additional physiological data, environmental data, activity data, profile data, and location data from on-going measurements. The user may also enter new information that may change the user's profile, such as a new age or job type, and this information may also be sent by the electronic device 1010 to the networked device 1100. When a baseline is set by the electronic device 1010 for a user as discussed in the preceding paragraphs, this baseline may also be sent to the networked device 1100 where baselines for all users may be kept up to date, for tracking those users as well as providing data from which an initial baseline may be set for a physiological parameter of a newly added user. Furthermore, or alternatively, the baseline may be set by the baseliner 1115 of the networked device 1100 and sent to the electronic device of the corresponding user against which new physiological measurements may be compared and/or correlated locally by the electronic device.

Furthermore, any updates to a user profile, new physiological and/or environmental measurements may be sent to the networked device 1100 by the electronic device 1010. As this type of information is updated, the networked device 1100 may also update the baseline and/or baseline profiles of the users as disclosed herein. Any such updated baseline may be sent to the corresponding electronic device 1010 of the correct user, which electronic device 1010 may then update the baseline for that user locally.

In one example, the electronic device can take physiological measurements of an individual. In another example, the electronic device can take environmental measurements of an environment adjacent the individual. In another example, the electronic device can receive environmental information or measurements from other devices. For example, the electronic device can receive ambient temperature measurements and humidity measurements from the other device. In one example, the electronic device can use the measurements from the other device to verify a validity of measurements taken using sensors of the electronic device. In another example, the electronic device can incorporate the environmental information or measurements with measurements taken by the electronic device to be used for a statistical analysis.

The electronic device can perform the statistical analysis on the physiological measurements and/or environmental measurements to detect measurement trend shifts to determine a hydration condition of a user. The electronic device can perform a statistical analysis on the physiological measurements and/or environmental measurements to detect symptoms indicative of a hydration condition of a user. The electronic device can identify trend changes, erroneous or outlying measurement data, and sensor shifts. The electronic device can detect trend shifts by computation of a slope in the trending of measurement data to determine a hydration condition of the user.

The electronic device can use the trend analysis to detect changes in trend parameters without user input. When a change in a hydration condition of a user or dehydration symptoms is detected, the electronic device can generate a recommendation based on the change in the hydration condition or the dehydration symptoms. In one example, the electronic device can use a sensory device to communicate the recommendation. In another example, the electronic device can use a communication device to send the recommendation to another electronic device. One advantage of the electronic device using the trend analysis can be to non-invasively monitor a user in the background (e.g., without need of user input) and provide an alert or recommendation to a user when there is a change in a hydration condition of a user or dehydration symptoms are detected.

Trend parameters can be set to designate when a change in a hydration condition of a user or dehydration symptoms are detected for measurement data from a sensor of the electronic device. In one example, the electronic device can initially use raw measurement data for analysis. The electronic device can filter or remove outlining or rogue data points from the raw data during a detection analysis. The electronic device can also detect abnormal or sudden shifts and changes at recent data point different trend parameter. The electronic device can evaluate changes in trend parameters, according to predetermined relationships, in order to filter out spurious or erroneous data and provide accurate recommendations for trend analysis. In another embodiment, the trend parameter is a coefficient of variation indicating an amount of variability relative to a reference value, such as a baseline value defined for a user.

The trend parameters can be in reference to a baseline (such as a parametric baseline). The baseline can be derived or generated (e.g., empirically derived or generated) using dehydration or body fluid models. The electronic device can use multiple trend parameters to filter measurement data. The trend parameters can be used as markers different hydration condition indicators. For example, a first trend parameter can be set to indicate a change in an impedance level of a user and a second trend parameter can be set to indicate a change in an optical measurement of a user.

Figure 12:
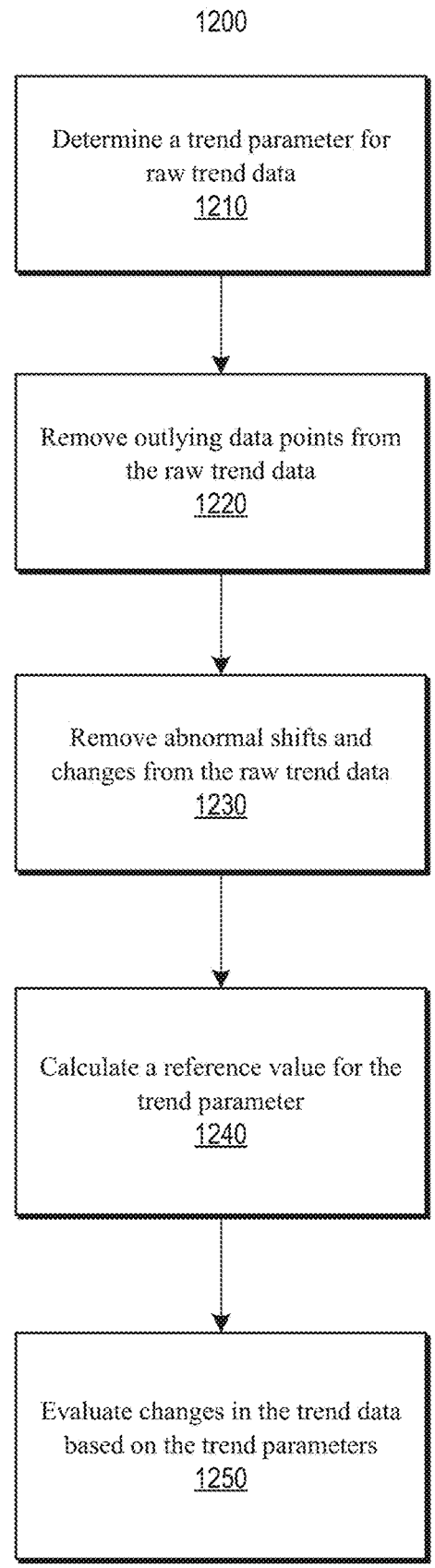
FIG. 12 illustrates a diagram of a method for trend analysis according to one embodiment.

FIG. 12 illustrates a diagram of a method 1200 for trend analysis according to one embodiment. The method 1200 may at least partially be performed by processing logic that includes hardware (e.g., circuitry, dedicated logic, programmable logic, microcode, etc.), software (e.g., instructions executed by a processing device), firmware or a combination thereof. The method 1200 may be performed, at least in part, by processing logic of the electronic device 110 (FIG. 1), the electronic device 220 (FIG. 2), the electronic device 410 (FIG. 4), the electronic device 510 (FIG. 5), the electronic device 610 (FIG. 6), the electronic device 710 (FIG. 7), the electronic device 910 (FIG. 9), or the electronic device 1010 (FIG. 10).

Referring to FIG. 12, the method 1200 begins with determining a trend parameter for raw trend data (1210). In one embodiment, a trend parameter can be a measurement parameter that is sensitive to changes in a hydration condition. In one example, the processing logic can use a cycle to determine which parameters, such as impedance, optical measurements, skin temperature, etc., of a user are sensitive to changes in the hydration condition of a user. When the selected trend parameters enable differentiation between high and low hydration conditions, the electronic device can isolate faults or circumstance that may cause changes in the hydration condition. For example, a change in ambient temperature, humidity levels, user exertion levels, health conditions, and so forth can cause an increase or decrease in trending data. In one example, trend changes may not be used in an overall trend analysis unless corresponding changes are seen in related trend parameters. In this example, only viable symptoms are provided. When viable symptoms are detected, specific recommendations can be generated.

The method can include removing outlying data points from the raw trend data (1220). For example, the outlying data points can be removed from the raw trend data so that the outlying data points are not included in the trend analysis. The method can include removing abnormal shifts and changes from the raw trend data (1230). The method can include calculating a reference value for the trend parameter (1240). The method can include evaluated changes in the trend data based on the trend parameter (1250).

Figure 13:
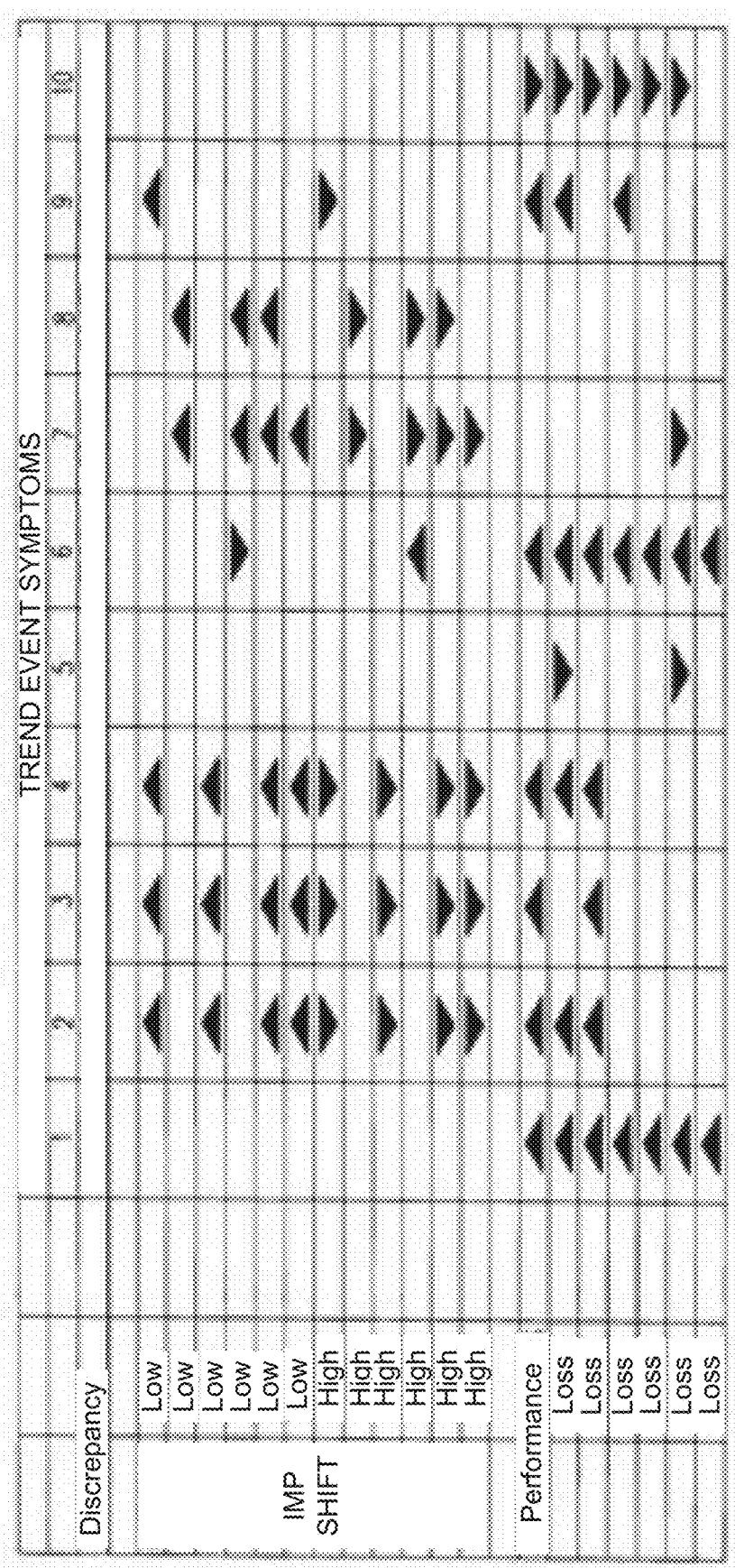
FIG. 13 illustrates an example of a trend fault template for generation of trend alarms and their corresponding recommendations according to one embodiment.
Figure 14:
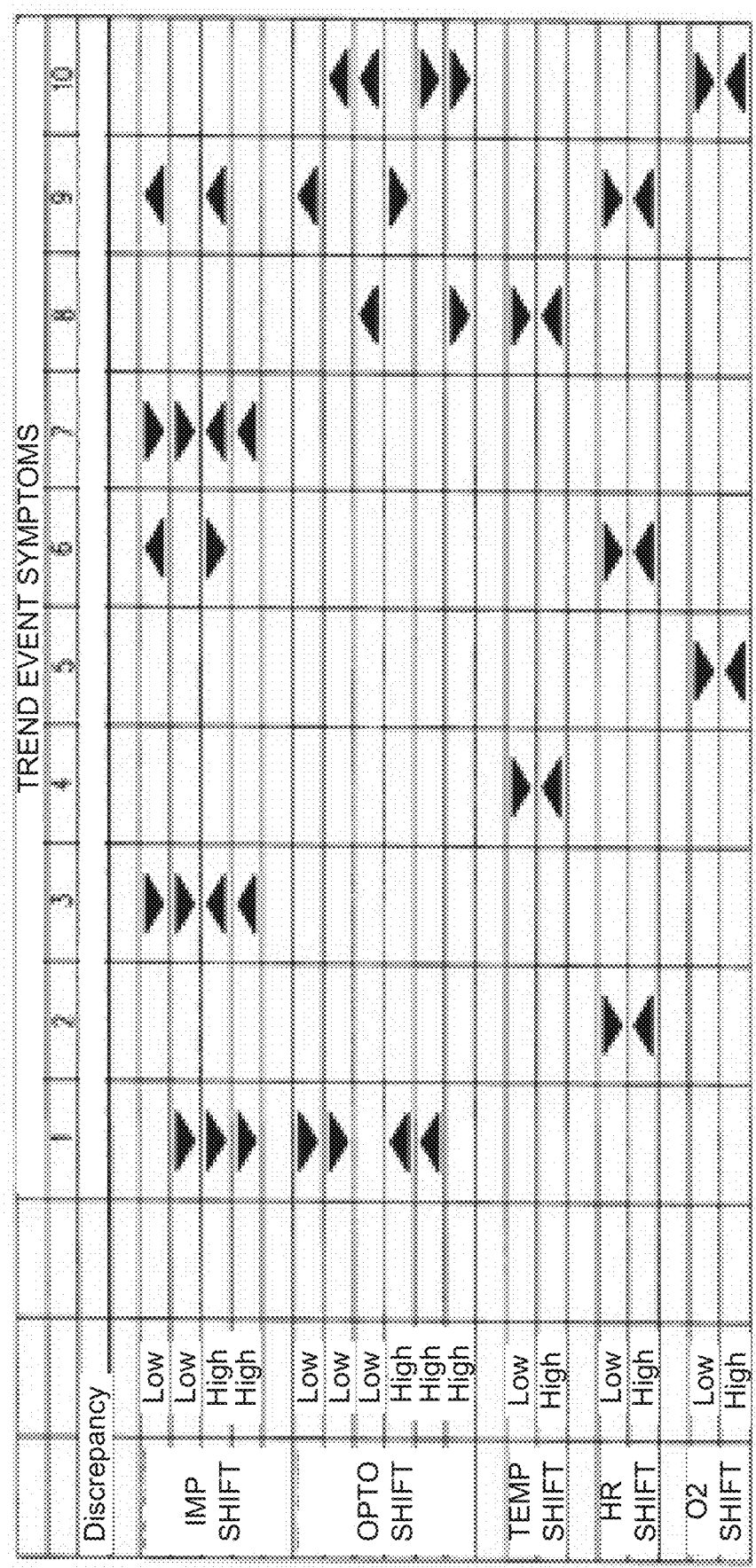
FIG. 14 illustrates another example of a trend fault template for generation of trend alarms and their corresponding recommendations according to one embodiment.

FIG. 13 illustrates an example of a trend fault template for the generation of trend alarms and their corresponding recommendations according to one embodiment. FIG. 14 illustrates another example of a trend fault template for the generation of trend alarms and their corresponding recommendations according to one embodiment. On the left side of the templates in FIGS. 13 and 14 are discrepancies correlating to the various trend event parameters, including core temperature, skin temperature, impedance levels, spectroscopy measurements, sweat rate, etc. In one embodiment an actual trend signature indicating which shifts are up or down is compared to the fault templates of FIGS. 13 and 14.

The resultant set of parameters is then scored against all possible causes, by applying varying degrees of importance to the match between template parameters and actual parameters. The electronic device can evaluate the score to determine a most probable cause of dehydration. The electronic device can perform the trend analysis to analyze trend data and evaluate an overall hydration condition of a user. One advantage of the electronic device using the trend analysis is to reliably detect and annunciate changes and shifts in trend data that are probably hydration condition changes, and suppresses false or spurious shifts in trend data.

In one embodiment, fault templates or parametric filtering are implemented to detect shifts in trend data and to determine recommendations based on those changes. In another embodiment, multiple trend parameters can be used to enhance classification of detected trend shifts into random or spurious events, sensor or signal shifts, or actual hydration condition changes.

Various embodiments have been shown and described herein to provide examples. However, numerous variations, changes, and substitutions can occur. For example, the control charts (FIGS. 13 and 14) may be replaced with any statistical analysis which checks for variation beyond a certain value from the mean. In another example, the electronic device can analyze trend data to determine when a time ordered slope of trend data exceeds a threshold. In another example, a magnitude of changes in one or more parameters could also be included as a factor in recommendation generation.

FIGS. 15-25 illustrate impedance measurement trending under various conditions. FIG. 15A illustrates an impedance trending graph 1500 of measurement data taken using a sensor of an electronic device during a high activity phase 1520 and a low activity phase 1540 of a user of the electronic device according to one embodiment. The impedance measurement trending 1500 can have a variety of measurement phases, including: an acclimation phase 1510; the high activity phase 1520; a transition phase 1530; the low activity phase 1540; and a removed device phase 1550. The impedance measurement trending may include a phase range, such as a high activity phase range 1560 when the user is engaging in a relatively high physical activity or a low phase range 1570 when the user is engaging in the relatively low physical activity. The processing logic of the electronic device can identify a measurement phase for trending information. In another example, a phase range may be a coefficient of variation from a reference value 1580. The coefficient of variation may measure of range or spread that indicates an amount of variability relative to the reference value 1580. For example, the coefficient of variation may be measured in relative standard deviations (RSD), where a first RSD is a euhydration zone indicating a normal hydration zone of a user. A second RSD can indicate a hypohydration zone when the deviation is below the reference value or a hyperhydration zone when the deviation is above the reference value. The phase ranges, the coefficient of variation, and RSD are not intended to be limiting. The values and ranges of the phase ranges, coefficients of variation, and RSDs may vary. For example, different users may have different phase ranges, coefficients of variation, and RSDs.

The removed device phase 1550 can be when the electronic device is removed from a body of the user. In one example, the electronic device can determine that it has been removed when the trending data ceases. In another example, the electronic device can determine that it has been removed when the trending data decreases to zero or near zero. In another example, the electronic device can determine that it has been removed when the trending data is stagnant or flat lined. In another example, the electronic device can determine that it has been removed when the trending data becomes highly noisy.

The trending data can also include tags with information identifying additional information associated with a point in time or time periods during a measurement period. For example, the tags can include: refractometer measurement information; an impedance pad wetting status, such as whether the impedance pads were wetted before the electronic device was attached to the user; fluid intake or excretion, such as drinking or urinating; and types of activities of the user, such as running, sleeping, or waking up.

Data points can be tagged with various icons symbolic of the event (e.g., a heart signifying information related to a heart rate, a toilet signifying fluid excretion; a water bottle signifying fluid intake, and a running figure signifying a user exercised). In one example, the processing logic can tag event using measurement information. For example, the processing logic can tag a start of an exercise period of the user when an accelerometer measures an increase in activity of the user. In another example, the electronic device can receive tagging information from an input device, such as via a graphical user interface displayed on a touch screen.

Figure 15A:
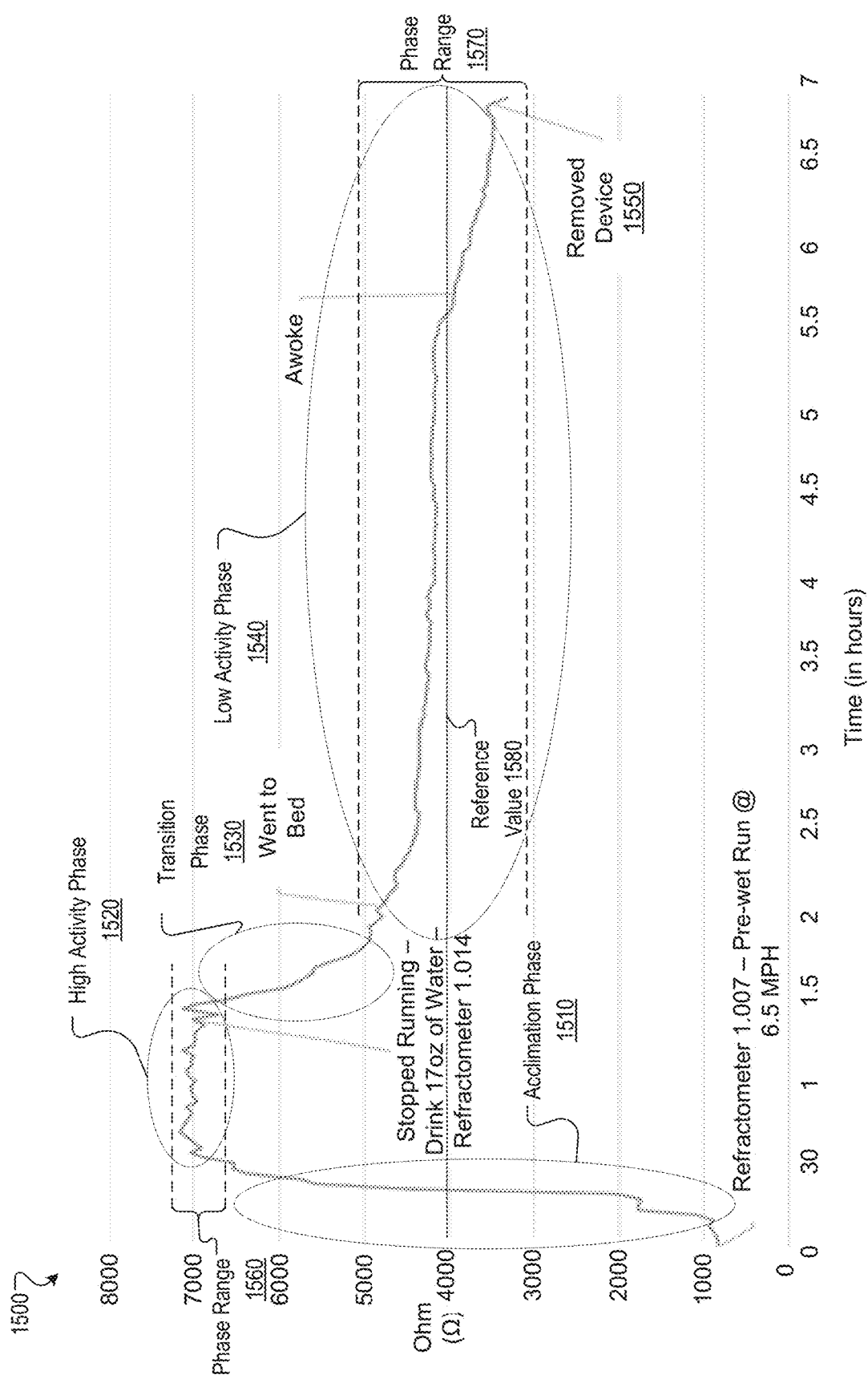
FIG. 15A illustrates an impedance trending graph of measurement data taken using a sensor of an electronic device during a high activity phase and a low activity phase of a user of the electronic device according to one embodiment.
Figure 15B:
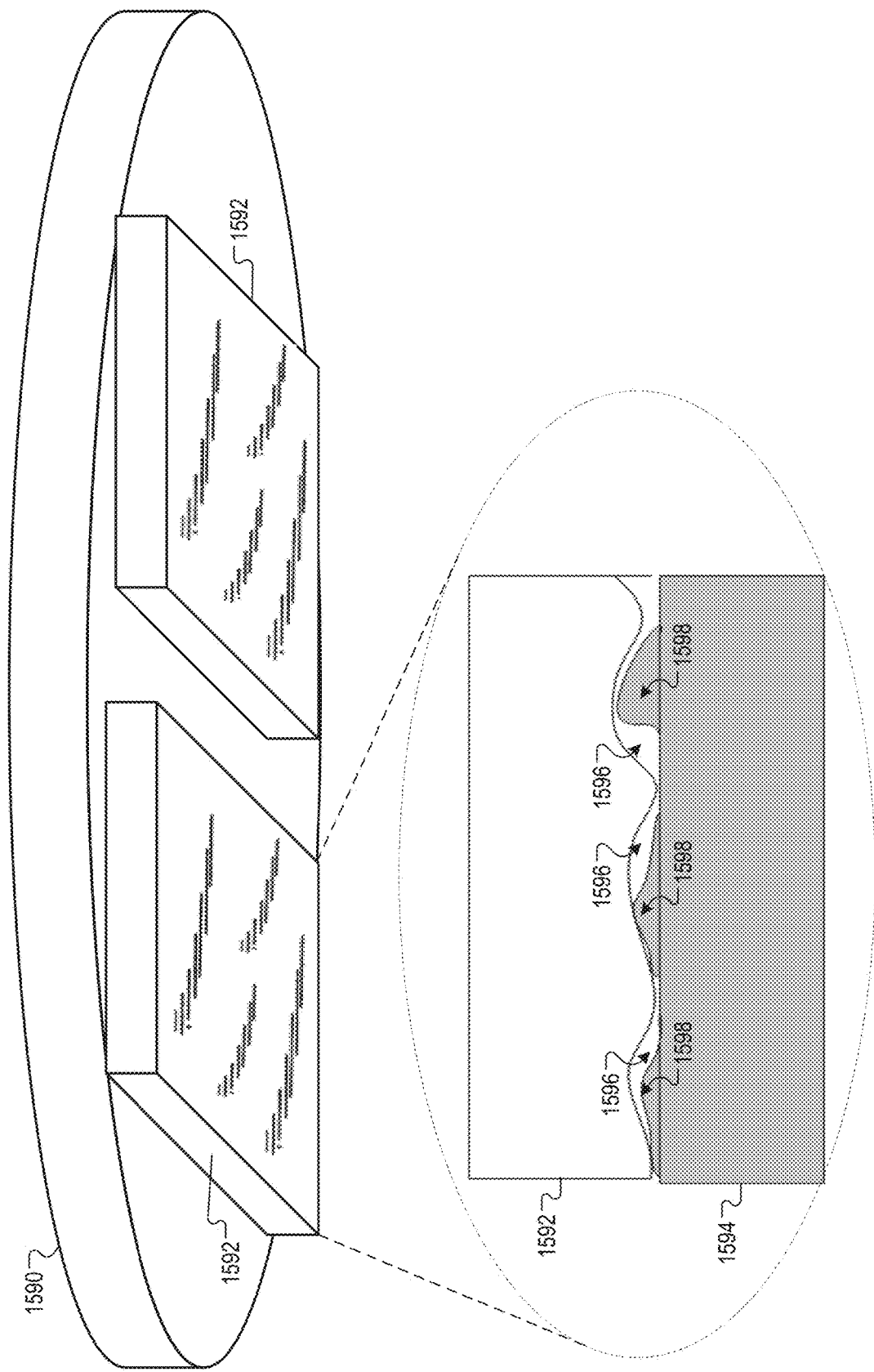
FIG. 15B illustrates physiological adjustment of a body part of the user when an electronic device is attached to the body according to one embodiment.

FIG. 15B illustrates physiological adjustment of a body part 1594 of the user when an electronic device 1590 is attached to the body according to one embodiment. For example, the electronic device 1594 can include one or more impedance pads 1592 that the electronic device 1590 can use to take impedance measurements. The surface of the impedance pads 1592 can be uneven or porous. When the impedance pads 1592 initially contacts the body part 1594, there can be are gaps 1596 between the impedance pads 1592 and the body part 1594. As the body part 1594 physiologically adjustments to the attachment of the impedance pads 1592 to the body part 1592, a surface 1598 (such as skin) of the body part 1594 can fill in the gaps 1596 over the acclimation phase 1510 (FIG. 15A) and can return to a relatively smooth surface over the de-acclimation phase 1530 (FIG. 15A). The electronic device 1590 can monitor trending data during the acclimation phase to determine when the body part 1590 has physiologically adjusted. For example, when there are gaps between the surface 1598 and the impedance pads 1592, the impedance pads 1592 may not fully contact the surface 1598 of the body part 1594 causing a lower conductivity level between multiple impedance pads 1592.

As the surface 1598 fills in the gaps 1596, the conductivity level can increase because of the reduction or elimination of the gaps 1596. In another embodiment, the physiological adjustment of the body part 1590 during the acclimation period 1510 can be caused by a change in body temperature, such as an increase in the body temperature, because the electronic device 1590 and impedance pads 1592 capture and reflects heat emitted from the body part 1594. In another embodiment, the physiological adjustment of the body part 1590 during the acclimation period can be caused by body 1594 adjusting to pressure on the surface 1598 of the body part 1594. The preceding examples and embodiment of the physiological adjustment of the body part 1590 during the acclimation period are not intended to be limiting. The physiological adjustment of the body part 1590 during the acclimation period can be caused by a variety of physiological reasons. The de-acclimation phase 1530 can be the reverse of physiological adjustment described for the acclimation period 1510.

Figure 15C:
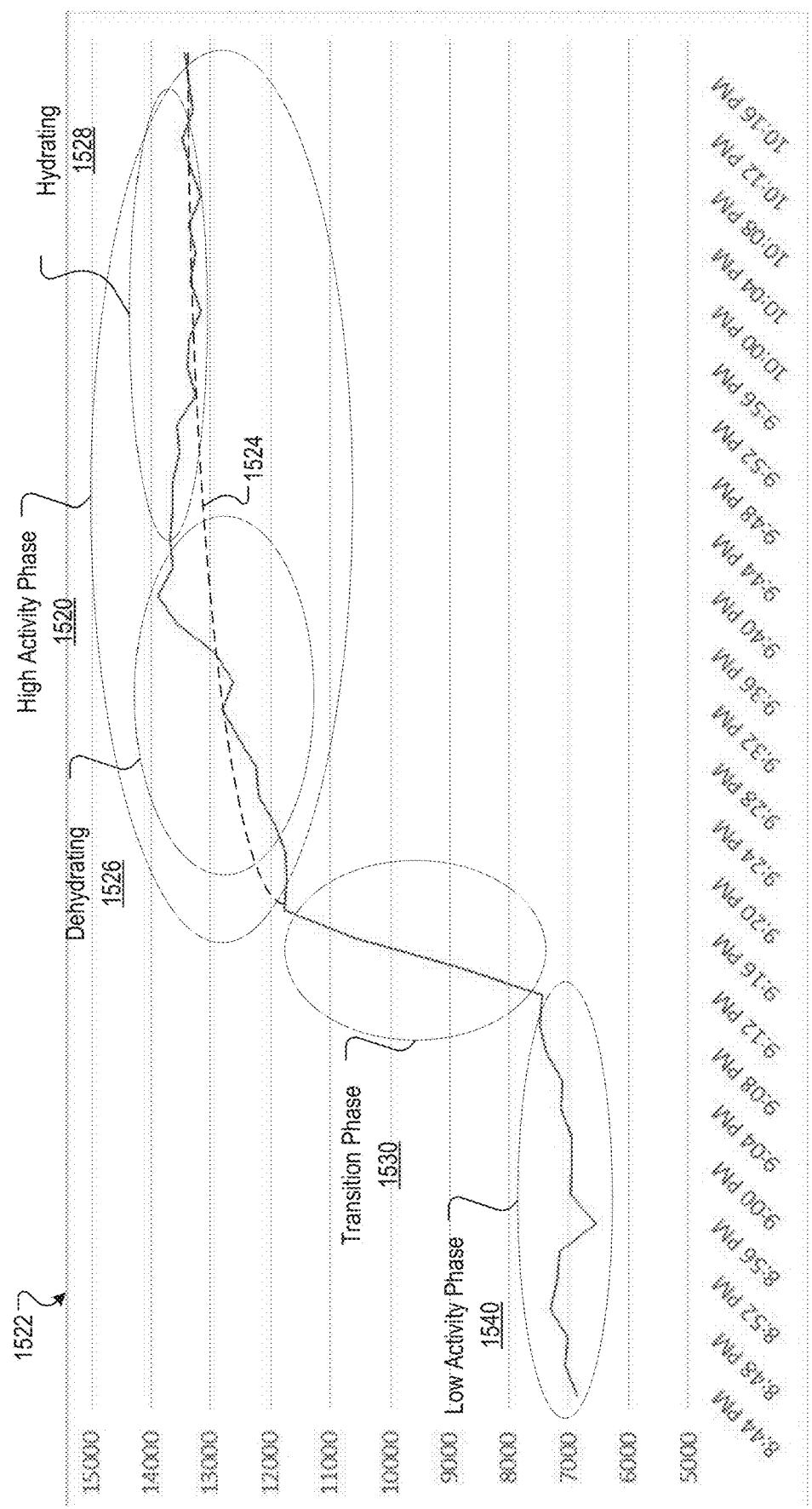
FIG. 15C illustrates an impedance trending graph of measurement data taken during a high activity phase according to one embodiment.

FIG. 15C illustrates an impedance trending graph 1522 of measurement data taken during a high activity phase 1520 according to one embodiment. In one embodiment, the impedance trending graph 1522 can include the low activity phase 1540, a transition phase 1530, and a high activity phase 1520. The high activity phase 1520 can be a phase when a user is physically exerting himself or herself for a period of time. For example, the high activity phase 1520 can be when the user is running, jogging, working out, and so forth. In another embodiment, the high activity phase 1520 can be a phase when a user is in a high dehydration risk environment for a period of time. For example, the high activity phase 1520 can be when the user is in a relatively high humidity environment, a relatively high ambient temperature environment, and so forth. In one example, the electronic device can determine that trending information is for the high activity phase 1520 when a rate of change of the trending information is within a threshold range. In another example, the electronic device can determine that trending information is for the high activity phase 1520 when the trending information spans a defined range of impedance values, such as approximately 6500 Ohms ($\Omega$) to 7500$\Omega$.

In one embodiment, the electronic device can identify a phase of the measurement data. The electronic device can use different trending parameters for different phases to determine a hydration condition of a user. For example, the electronic device can identify that the measurement data is for the high activity phase 1520. The electronic device can determine that when a trending of the measurement data indicates an increase in impedance values, a user is becoming dehydrated (1526). The electronic device can determine that when a trending of the measurement data indicates a decrease in impedance values, a user is becoming hydrated (1528). In another example, the electronic device can use an overall trending direction (1524) of the measurement data to determine a hydration condition of the user.

In one embodiment, different measurement phases can have different analysis parameters. For example, the electronic device can use a first parameter set when the trending information is for a high activity phase 1520. In another example, the electronic device can use a second parameter set when the trending information is for a low activity phase 1540.

Figure 15D:
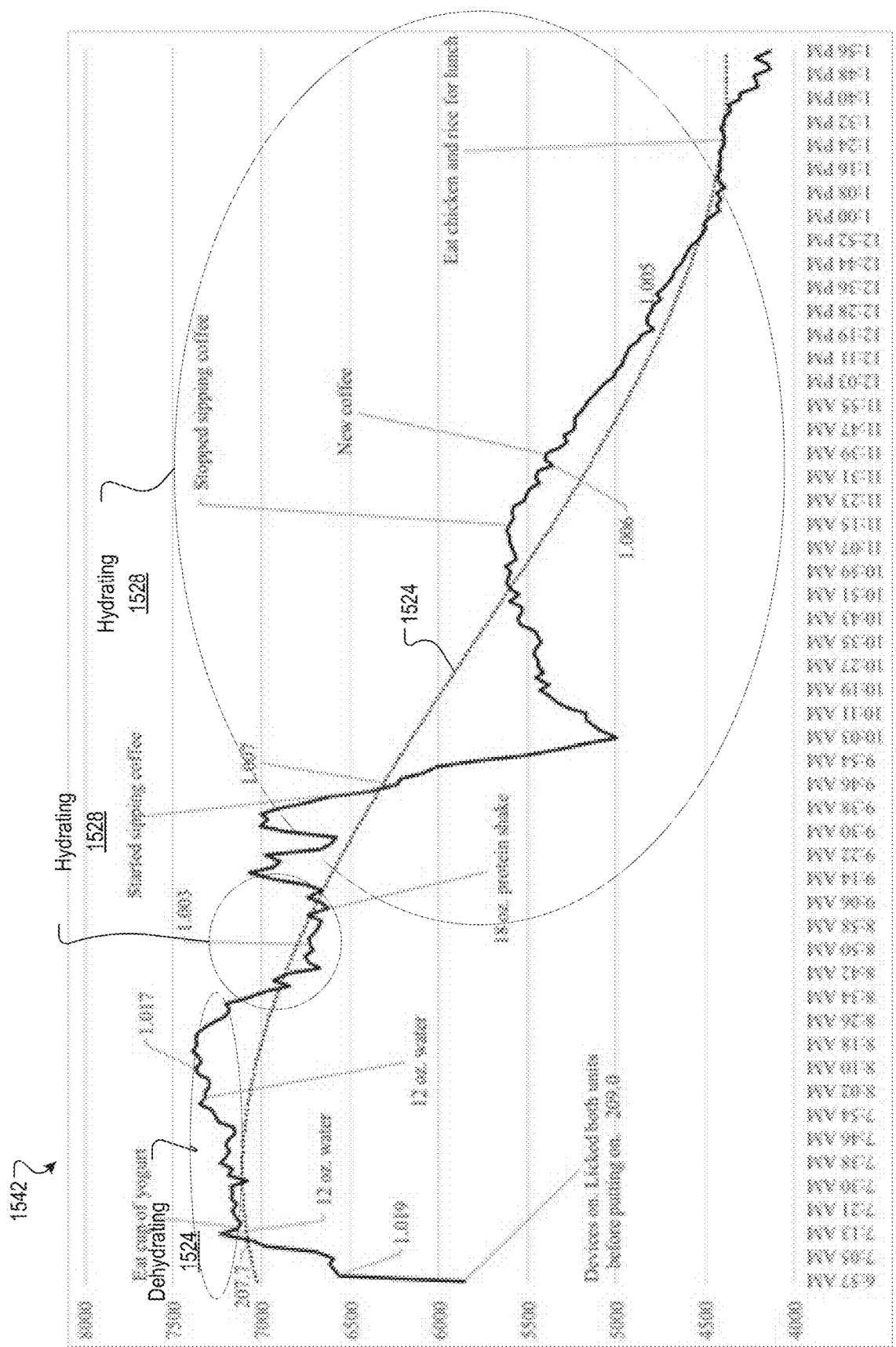
FIG. 15D illustrates an impedance trending graph of measurement data taken during a low activity phase according to one embodiment.

FIG. 15D illustrates an impedance trending graph 1542 of measurement data taken during a low activity phase according to one embodiment. The low activity phase 1540 can be a phase when a user is not physically exerting himself or herself or minimally physically himself or herself for a period of time. For example, the low activity phase 1540 can be when the user is sitting at a desk, driving, sleeping, lying down, eating lunch, and so forth. In one example, the electronic device can determine that trending information is for the low activity phase 1540 when a rate of change of the trending information is within a threshold range. In another example, the electronic device can determine that trending information is for the low activity phase 1540 when the trending information spans a defined range of impedance values, such as approximately 2500 Ohms (Ω) to 5500Ω.

In one embodiment, the electronic device can identify a phase of the measurement data. The electronic device can use different trending parameters for different phases to determine a hydration condition of a user. For example, the electronic device can identify that the measurement data is for the low activity phase. The electronic device can determine that when a trending of the measurement data indicates an increase in impedance values, a user is becoming dehydrated (1526). The electronic device can determine that when a trending of the measurement data indicates a decrease in impedance values, a user is becoming hydrated (1528). In another example, the electronic device can use an overall trending direction (1524) of the measurement data to determine a hydration condition of the user.

Figure 16A:
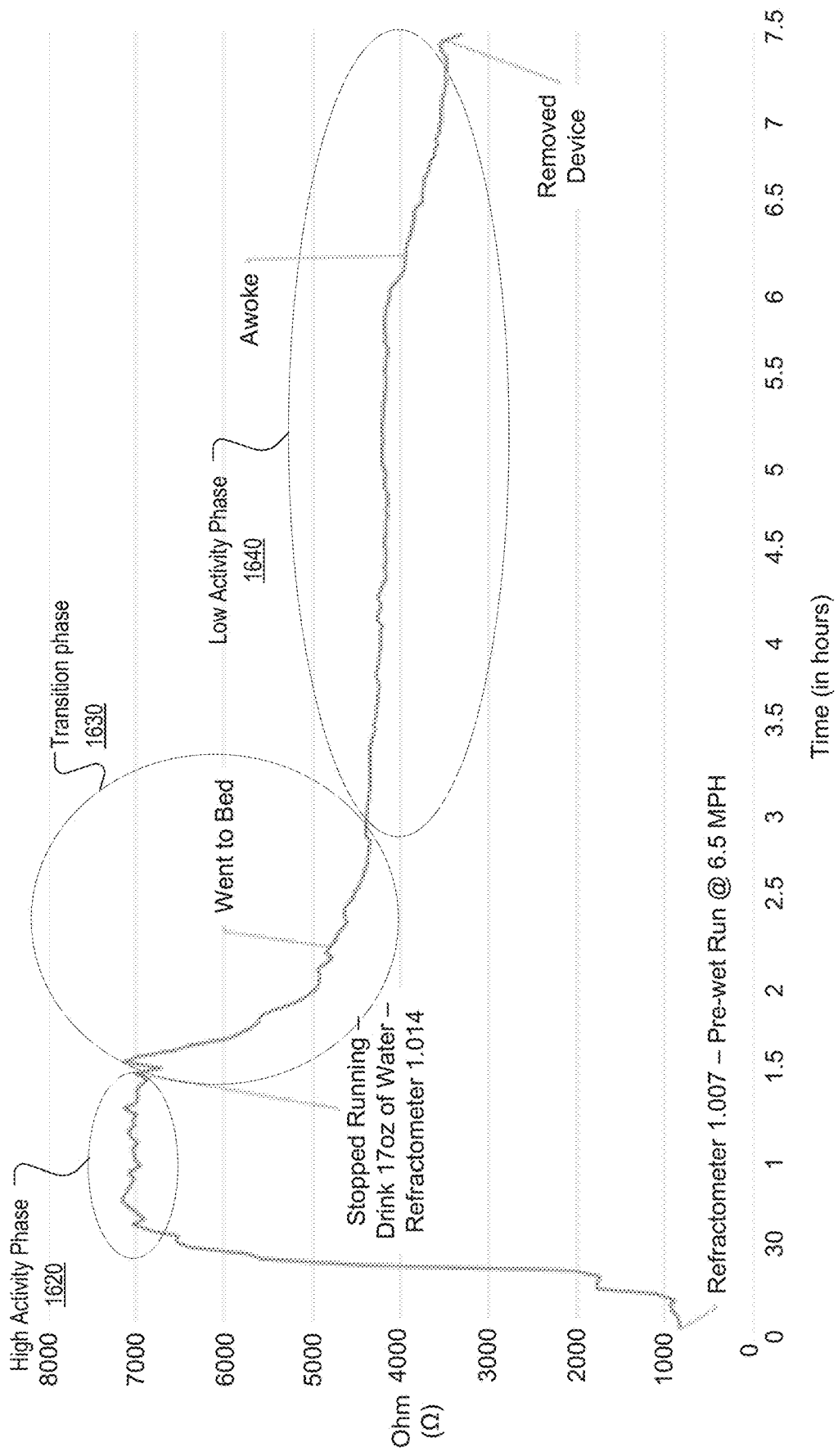
FIG. 16A illustrates an impedance trending graph of measurement data taken by the electronic device during a transition phase according to one embodiment.

FIG. 16A illustrates an impedance trending graph 1600 of measurement data taken by the electronic device during a transition phase 1630 according to one embodiment. The transition phase 1630 is a phase when the trending data shifts from a high activity phase 1620 to a low activity phase 1640. The electronic device can analyze the trending data to determine that the user has ceased a high activity action (such as running) and is now performing a low activity action (such as sleeping). In one embodiment, as the body of the user physiologically adjusts from the high activity phase 1620 to the low activity phase 1640, the trending data can decrease at a specified rate or a rate within a specified range. Additionally or alternatively, as the body of the user physiologically adjusts from the high activity phase 1620 to the low activity phase 1640, the trending data can decrease by a total amount of Ω.

Figure 16B:
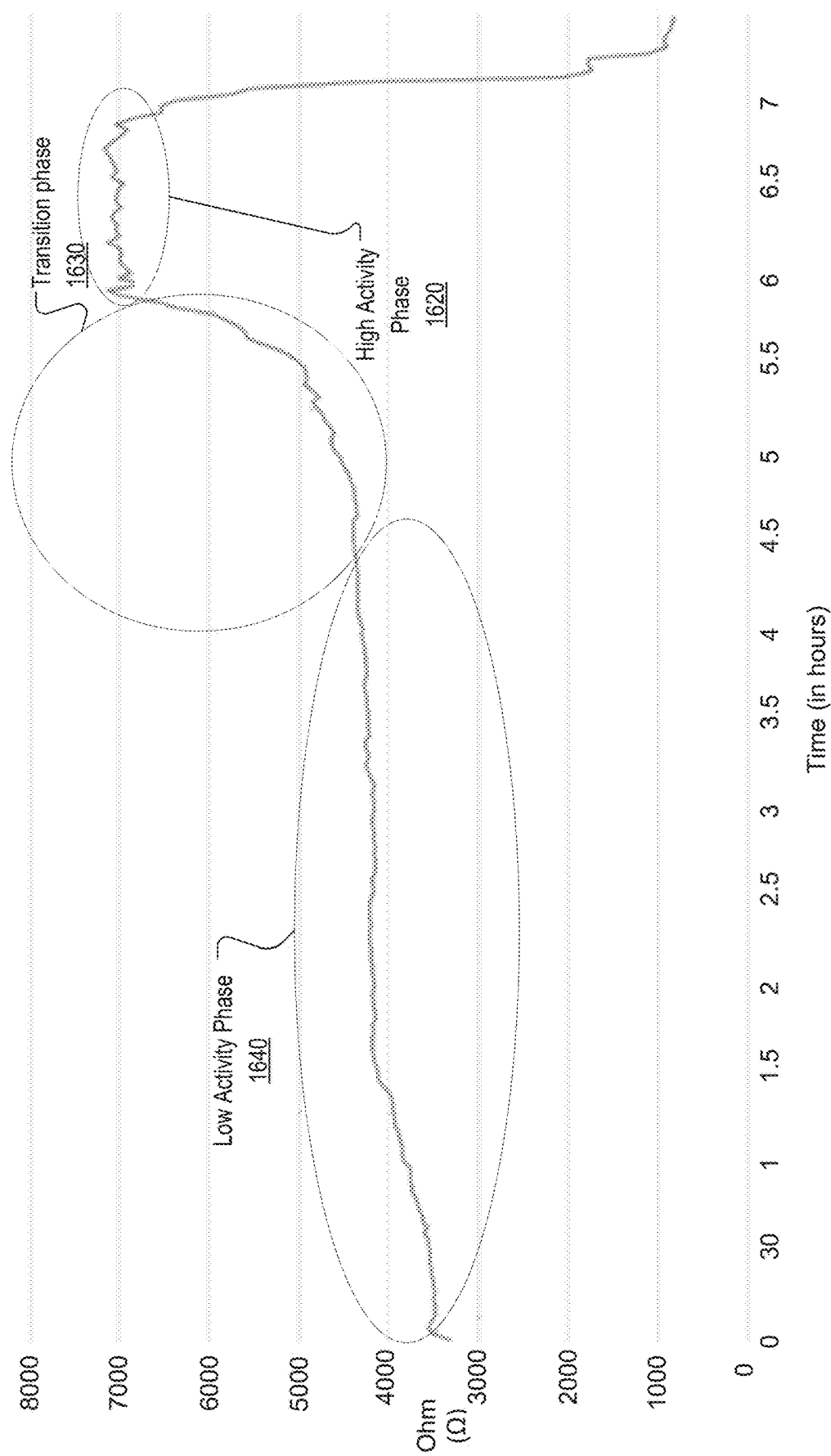
FIG. 16B illustrates an impedance trending graph of measurement data taken by the electronic device during a transition phase according to one embodiment.

FIG. 16B illustrates an impedance trending graph 1600 of measurement data taken by the electronic device during a transition phase 1630 according to one embodiment. The transition phase 1630 is a phase when the trending data shifts from a low activity phase 1640 to a high activity phase 1620. The electronic device can analyze the trending data to determine that the user has ceased a low activity action (such as sleeping) and is now performing high activity action (such as running) In one embodiment, as the body of the user physiologically adjusts from the low activity phase 1640 to the high activity phase 1620, the trending data can increase as a specified rate or a rate within a specified range. Additionally or alternatively, as the body of the user physiologically adjusts from the low activity phase 1640 to the high activity phase 1620, the trending data can increase by a total amount of Ω.

Figure 16C:
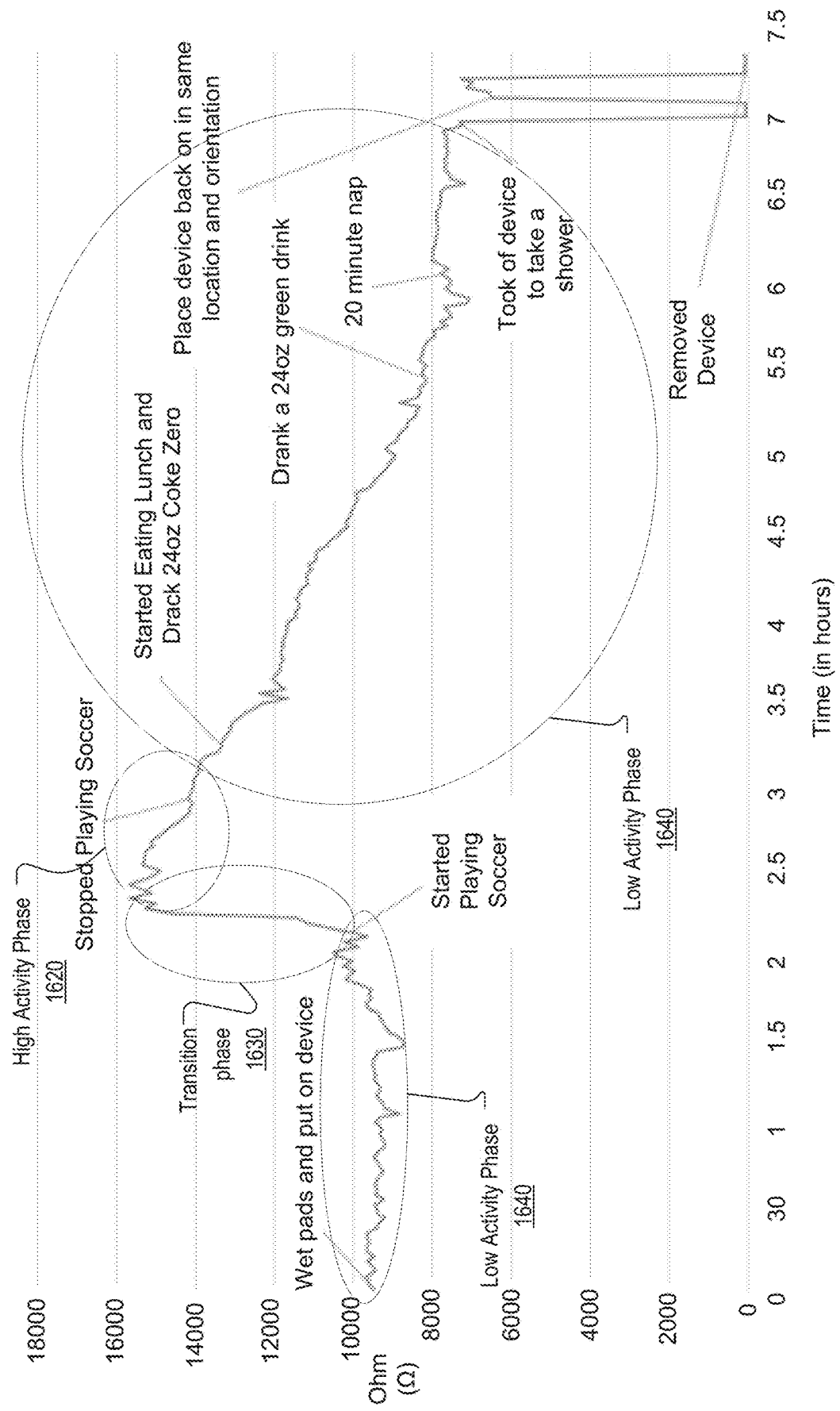
FIG. 16C illustrates an impedance trending graph of measurement data taken by the electronic device during a transition phase according to one embodiment.

FIG. 16C illustrates an impedance trending graph 1600 of measurement data taken by the electronic device during a transition phase 1630 according to one embodiment. The transition phase 1630 is a phase when the trending data shifts from a low activity phase 1640 to a high activity phase 1620 and back to the low activity phase 1640. The electronic device can analyze the trending data to determine that the user has ceased a low activity action (such as sitting) and performed high activity action (such as running) and then returned to the low activity action (such as eating lunch and working). In one embodiment, as the body of the user physiologically adjusts from the low activity phase 1640 to the high activity phase 1620, the trending data can increase as a specified rate or a rate within a specified range. In another embodiment, as the body of the user physiologically adjusts from the high activity phase 1620 to the low activity phase 1640, the trending data can decrease as a specified rate or a rate within a specified range. Additionally or alternatively, as the body of the user physiologically adjusts from the high activity phase 1620 to the low activity phase 1640, the trending data can decrease by a total amount of Ω.

Figure 17A:
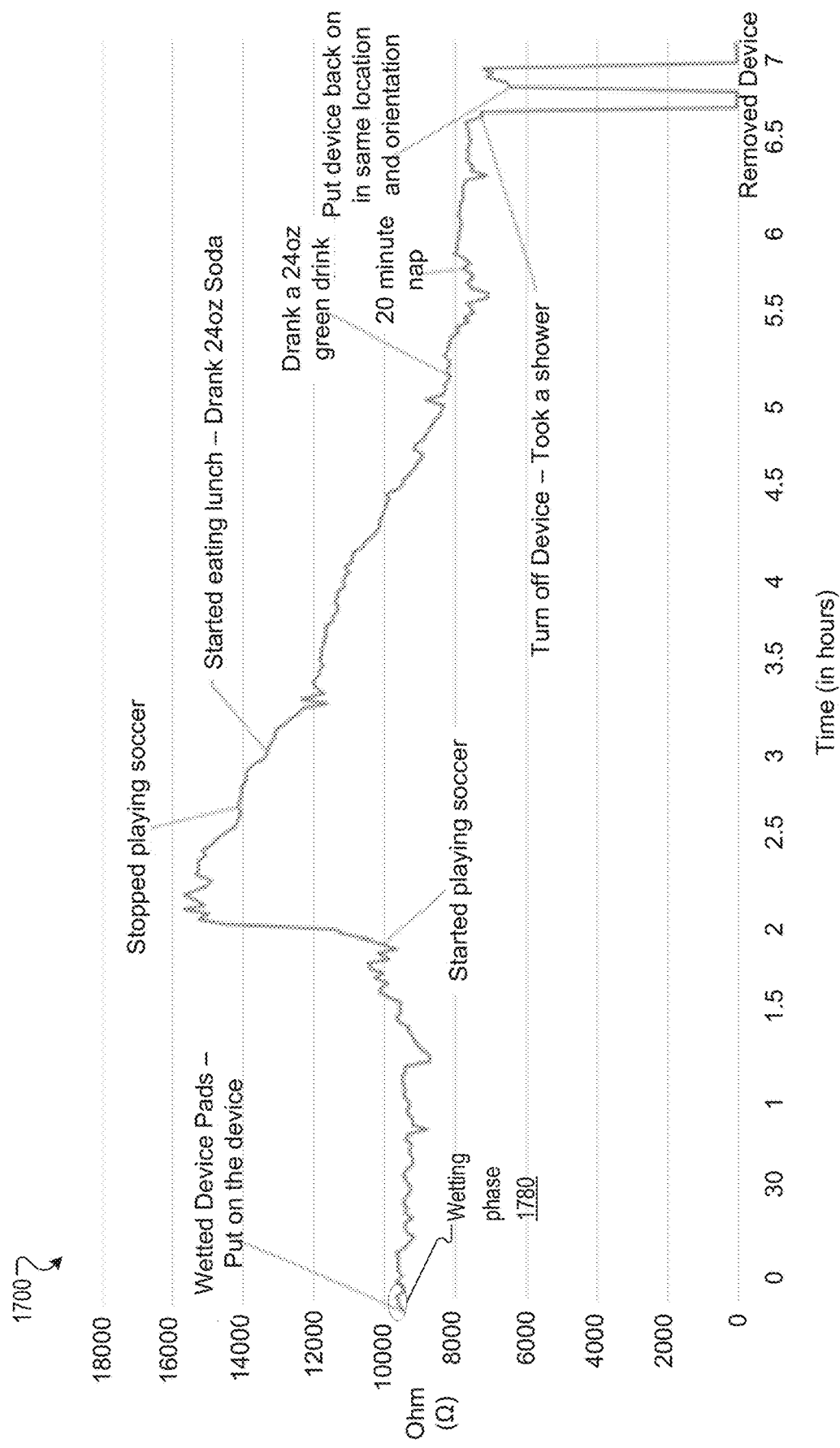
FIG. 17A illustrates an impedance trending graph of measurement data taken by the electronic device during a wetting phase according to one embodiment.

FIG. 17A illustrates an impedance trending graph 1700 of measurement data taken by the electronic device during a wetting phase 1780 according to one embodiment. Before application of an electrode (such as an impedance pad) to a user's body surface, a membrane of the electrode may be wetted with a wetting agent which permeates the membrane. The wetting agent is electrically conductive or will become electrically conductive upon contact with the user's skin. For example, the wetting agent can be saliva, conductive gel, water, and so forth. The wetting agent enhances a conductivity of the membrane to create a low resistance path to current flowing between multiple electrolytes through the user's skin. In one example, the membrane can include polytetrafluoroethylene embedded with fiberglass and a drop of water can be used as the wetting agent to wet the membrane to enhance its conductivity. In one example, water can be conductive due to the presence of impurities in the water. In another example, water can become conductive when it contacts body salts on a user's skin. After wetting the membrane a base of the electrode may be applied to the skin. The electronic device can determine that the trending data is in a wetting phase 1780, where the electrode has been wetted and applied to the user's skin, because the trending data has a no acclimation phase 1510 (FIG. 15A) or a minimal acclimation phase 1510. The wetting of the electrodes can shorten or eliminate the acclimation phase 1510 because the wetting agent can fill in the gaps 1596 (FIG. 15B) between surface 1598 and the electrodes 1592, as discussed in the preceding paragraphs. The electronic device can analyze the trending data to determine that the electronic device is receiving measurements and there is not the acclimation phase 1510 at the beginning of the trending data.

Figure 17B:
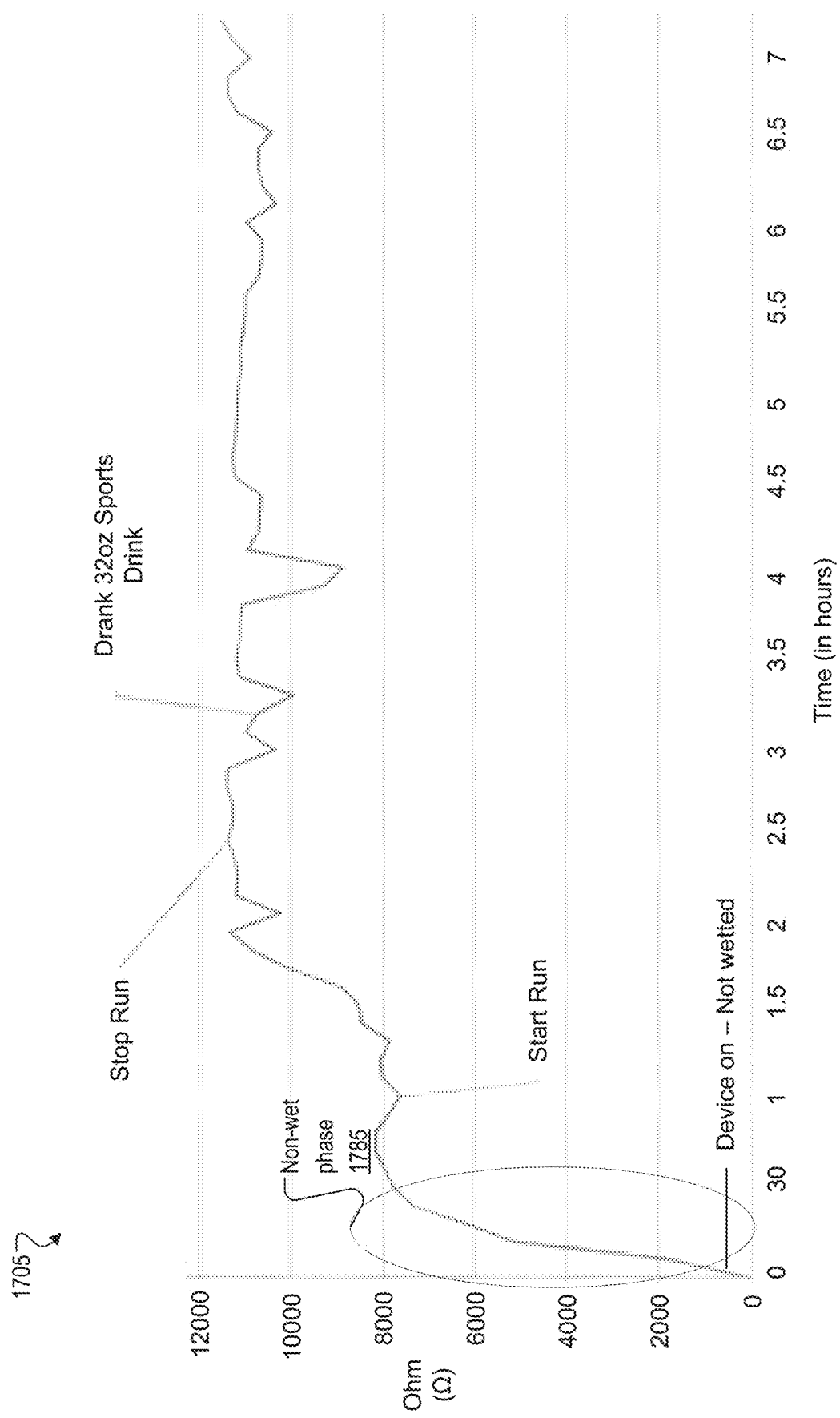
FIG. 17B illustrates an impedance trending graph of measurement data taken by the electronic device when an impedance pad of the electronic device during a non-wet phase according to one embodiment.

FIG. 17B illustrates an impedance trending graph 1705 of measurement data taken by the electronic device when an impedance pad of the electronic device during a non-wet phase 1785 according to one embodiment. As discussed in the preceding paragraphs, when electrodes of the electronic device are wetted, the conductivity between the electrodes is enhanced. When the trending of the measurement data indicates a non-wet phase 1785, the electronic device can analyze the trending data to identify a period in the trending data where the impedance level starts at zero or a negligible Ω and increases to a non-activity Ω level or an activity Ω level. For example, when the electrodes are not wetted prior to attaching the electronic device to a body of a user, the trending data can start at 0Ω and can increase to 8000Ω (an activity Ω level).

Figure 17C:
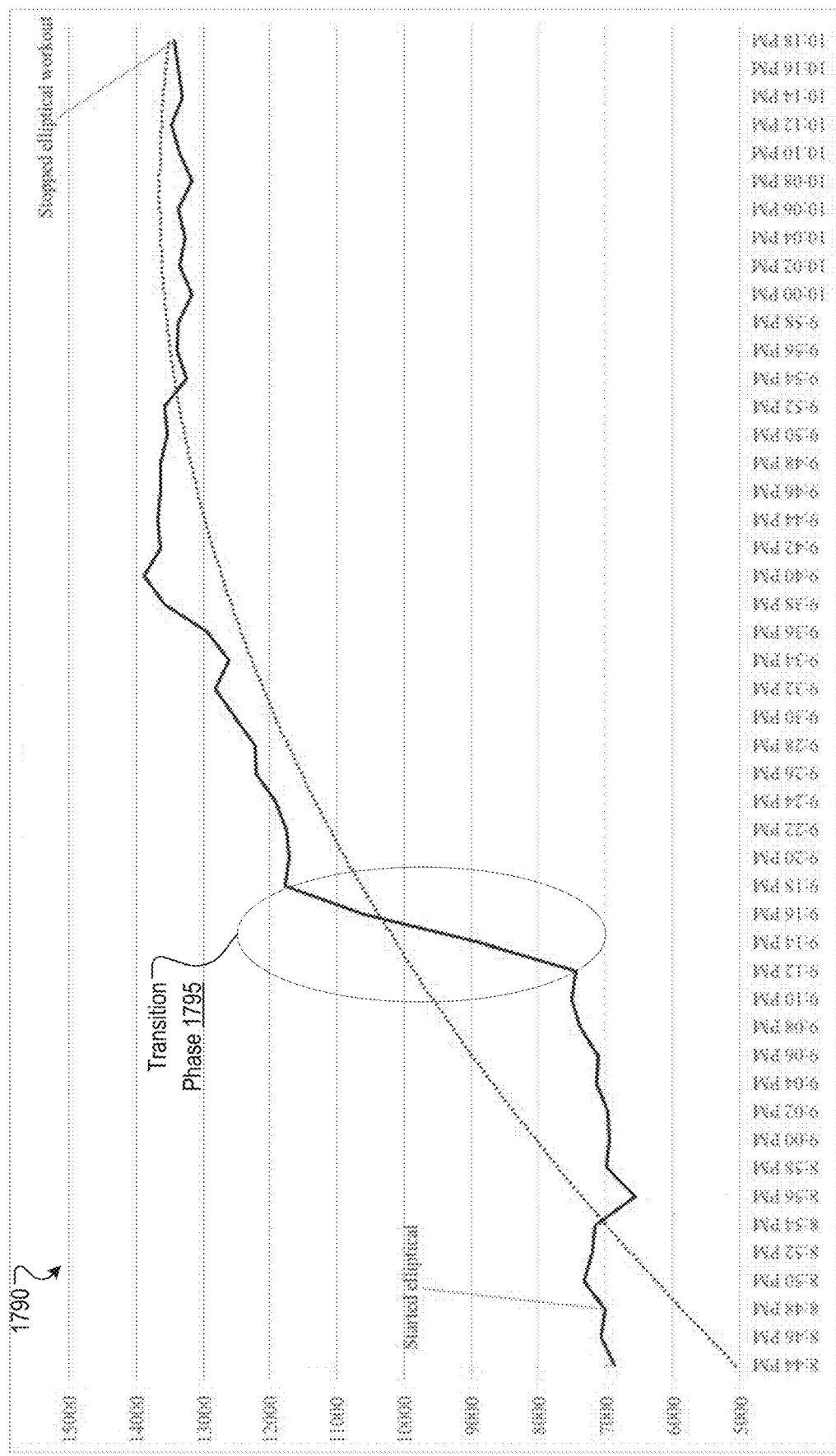
FIG. 17C illustrates an impedance trending graph of measurement data with a transition phase according to one embodiment.

FIG. 17C illustrates an impedance trending graph 1790 of measurement data with a transition phase 1795 according to one embodiment. In one example, the transition phase 1795 can occur when the measurement data transitions from a high activity level to a low activity level. In another example, the transition phase 1795 can occur when the measurement data transitions from a low activity level to a high activity level. In another example, there can be a physiological delay between a user starting a high activity level event and the measurement data reflecting the transition from the low activity level to the high activity level. For example, a user can begin using an elliptical to work out but the transition period may occur at a later point. The physiological delay can be caused by a body of the user adjusting from the low activity level event to the high activity level event, such as a delay in perspiration between when the elliptical workout began and when the user began to perspire.

Figure 17D:
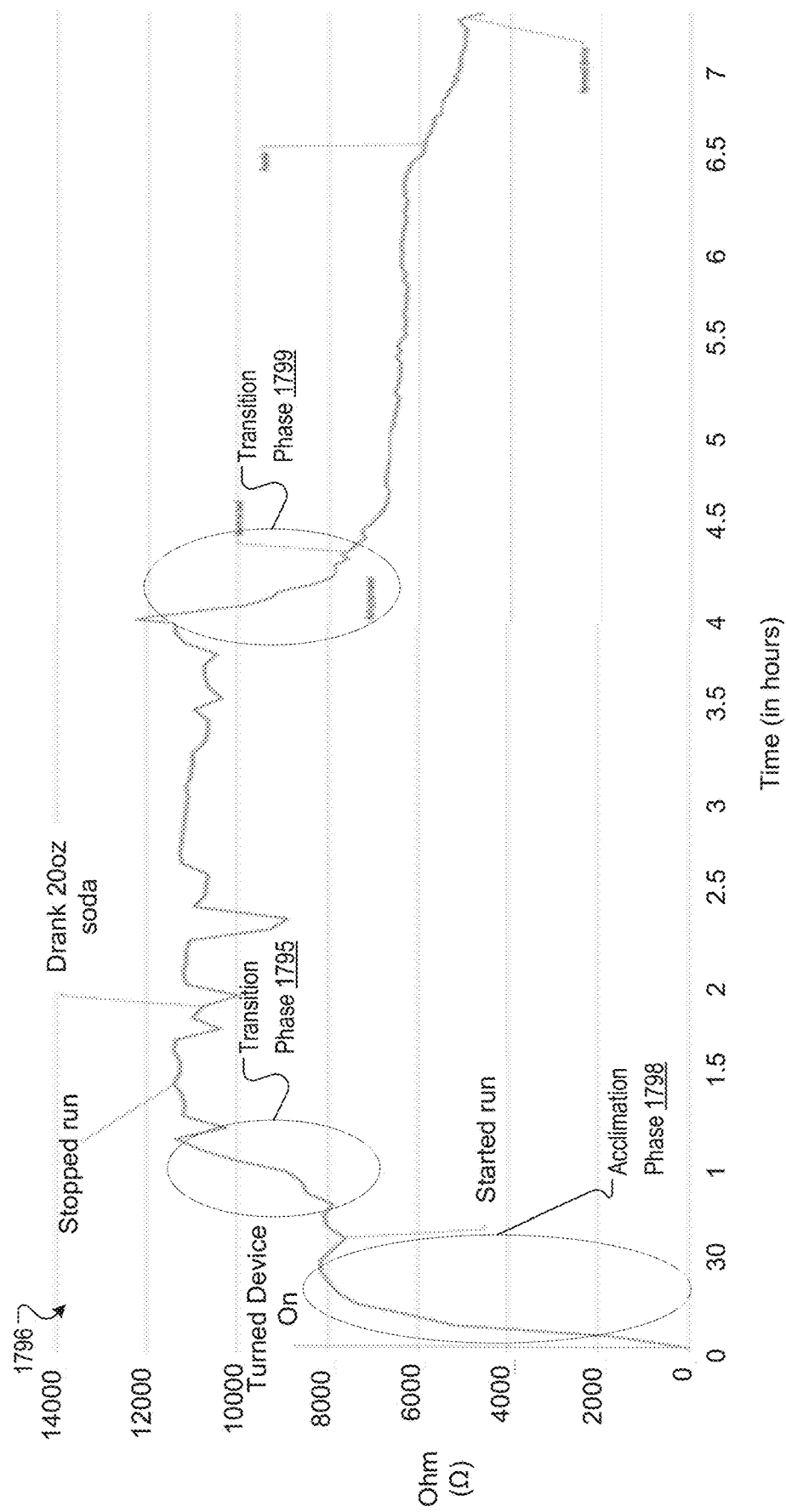
FIG. 17D illustrates an impedance trending graph of measurement data with an acclimation phase and transition phases and according to one embodiment.

FIG. 17D illustrates an impedance trending graph 1796 of measurement data with an acclimation phase 1798 and transition phases 1795 and 1799 according to one embodiment. The acclimation phase 1798 can occur when the electronic device is initially attached to the user. The transition phase 1795 can occur when the user begins a high activity level event. The transition phase 1799 can occur after the user ends their high activity level event.

Figure 18:
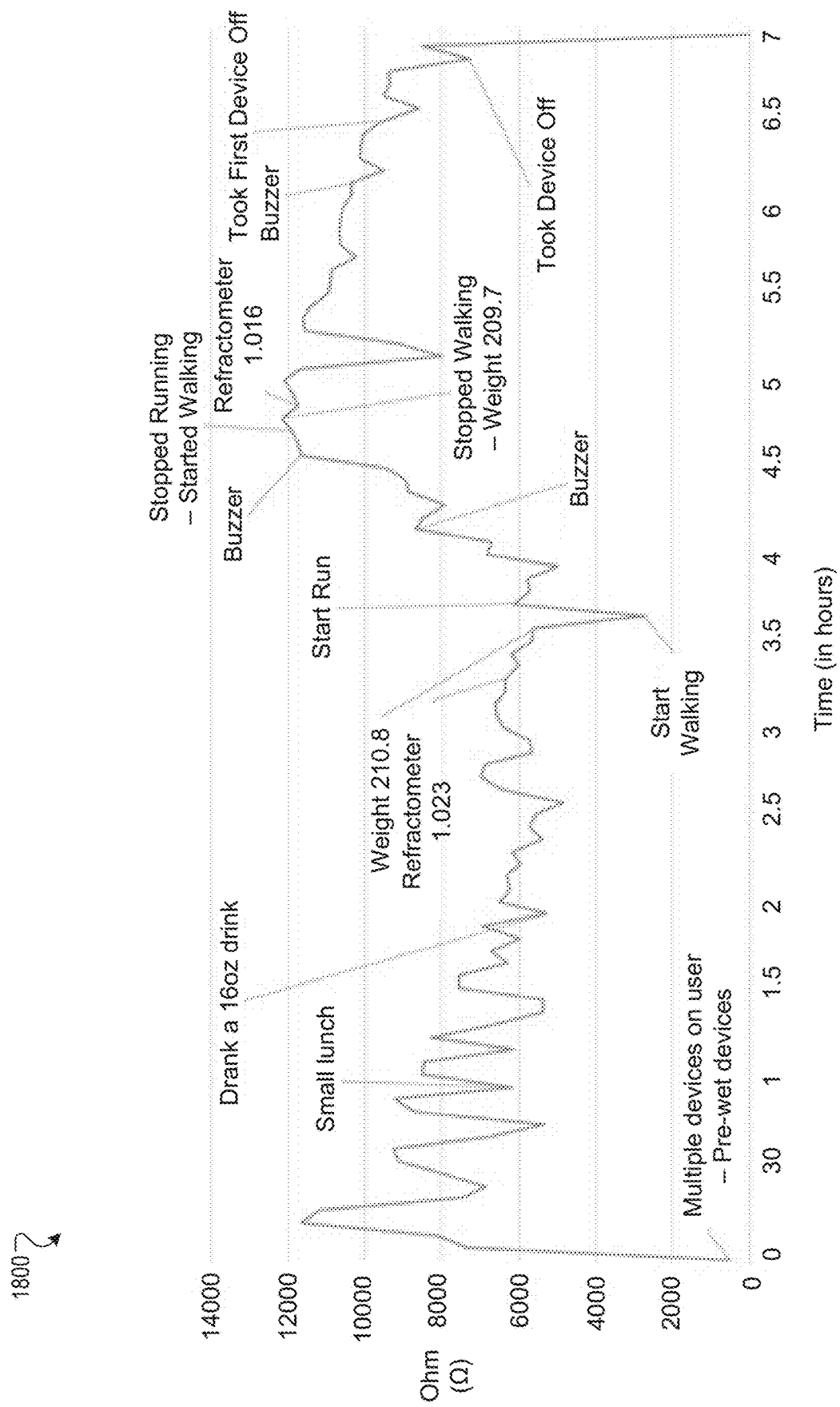
FIG. 18 illustrates an impedance trending graph for measurement data with noise in the measurement data according to one embodiment.

FIG. 18 illustrates an impedance trending graph 1800 for measurement data with noise in the measurement data according to one embodiment. The electronic device can determine that there is noise in the measurement data when a first data point in the measurement data jumps or skips from a first Ω level to a second Ω level, where the first Ω level and the second Ω level have a threshold difference in values. For example, when the trending graph 1800 has jagged or non-smooth trending, the jagged or non-smooth trending can indicate that there is noise in the measurement data. In one embodiment, when the electronic device determines there is noise in the data, the electronic device can smooth the measurement data using a smoothing function. In another embodiment, when the electronic device determines there is noise in the data, the electronic device can remove erroneous data points from the measurement data.

Figure 19:
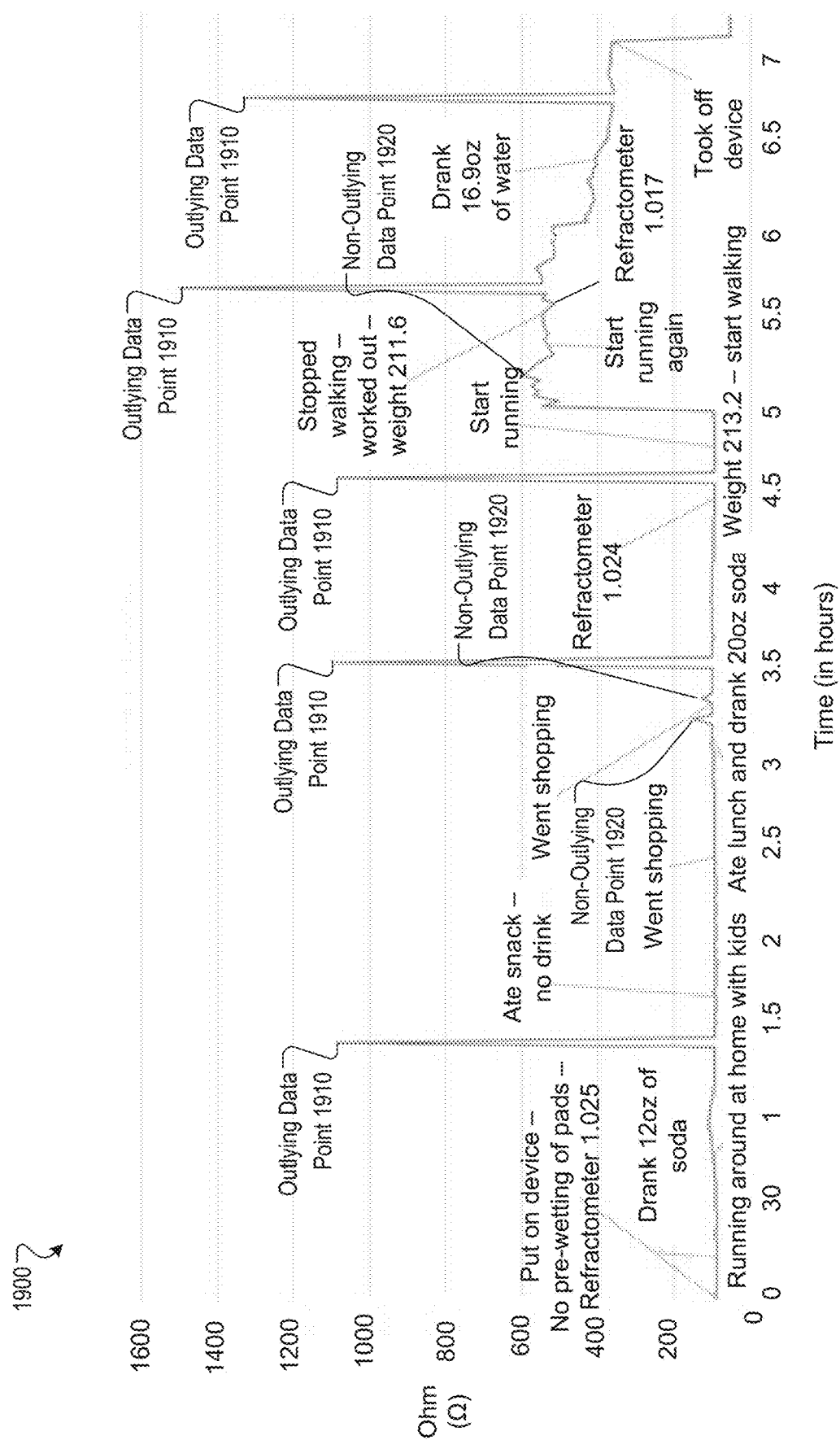
FIG. 19 illustrates an impedance trending graph for measurement data with outlying data points 1910 in the measurement data according to one embodiment.

FIG. 19 illustrates an impedance trending graph 1900 for measurement data with outlying data points 1910 in the measurement data according to one embodiment. The electronic device can determine that there are outlying data points 1910 in the measurement data by comparing a value of a first data point in the measurement data to a value of a second data point in the measurement data. When the difference between the first value and the second value exceeds a threshold difference between values, the electronic device can determine that the first data point or the second data point is an outlying data point 1910. In one embodiment, to determine whether the first data point is an outlying data point, the electronic device can compare the first data point to a third data point that precedes the first data point. In one example, when a difference between the first data point and the third data point is with a threshold range, the first data point is non-outlying data point 1920. In another example, when the difference between the first data point and the third data point exceeds the threshold range, the first data point is an outlying data point. The electronic device can make a similar determination for the second data point by comparing the second data point with a fourth data point that proceeds the second data point. When the electronic device identifies the outlying data point 1910, the electronic device can remove the outlying data point 1910 from the trending data.

In one example, the electronic device can identify the outlying data points using the same statistical methodology used to identify step changes in the trend data. Outlying data point elimination can be performed by excluding all data points from a hydration calculation that are outside a predetermined tolerance band for a given sample of data for the statistical analysis technique used. In one example, the statistical analysis technique is a standard deviation technique can be used to measure the scatter in a sample of data around the average for the population of data. An outlying data point can be determined by defining it as any point that is more than some number of standard deviations from the average.

Figure 20:
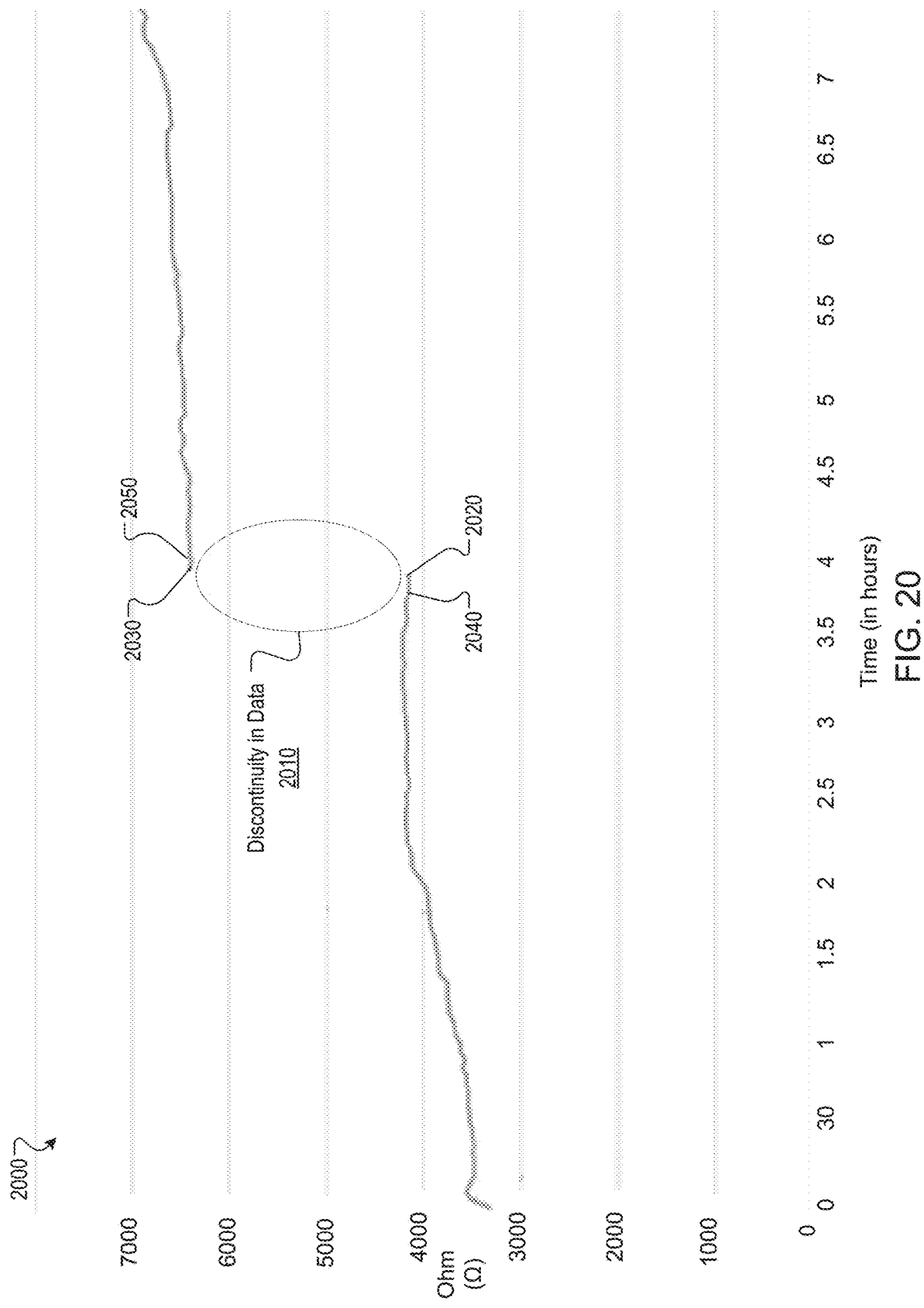
FIG. 20 illustrates an impedance trending graph for measurement data with a discontinuity in the measurement data according to one embodiment.

FIG. 20 illustrates an impedance trending graph 2000 for measurement data with a discontinuity 2010 in the measurement data according to one embodiment. The electronic device can identify a discontinuity 2010 in the measurement data by comparing a value of a first data point 2020 in the measurement data to a value of a second data point 2030 in the measurement data. When the difference between the first value and the second value exceeds a threshold difference between values, the electronic device can identify the discontinuity 2010 the first data point 2020 and the second data point 2030. To identify the discontinuity 2010 the electronic device can compare the first data point 2020 to a third data point 2040 that precedes the first data point 2020. When a difference between the first data point 2020 and the third data point 2040 is with a threshold range, the first data point 2020 is at a first trending level and is not an outlying or erroneous data point. Additionally, to identify the discontinuity 2010 the electronic device can compare the second data point 2030 to a fourth data point 2050 that follows the second data point 2030. When a difference between the second data point 2030 and the fourth data point 2050 is with a threshold range, the second data point 2030 is at a second trending level and is not an outlying or erroneous data point. In this example, when the difference between the first value and the second value exceeds a threshold difference between values and the first data point 2020 and the second data point 2030 are not outlying or erroneous data points, there is a discontinuity 2010 between the first data point 2020 and the second data point 2030.

In one embodiment, the processing logic of the electronic device can detect abnormal shifts or changes in trended data. This detection is preferably performed using a statistical control chart method, which identifies special cause variations in time-ordered data. In one example, parametric filtering can be used to prevent false hits and single parameter fluctuations.

In one embodiment, the control chart method can include one or more trend parameters, determining if the latest, i.e., most recent, point in the trend sample is greater than the upper control limit (UCL) or lower than the lower control limit (LCL). A flag can be set for each trending data that exceeds either of these limits. The flag should also include an indication of which limit, upper or lower, was exceeded. The flags are used to perform parametric filtering for the trend analysis.

In one example all detected shifts, occurring at a single point in time, i.e. at the same trend point, are analyzed using a parametric filtering technique. If only a single parameter is flagged out of range, the event is an outlying parameter and no hydration condition message is generated. If more than one parameter shifts at a single point in time, specific parameters and their direction of change are compared to a fault template to determine if the shift in the trend data is characteristic of a known or recognizable cause. If the pattern matches a known cause, then a trend alarm can be generated along with its corresponding recommendation. Alternatively, an explanation of why the shift occurred can be generated. The general categories for recognizable shifts include, taking an electronic device on and off a body of the user, adjusting an orientation of the electronic device, and so forth. When more than one trend parameter shifts occur but a pattern is not recognized (i.e. not in the fault template), the trend parameter shifts may be placed on a watch list or ignored until discernable symptoms occur.

Figure 21:
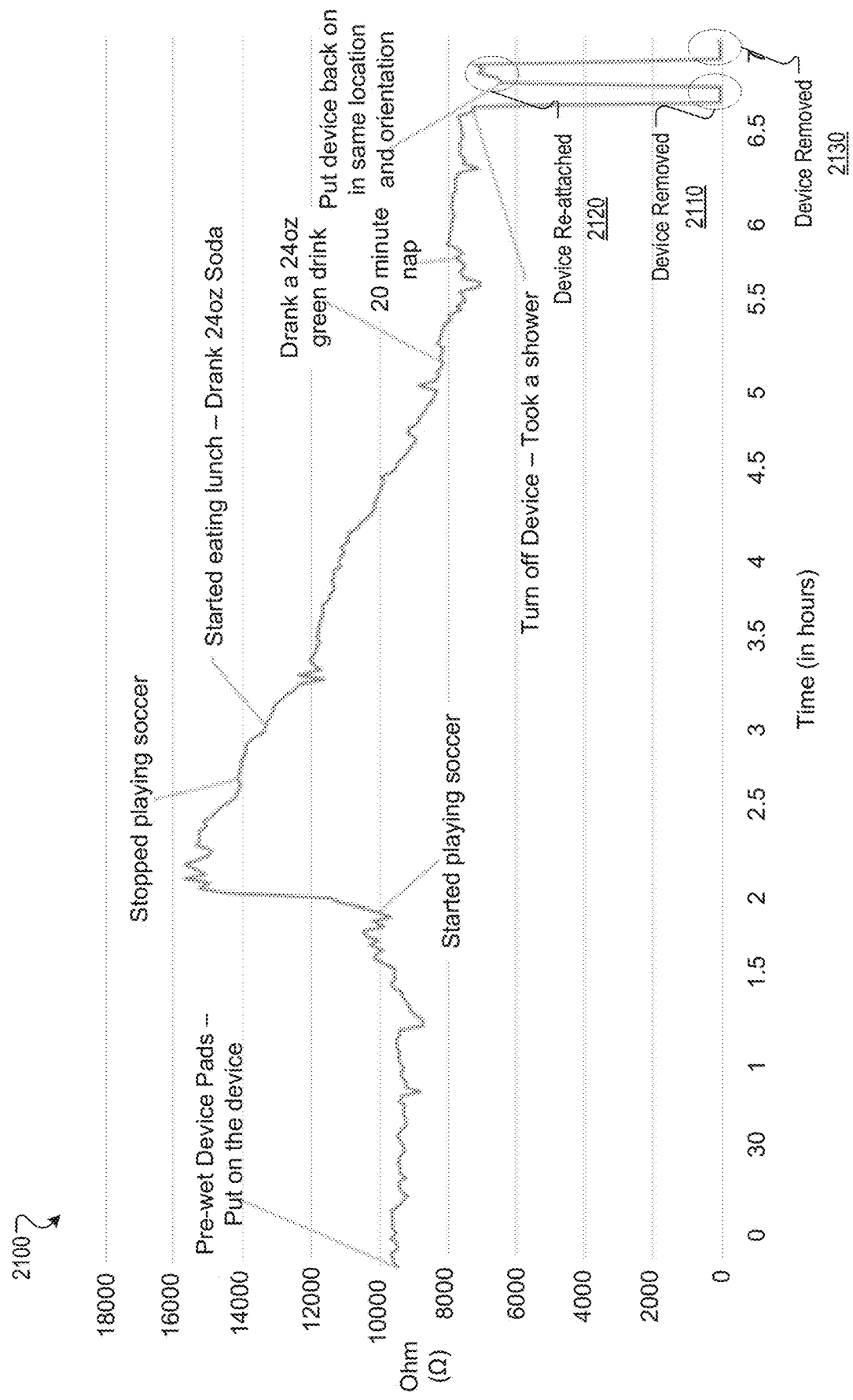
FIG. 21 illustrates an impedance trending graph of measurement data with device removal events and a device re-attachment event according to one embodiment.

FIG. 21 illustrates an impedance trending graph 2100 of measurement data with device removal events 2110 and 2130 and a device re-attachment event 2120 according to one embodiment. The electronic device can identify the device removal event 2110 or 2130 when the trending data jumps to 0Ω or near-zero Ωs. In one example, when the trending data jumps to 0Ω or near-zero Ωs the device removal event 2110 has occurred. In another example, the electronic device can compare a previous data point value prior to the jump in trending to a current data point value after the jump in the trending. When a difference between the previous data point value and the current data point value exceeds a threshold value, the device removal event 2110 or 2130 has occurred. When a difference between the previous data point value and the current data point value does not exceed the threshold value, the device removal event 2110 or 2130 has not occurred. For example, when the trending data slowly trends towards the 0Ω or near-zero Ωs, the electronic device may not have been removed as the user is greatly dehydrated.

The electronic device can identify the device re-attachment event 2120 when the trending data jumps from 0Ω or near-zero Ωs to a greater Ω value. In one example, when the trending data jumps from 0Ω or near-zero Ωs to the greater Ω value, the device re-attachment event 2120 has occurred. In another example, the electronic device can compare a previous data point value prior to the jump in trending to a current data point value after the jump in the trending. When a difference between the previous data point value and the current data point value exceeds a threshold value, the device re-attachment event 2120 has occurred. When a difference between the previous data point value and the current data point value does not exceed the threshold value, the device re-attachment event 2120 has not occurred. For example, when the trending data slowly trends towards the 0Ω or near-zero Ωs, the electronic device may not have been removed as the user is greatly dehydrated.

Figure 22:
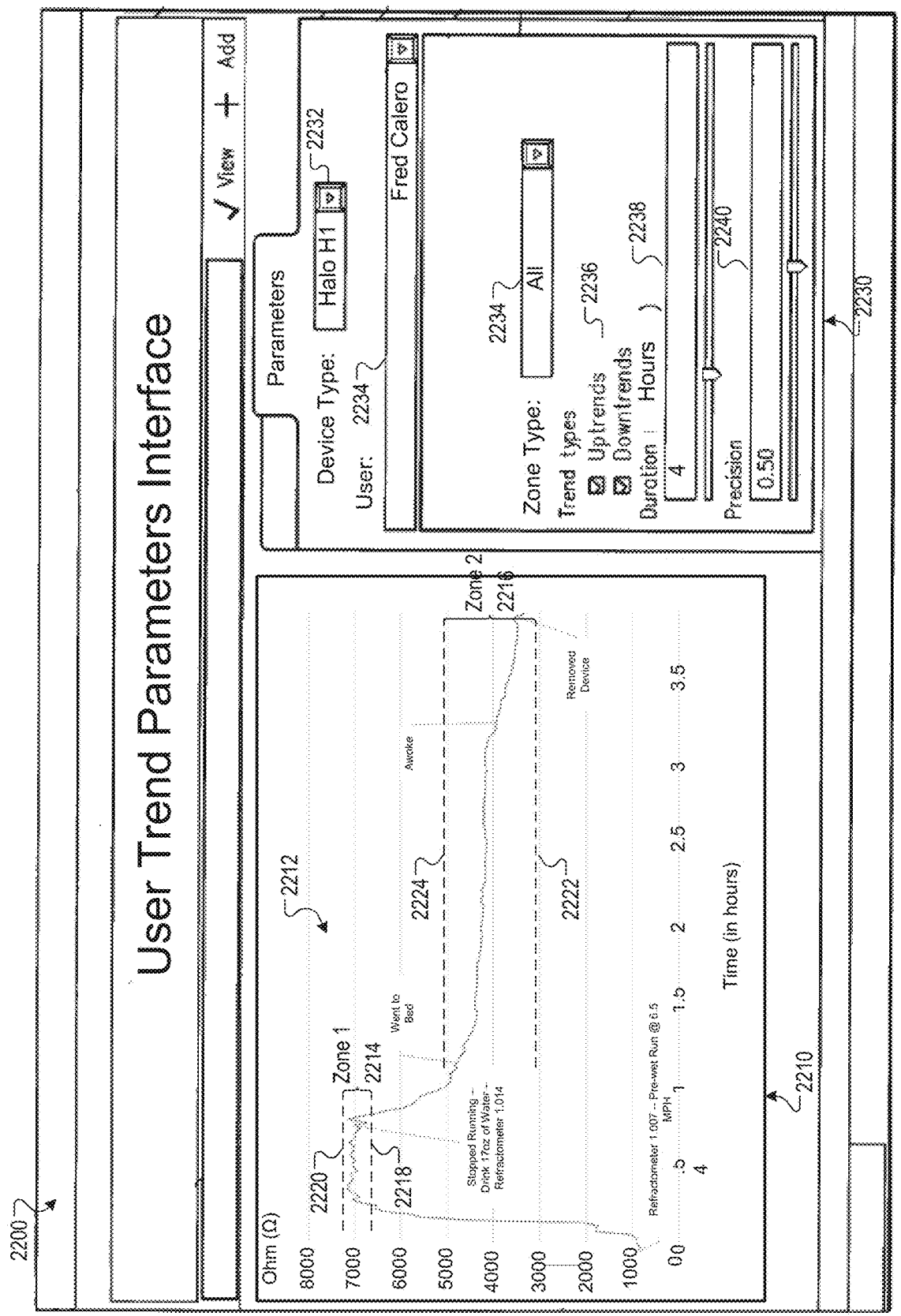
FIG. 22 illustrates a graphical user interface (GUI) to set trending parameters of trending data according to one embodiment.

FIG. 22 illustrates a graphical user interface (GUI) 2200 to set trending parameters of trending data according to one embodiment. The GUI 2200 can display a trend graph section 2210. The trend graph section 2210 can include a trend graph 2212 displaying a trending of measurement information. The trend graph 2212 can include trending zone 1 (2214) and trending zone 2 (2216) identifying different zones in the trending data of the trending graph 2212. For example, trending zone 1 (2214) can identify a high activity level zone and trending zone 2 (2216) can identify a low activity level zone. The trending zone 1 (2214) can include a lower boundary 2218 and an upper boundary 2220. The trending zone 2 (2216) can include a lower boundary 2222 and an upper boundary 2224. In one example, the electronic device can set the lower boundaries 2218 and 2222 and the upper boundaries 2220 and 2224 for the respective zones automatically (e.g., without user input) by identifying areas in the trend graph 2212 that are relatively flat or relatively sloped. In another example, the electronic device can receive boundary information from a user device (such as a mouse or keyboard) that manually sets the lower boundaries 2218 and 2222 and the upper boundaries 2220 and 2224. For example, the electronic device can receive, from an input device, adjustment information for the lower boundaries 2218 and 2222 and the upper boundaries 2220 and 2224. In one embodiment, the input device is a mouse, keyboard, trackpad, touch screen, and a user can use the input device to slide or move the lower boundary 2222 and the upper boundary 2224 in the trend graph section 2210 to set zone 1.

In one embodiment, GUI 2200 can also include a parameter setting section 2230 to adjust trending parameter settings of an electronic device. The parameter setting section 2230 can include: a device type window 2232 to select a type of device to be adjusted; a user window 2232 to select a user associated with the device to be adjusted; a zone type to be displayed for adjustment, such as all zones in the trending data; a trend type window 2236 to select types of trending data to be displayed for adjustment; a duration window 2238 to select a duration of the trend graph 2212 to display; and a precision window or sensitivity window 2240 to set a sensitivity level of the electronic device. In one embodiment, the sensitivity level setting can determine how large trending zone 1 (2214) or trending zone 2 (2216) may be. For example, zone 1 (2214) can be set to have a max range of 1000 Ωs. In another example, zone 2 (2216) can be set to have a max range of 2000 Ωs. In another example, the sensitivity level setting can determine an amount the trending data can deviate from the boundaries 2218 and 2220 or the boundaries 2222 and 2224 before the trending data is no longer in the respective zones.

The trend information can involve multiple levels of concern. One level could be related to the resident evaluating their behaviors. A second level could relate to a pending critical condition that needs emergency response. Trend information can be presented on a display. A user who might be viewing trend information on the display can interact with trending information via a touch screen or keyboard. Processing logic can also incorporate multi-level access control software that can make available to third parties, such as a medical resident, emergency personnel, caregivers, relatives or medical monitors.

The trend information can be stored over a period of time and can be used to establish baselines for the user. For example, when the trending data indicates a repetitive range or pattern in the data, the processing logic can set a baseline using the repetitive range or pattern in the data.

Figure 23:
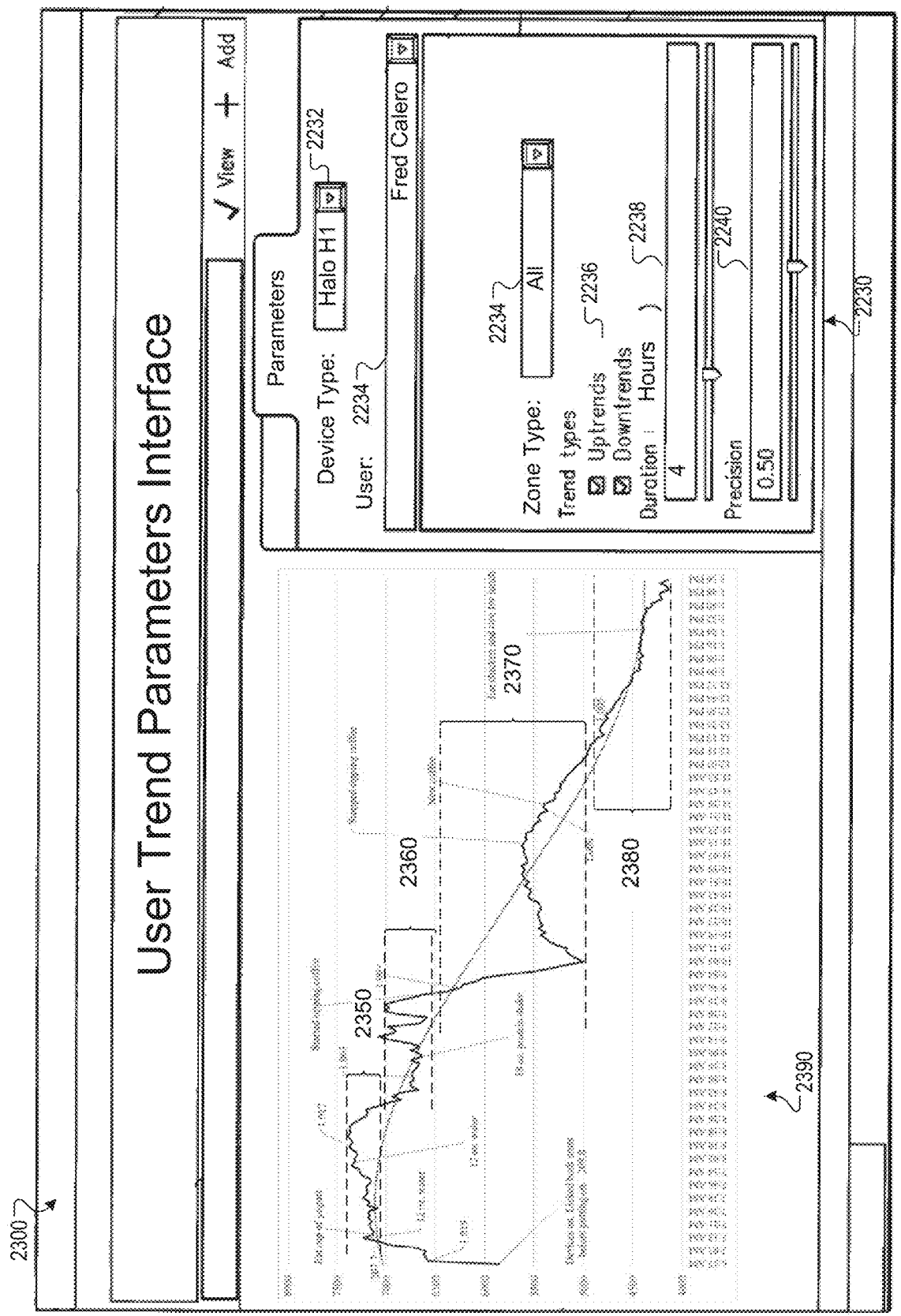
FIG. 23 illustrates a GUI to set trending parameters of trending data for a trending graph according to one embodiment.

FIG. 23 illustrates a graphical user interface (GUI) 2300 to set trending parameters of trending data for a trending graph 2390 according to one embodiment. The trend graph 2390 can include trending zone 1 (2350), trending zone 2 (2360), trending zone 3 (2370), and trending zone 4 (2380) where each zone 1-4 identifies different zones in the trending data of the trending graph 2390. The trend graph 2390 can be a low activity level graph. The remainder of the GUI 2300 is the same as the GUI 2200 (FIG. 22) as indicated by the same reference numbers.

Figure 24:
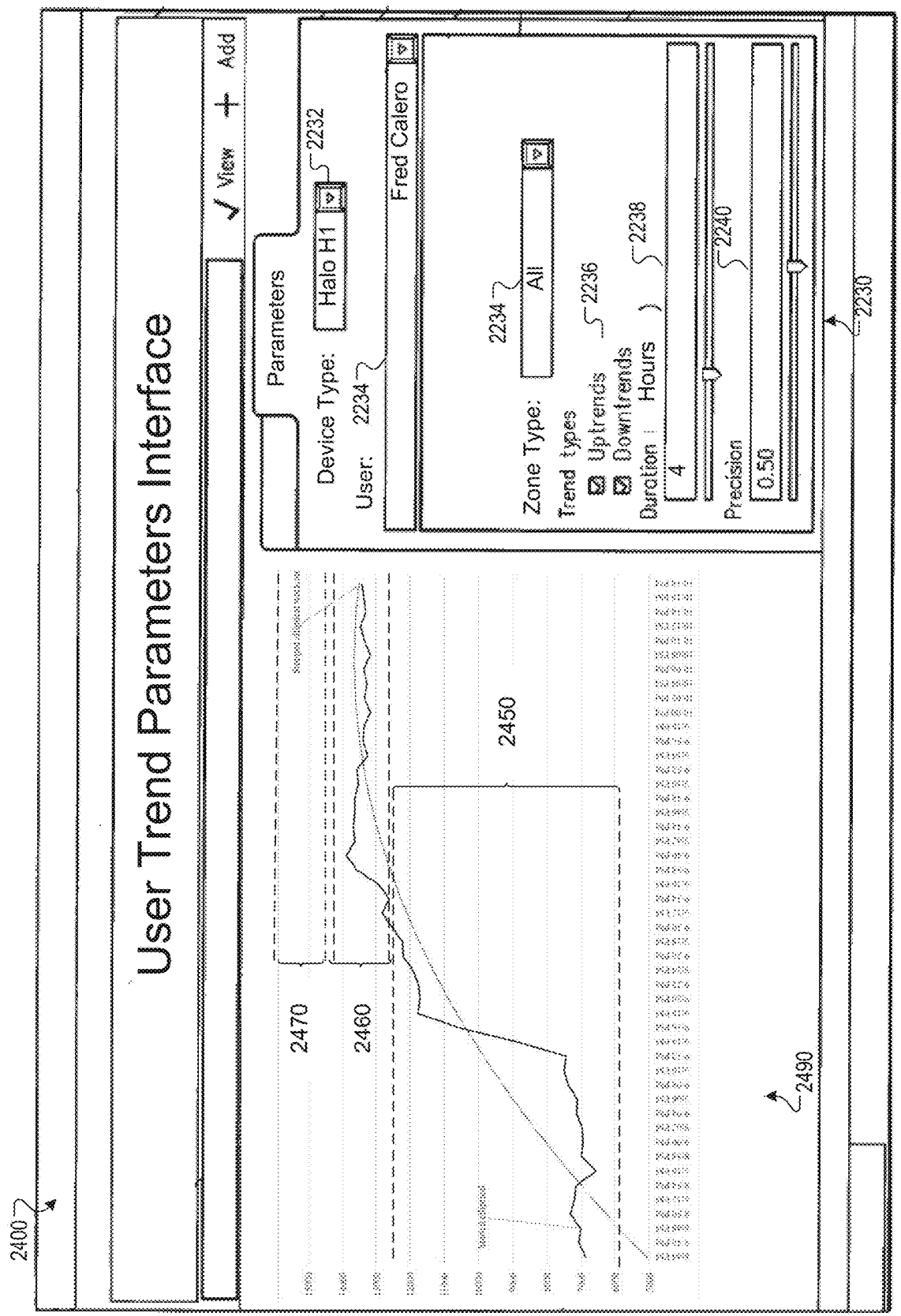
FIG. 24 illustrates a GUI to set trending parameters of trending data for a trending graph according to one embodiment.

FIG. 24 illustrates a graphical user interface (GUI) 2400 to set trending parameters of trending data for a trending graph 2490 according to one embodiment. The trend graph 2490 can include trending zone 1 (2450), trending zone 2 (2460), and trending zone 3 (2470), where each zone 1-3 identifies different zones in the trending data of the trending graph 2490. The trend graph 2490 can be a high activity level graph. The remainder of the GUI 2400 is the same as the GUI 2200 (FIG. 22) as indicated by the same reference numbers.

Figure 25:
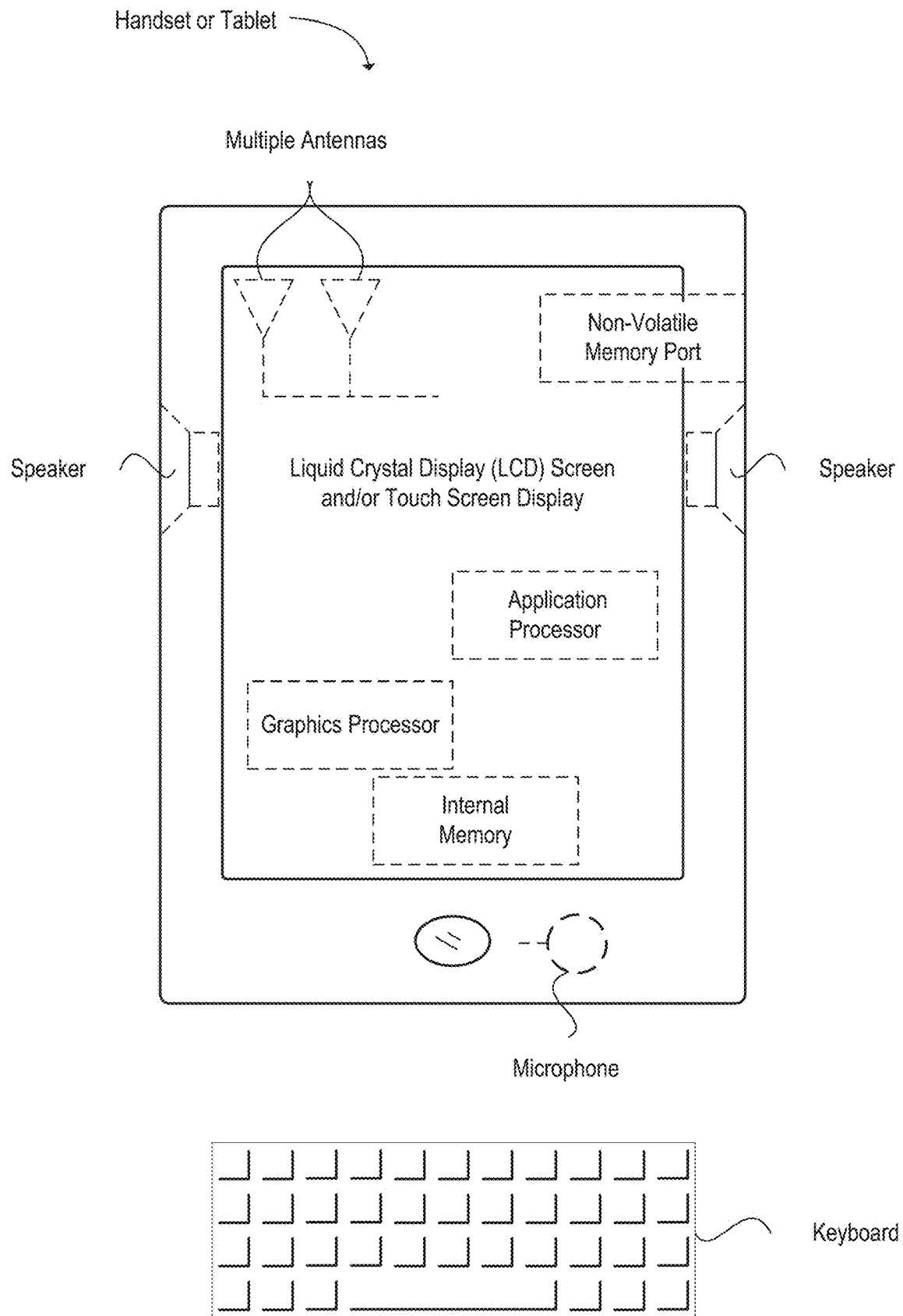
FIG. 25 provides an example illustration of a processing device disclosed herein, such as a user equipment (UE), a base station, an electronic device (UMD), a mobile wireless device, a mobile communication device, a tablet, a handset, or other type of wireless device according to one embodiment.
Figure 26:
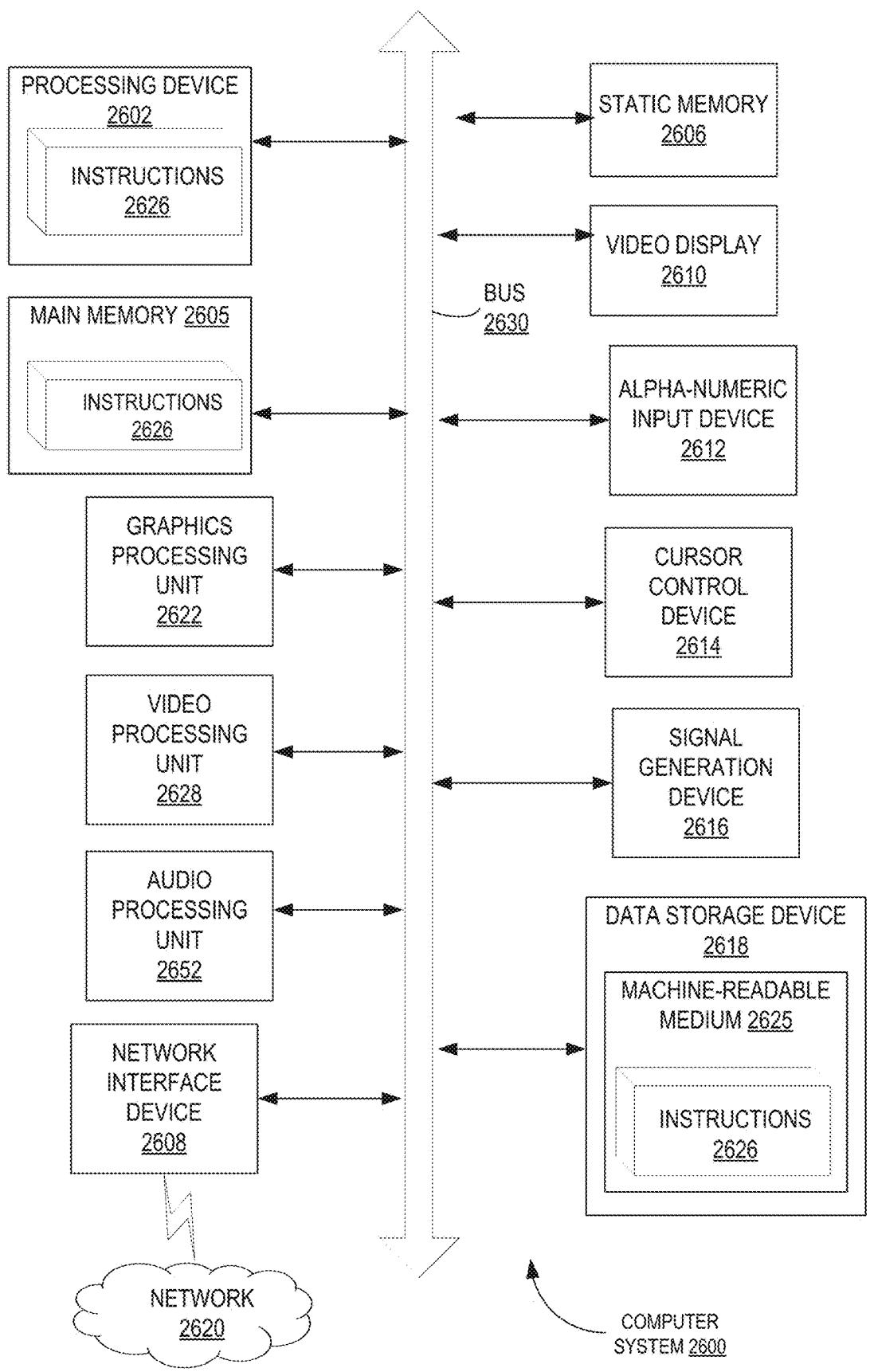
FIG. 26 illustrates a diagrammatic representation of a machine in the example form of a computer system within which a set of instructions, for causing the machine to perform any one or more of the methodologies discussed herein, may be executed.

FIG. 25 provides an example illustration of a processing device disclosed herein, such as a user equipment (UE), a base station, an electronic device (UMD), a mobile wireless device, a mobile communication device, a tablet, a handset, or other type of wireless device according to one embodiment. The device may include one or more antennas configured to communicate with a node or transmission station, such as a base station (BS), an evolved Node B (eNode B), a baseband unit (BBU), a remote radio head (RRH), a remote radio equipment (RRE), a relay station (RS), a radio equipment (RE), a remote radio unit (RRU), a central processing module (CPM), or other type of wireless wide area network (WWAN) access point. The device may be configured to communicate using at least one wireless communication standard including 3GPP LTE, WiMAX, High-Speed Packet Access (HSPA), Bluetooth, and Wi-Fi. The device may communicate using separate antennas for each wireless communication standard or shared antennas for multiple wireless communication standards. The device may communicate in a wireless local area network (WLAN), a wireless personal area network (WPAN), and/or a WWAN.

FIG. 25 also provides an illustration of a microphone and one or more speakers that may be used for audio input and output from the device. The display screen may be a liquid crystal display (LCD) screen, or other type of display screen such as an organic light emitting diode (OLED) display. The display screen may be configured as a touch screen. The touch screen may use capacitive, resistive, or another type of touch screen technology. An application processor and a graphics processor may be coupled to the internal memory to provide processing and display capabilities. A non-volatile memory port may also be used to provide data input/output options to a user. The non-volatile memory port may also be used to expand the memory capabilities of the wireless device. A keyboard may be integrated with the wireless device or wirelessly connected to the wireless device to provide additional user input. A virtual keyboard may also be provided using the touch screen.

Various techniques, or certain aspects or portions thereof, may take the form of program code (i.e., instructions) embodied in tangible media, such as floppy diskettes, CD-ROMs, hard drives, non-transitory computer readable storage medium, or any other machine-readable storage medium wherein, when the program code is loaded into and executed by a machine, such as a computer, the machine becomes an apparatus for practicing the various techniques. In the case of program code execution on programmable computers, the computing device may include a processor, a storage medium readable by the processor (including volatile and non-volatile memory and/or storage elements), at least one input device, and at least one output device. The volatile and non-volatile memory and/or storage elements may be a random access memory (RAM), electrically erasable programmable read-only memory (EEPROM), flash drive or flash memory, optical drive, magnetic hard drive, or other medium for storing electronic data. The base station and mobile station may also include a transceiver module, a counter module, a processing module, and/or a clock module or timer module. One or more programs that may implement or utilize the various techniques described herein may use an application programming interface (API), reusable controls, and the like. Such programs may be implemented in a high-level procedural or object-oriented programming language to communicate with a computer system. However, the program(s) may be implemented in assembly or machine language, if desired. In any case, the language may be a compiled or interpreted language, and combined with hardware implementations.

It should be understood that many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions, which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. The modules may be passive or active, including agents operable to perform desired functions.

Reference throughout this specification to "an example" means that a particular feature, structure, or characteristic described in connection with the example is included in at least one embodiment of the present invention. Thus, appearances of the phrases "in an example" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the foregoing description, numerous specific details are provided, such as examples of layouts, distances, network examples, etc., to provide a thorough understanding of embodiments of the invention. One skilled in the relevant art will recognize, however, that the invention may be practiced without one or more of the specific details, or with other methods, components, layouts, etc. In other instances, well-known structures, materials, or operations are not shown or described in detail to avoid obscuring aspects of the invention.

While the foregoing examples are illustrative of the principles of the present invention in one or more particular applications, it will be apparent to those of ordinary skill in the art that numerous modifications in form, usage and details of implementation may be made without the exercise of inventive faculty, and without departing from the principles and concepts of the invention. Accordingly, it is not intended that the invention be limited, except as by the claims set forth below.

Turning to FIG. 23 a block diagram of an exemplary computer system formed with a processor that includes execution units to execute an instruction, where one or more of the interconnects implement one or more features in accordance with one example implementation of the present disclosure is illustrated. System 2300 includes a component, such as a processor 2302 to employ execution units including logic to perform algorithms for process data, in accordance with the present disclosure, such as in the example implementation described herein. System 2300 is representative of processing systems based on the PENTIUM III™, PENTIUM 4™, Xeon™, Itanium, XScale™ and/or StrongARM™ microprocessors available from Intel Corporation of Santa Clara, Calif., although other systems (including PCs having other microprocessors, engineering workstations, set-top boxes and the like) may also be used. In one example implementation, sample system 2300 executes a version of the WINDOWS™ operating system available from Microsoft Corporation of Redmond, Wash., although other operating systems (UNIX and Linux for example), embedded software, and/or graphical user interfaces, may also be used. Thus, example implementations of the present disclosure are not limited to any specific combination of hardware circuitry and software.

Example implementations are not limited to computer systems. Alternative example implementations of the present disclosure can be used in other devices such as handheld devices and embedded applications. Some examples of handheld devices include cellular phones, Internet Protocol devices, digital cameras, personal digital assistants (PDAs), and handheld PCs. Embedded applications can include a microcontroller, a digital signal processor (DSP), system on a chip, network computers (NetPC), set-top boxes, network hubs, wide area network (WAN) switches, or any other system that can perform one or more instructions in accordance with at least one example implementation.

Alternative example implementations of the present disclosure can be used in other devices, such as an electronic device. The electronic device may be connected (e.g., networked) to other machines in a LAN, an intranet, an extranet, or the Internet. The electronic device may operate in the capacity of a server or a client device in a client-server network environment, or as a peer device in a peer-to-peer (or distributed) network environment. The electronic device may be a personal computer (PC), a tablet PC, a set-top box (STB), a cellular telephone, a smartphone, a web appliance, a server, a network router, switch or bridge, or any electronic device capable of executing a set of instructions (sequential or otherwise) that specify actions to be taken by that electronic device. Further, while only a single electronic device is illustrated, the term "electronic device" shall also be taken to include any collection of electronic devices that individually or jointly execute a set (or multiple sets) of instructions to perform any one or more of the methodologies discussed herein.

The system 2600 may correspond to the electronic device 110 (FIG. 1), the electronic device 220 (FIG. 2), the electronic device 410 (FIG. 4), the electronic device 510 (FIG. 5), the electronic device 610 (FIG. 6), the electronic device 710 (FIG. 7), the electronic device 910 (FIG. 9), or the electronic device 1010 (FIG. 10). The system 2600 may correspond to at least a portion of a cloud-based computer system.

In this illustrated example implementation, processor 2602 includes one or more execution units 2608 to implement an algorithm that is to perform at least one instruction. One example implementation may be described in the context of a single processor desktop or server system, but alternative example implementations may be included in a multiprocessor system. System 2600 is an example of a 'hub' system architecture. The computer system 2600 includes a processor 2602 to process data signals. The processor 2602, as one illustrative example, includes a complex instruction set computer (CISC) microprocessor, a reduced instruction set computing (RISC) microprocessor, a very long instruction word (VLIW) microprocessor, a processor implementing a combination of instruction sets, or any other processor device, such as a digital signal processor, for example. The processor 2602 is coupled to a processor bus 2610 that transmits data signals between the processor 2602 and other components in the system 2600. The elements of system 2600 (e.g. graphics accelerator 2612, memory controller hub 2616, memory 2620, I/O controller hub 2624, wireless transceiver 2626, Flash BIOS 2628, Network controller 2634, Audio controller 2636, Serial expansion port 2638, I/O controller 2640, etc.) perform their conventional functions that are well known to those familiar with the art.

In one example implementation, the processor 2602 includes a Level 1 (L1) internal cache memory 2604. Depending on the architecture, the processor 2602 may have a single internal cache or multiple levels of internal caches. Other example implementations include a combination of both internal and external caches depending on the particular implementation and needs. Register file 2606 is to store different types of data in various registers including integer registers, floating point registers, vector registers, banked registers, shadow registers, checkpoint registers, status registers, and instruction pointer register.

Execution unit 2608, including logic to perform integer and floating point operations, also resides in the processor 2602. The processor 2602, in one example implementation, includes a microcode (ucode) ROM to store microcode, which when executed, is to perform algorithms for certain macroinstructions or handle complex scenarios. Here, microcode is potentially updateable to handle logic bugs/fixes for processor 2602. For one example implementation, execution unit 2608 includes logic to handle a packed instruction set 2609. By including the packed instruction set 2609 in the instruction set of a general-purpose processor 2602, along with associated circuitry to execute the instructions, the operations used by many multimedia applications may be performed using packed data in a general-purpose processor 2602. Thus, many multimedia applications are accelerated and executed more efficiently by using the full width of a processor's data bus for performing operations on packed data. This potentially eliminates the need to transfer smaller units of data across the processor's data bus to perform one or more operations, one data element at a time.

Alternate example implementations of an execution unit 2608 may also be used in microcontrollers, embedded processors, graphics devices, DSPs, and other types of logic circuits. System 2600 includes a memory 2620. Memory 2620 includes a dynamic random access memory (DRAM) device, a static random access memory (SRAM) device, flash memory device, or other memory device. Memory 2620 stores instructions and/or data represented by data signals that are to be executed by the processor 2602.

A system logic chip 2616 is coupled to the processor bus 2610 and memory 2620. The system logic chip 2616 in the illustrated example implementation is a memory controller hub (MCH). The processor 2602 can communicate to the MCH 2616 via a processor bus 2610. The MCH 2616 provides a high bandwidth memory path 2618 to memory 2620 for instruction and data storage and for storage of graphics commands, data and textures. The MCH 2616 is to direct data signals between the processor 2602, memory 2620, and other components in the system 2600 and to bridge the data signals between processor bus 2610, memory 2620, and system I/O 2622. In some example implementations, the system logic chip 2616 can provide a graphics port for coupling to a graphics controller 2612. The MCH 2616 is coupled to memory 2620 through a memory interface 2618. The graphics card 2612 is coupled to the MCH 2616 through an Accelerated Graphics Port (AGP) interconnect 2614.

System 2600 uses a proprietary hub interface bus 2622 to couple the MCH 2616 to the I/O controller hub (ICH) 2630. The ICH 2630 provides direct connections to some I/O devices via a local I/O bus. The local I/O bus is a high-speed I/O bus for connecting peripherals to the memory 2620, chipset, and processor 2602. Some examples are the audio controller, firmware hub (flash BIOS) 2628, wireless transceiver 2626, data storage 2624, legacy I/O controller containing user input and keyboard interfaces, a serial expansion port such as Universal Serial Bus (USB), and a network controller 2634. The data storage device 2624 can comprise a hard disk drive, a floppy disk drive, a CD-ROM device, a flash memory device, or other mass storage device.

For another example implementation of a system, an instruction in accordance with one example implementation can be used with a system on a chip. One example implementation of a system on a chip comprises a processor and a memory. The memory for one such system is a flash memory. The flash memory can be located on the same die as the processor and other system components. Additionally, other logic blocks such as a memory controller or graphics controller can also be located on a system on a chip.

In the following description, numerous specific details are set forth, such as examples of specific types of processors and system configurations, specific hardware structures, specific architectural and microarchitectural details, specific register configurations, specific instruction types, specific system components, specific measurements/heights, specific processor pipeline stages and operation etc. in order to provide a thorough understanding of the present disclosure. It will be apparent, however, to one skilled in the art that these specific details need not be employed to practice the present disclosure. In other instances, well known components or methods, such as specific and alternative processor architectures, specific logic circuits/code for described algorithms, specific firmware code, specific interconnect operation, specific logic configurations, specific manufacturing techniques and materials, specific compiler implementations, specific expression of algorithms in code, specific power down and gating techniques/logic and other specific operational details of computer system haven't been described in detail in order to avoid unnecessarily obscuring the present disclosure.

Although the following example implementations may be described with reference to energy conservation and energy efficiency in specific integrated circuits, such as in computing platforms or microprocessors, other example implementations are applicable to other types of integrated circuits and logic devices. Similar techniques and teachings of example implementations described herein may be applied to other types of circuits or semiconductor devices that may also benefit from better energy efficiency and energy conservation. For example, the disclosed example implementations are not limited to desktop computer systems or Ultrabooks™. And may be also used in other devices, such as handheld devices, tablets, other thin notebooks, systems on a chip (SOC) devices, and embedded applications. Some examples of handheld devices include cellular phones, Internet protocol devices, digital cameras, personal digital assistants (PDAs), and handheld PCs. Embedded applications typically include a microcontroller, a digital signal processor (DSP), a system on a chip, network computers (NetPC), set-top boxes, network hubs, wide area network (WAN) switches, or any other system that can perform the functions and operations taught below. Moreover, the apparatus', methods, and systems described herein are not limited to physical computing devices, but may also relate to software optimizations for energy conservation and efficiency. As will become readily apparent in the description below, the example implementations of methods, apparatus', and systems described herein (whether in reference to hardware, firmware, software, or a combination thereof) are vital to a 'green technology' future balanced with performance considerations.

It is described that the system may be any kind of computer or embedded system. The disclosed embodiments may especially be used for electronic devices, electronic implants, sensory and control infrastructure devices, controllers, supervisory control and data acquisition (SCADA) systems, or the like. Moreover, the apparatuses, methods, and systems described herein are not limited to physical computing devices, but may also relate to software optimizations for energy conservation and efficiency. As will become readily apparent in the description below, the embodiments of methods, apparatuses, and systems described herein (whether in reference to hardware, firmware, software, or a combination thereof).

Although the following example implementations are described with reference to a processor, other example implementations are applicable to other types of integrated circuits and logic devices. Similar techniques and teachings of example implementations of the present disclosure can be applied to other types of circuits or semiconductor devices that can benefit from higher pipeline throughput and improved performance. The teachings of example implementations of the present disclosure are applicable to any processor or machine that performs data manipulations. However, the present disclosure is not limited to processors or machines that perform 512-bit, 256-bit, 128-bit, 64-bit, 32-bit, or 16-bit data operations and can be applied to any processor and machine in which manipulation or management of data is performed. In addition, the following description provides examples, and the accompanying drawings show various examples for the purposes of illustration. However, these examples should not be construed in a limiting sense as they are merely intended to provide examples of example implementations of the present disclosure rather than to provide an exhaustive list of all possible implementations of example implementations of the present disclosure.

Although the below examples describe instruction handling and distribution in the context of execution units and logic circuits, other example implementations of the present disclosure can be accomplished by way of a data or instructions stored on a machine-readable, tangible medium, which when performed by a machine cause the machine to perform functions consistent with at least one example implementation of the present disclosure. In one example implementation, functions associated with example implementations of the present disclosure are embodied in machine-executable instructions. The instructions can be used to cause a general-purpose or special-purpose processor that is programmed with the instructions to perform the steps of the present disclosure. Example implementations of the present disclosure may be provided as a computer program product or software which may include a machine or computer-readable medium having stored thereon instructions which may be used to program a computer (or other electronic devices) to perform one or more operations according to example implementations of the present disclosure. Alternatively, steps of example implementations of the present disclosure might be performed by specific hardware components that contain fixed-function logic for performing the steps, or by any combination of programmed computer components and fixed-function hardware components.

Instructions used to program logic to perform example implementations of the present disclosure can be stored within a memory in the system, such as DRAM, cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, Compact Disc, Read-Only Memory (CD-ROMs), and magneto-optical disks, Read-Only Memory (ROMs), Random Access Memory (RAM), Erasable Programmable Read-Only Memory (EPROM), Electrically Erasable Programmable Read-Only Memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the computer-readable medium includes any type of tangible machine-readable medium suitable for storing or transmitting electronic instructions or information in a form readable by a machine (e.g., a computer).

The embodiments of methods, hardware, software, firmware or code set forth above may be implemented via instructions or code stored on a machine-accessible, machine readable, computer accessible, or computer readable medium which are executable by a processing element. A non-transitory machine-accessible/readable medium includes any mechanism that provides (i.e., stores and/or transmits) information in a form readable by a machine, such as a computer or electronic system. For example, a non-transitory machine-accessible medium includes random-access memory (RAM), such as static RAM (SRAM) or dynamic RAM (DRAM); ROM; magnetic or optical storage medium; flash memory devices; electrical storage devices; optical storage devices; acoustical storage devices; other form of storage devices for holding information received from transitory (propagated) signals (e.g., carrier waves, infrared signals, digital signals); etc., which are to be distinguished from the non-transitory mediums that may receive information therefrom.

Instructions used to program logic to perform embodiments of the invention may be stored within a memory in the system, such as DRAM, cache, flash memory, or other storage. Furthermore, the instructions may be distributed via a network or by way of other computer readable media. Thus a machine-readable medium may include any mechanism for storing or transmitting information in a form readable by a machine (e.g., a computer), but is not limited to, floppy diskettes, optical disks, Compact Disc, Read-Only Memory (CD-ROMs), and magneto-optical disks, Read-Only Memory (ROMs), Random Access Memory (RAM), Erasable Programmable Read-Only Memory (EPROM), Electrically Erasable Programmable Read-Only Memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the computer-readable medium includes any type of tangible machine-readable medium suitable for storing or transmitting electronic instructions or information in a form readable by a machine (e.g., a computer)

The computer-readable storage medium may also be used to store instructions utilizing logic and/or a software library containing methods that call the above applications. While the computer-readable storage medium can be a single medium, the term "computer-readable storage medium" should be taken to include a single medium or multiple media (e.g., a centralized or distributed database, and/or associated caches and servers) that store the one or more sets of instructions. The term "computer-readable storage medium" shall accordingly be taken to include, but not be limited to, solid-state memories, optical media, and magnetic media.

A design may go through various stages, from creation to simulation to fabrication. Data representing a design may represent the design in a number of manners. First, as is useful in simulations, the hardware may be represented using a hardware description language or another functional description language. Additionally, a circuit level model with logic and/or transistor gates may be produced at some stages of the design process. Furthermore, most designs, at some stage, reach a level of data representing the physical placement of various devices in the hardware model. In the case where conventional semiconductor fabrication techniques are used, the data representing the hardware model may be the data specifying the presence or absence of various features on different mask layers for masks used to produce the integrated circuit. In any representation of the design, the data may be stored in any form of a machine-readable medium. A memory or a magnetic or optical storage such as a disc may be the machine readable medium to store information transmitted via optical or electrical wave modulated or otherwise generated to transmit such information. When an electrical carrier wave indicating or carrying the code or design is transmitted, to the extent that copying, buffering, or re-transmission of the electrical signal is performed, a new copy is made. Thus, a communication provider or a network provider may store on a tangible, machine-readable medium, at least temporarily, an article, such as information encoded into a carrier wave, embodying techniques of example implementations of the present disclosure.

In modern processors, a number of different execution units are used to process and execute a variety of code and instructions. Not all instructions are created equal as some are quicker to complete while others can take a number of clock cycles to complete. The faster the throughput of instructions, the better the overall performance of the processor. Thus it would be advantageous to have as many instructions execute as fast as possible. However, there are certain instructions that have greater complexity and require more in terms of execution time and processor resources. For example, there are floating point instructions, load/store operations, data moves, etc.

As more computer systems are used in internet, text, and multimedia applications, additional processor support has been introduced over time. In one example implementation, an instruction set may be associated with one or more computer architectures, including data types, instructions, register architecture, addressing modes, memory architecture, interrupt and exception handling, and external input and output (I/O).

In one example implementation, the instruction set architecture (ISA) may be implemented by one or more micro-architectures, which includes processor logic and circuits used to implement one or more instruction sets. Accordingly, processors with different micro-architectures can share at least a portion of a common instruction set. For example, Intel® Pentium 4 processors, Intel® Core™ processors, and processors from Advanced Micro Devices, Inc. of Sunnyvale Calif. implement nearly identical versions of the x86 instruction set (with some extensions that have been added with newer versions), but have different internal designs. Similarly, processors designed by other processor development companies, such as ARM Holdings, Ltd., MIPS, or their licensees or adopters, may share at least a portion a common instruction set, but may include different processor designs. For example, the same register architecture of the ISA may be implemented in different ways in different micro-architectures using new or well-known techniques, including dedicated physical registers, one or more dynamically allocated physical registers using a register renaming mechanism (e.g., the use of a Register Alias Table (RAT), a Reorder Buffer (ROB) and a retirement register file. In one example implementation, registers may include one or more registers, register architectures, register files, or other register sets that may or may not be addressable by a software programmer.

In one example implementation, an instruction may include one or more instruction formats. In one example implementation, an instruction format may indicate various fields (number of bits, location of bits, etc.) to specify, among other things, the operation to be performed and the operand(s) on which that operation is to be performed. Some instruction formats may be further broken defined by instruction templates (or subformats). For example, the instruction templates of a given instruction format may be defined to have different subsets of the instruction format's fields and/or defined to have a given field interpreted differently. In one example implementation, an instruction is expressed using an instruction format (and, if defined, in a given one of the instruction templates of that instruction format) and specifies or indicates the operation and the operands upon which the operation will operate.

Scientific, financial, auto-vectorized general purpose, RMS (recognition, mining, and synthesis), and visual and multimedia applications (e.g., 2D/3D graphics, image processing, video compression/decompression, voice recognition algorithms and audio manipulation) may require the same operation to be performed on a large number of data items. In one example implementation, Single Instruction Multiple Data (SIMD) refers to a type of instruction that causes a processor to perform an operation on multiple data elements. SIMD technology may be used in processors that can logically divide the bits in a register into a number of fixed-sized or variable-sized data elements, each of which represents a separate value. For example, in one example implementation, the bits in a 64-bit register may be organized as a source operand containing four separate 16-bit data elements, each of which represents a separate 16-bit value. This type of data may be referred to as 'packed' data type or 'vector' data type, and operands of this data type are referred to as packed data operands or vector operands. In one example implementation, a packed data item or vector may be a sequence of packed data elements stored within a single register, and a packed data operand or a vector operand may a source or destination operand of an SIMD instruction (or 'packed data instruction' or a 'vector instruction'). In one example implementation, a SIMD instruction specifies a single vector operation to be performed on two source vector operands to generate a destination vector operand (also referred to as a result vector operand) of the same or different size, with the same or different number of data elements, and in the same or different data element order.

SIMD technology, such as that employed by the Intel® Core™ processors having an instruction set including x86, MMX™, Streaming SIMD Extensions (SSE), SSE2, SSE3, SSE4.1, and SSE4.2 instructions, ARM processors, such as the ARM Cortex® family of processors having an instruction set including the Vector Floating Point (VFP) and/or NEON instructions, and MIPS processors, such as the Loongson family of processors developed by the Institute of Computing Technology (ICT) of the Chinese Academy of Sciences, has enabled a significant improvement in application performance (Core™ and MMX™ are registered trademarks or trademarks of Intel Corporation of Santa Clara, Calif.).

In one example implementation, destination and source registers/data are generic terms to represent the source and destination of the corresponding data or operation. In some example implementations, they may be implemented by registers, memory, or other storage areas having other names or functions than those depicted. For example, in one example implementation, "DEST1" may be a temporary storage register or other storage area, whereas "SRC1" and "SRC2" may be a first and second source storage register or other storage area, and so forth. In other example implementations, two or more of the SRC and DEST storage areas may correspond to different data storage elements within the same storage area (e.g., an SIMD register). In one example implementation, one of the source registers may also act as a destination register by, for example, writing back the result of an operation performed on the first and second source data to one of the two source registers serving as a destination registers.

A design may go through various stages, from creation to simulation to fabrication. Data representing a design may represent the design in a number of manners. First, as is useful in simulations, the hardware may be represented using a hardware description language or another functional description language. Additionally, a circuit level model with logic and/or transistor gates may be produced at some stages of the design process. Furthermore, most designs, at some stage, reach a level of data representing the physical placement of various devices in the hardware model. In the case where conventional semiconductor fabrication techniques are used, the data representing the hardware model may be the data specifying the presence or absence of various features on different mask layers for masks used to produce the integrated circuit. In any representation of the design, the data may be stored in any form of a machine-readable medium. A memory or a magnetic or optical storage such as a disc may be the machine readable medium to store information transmitted via optical or electrical wave modulated or otherwise generated to transmit such information. When an electrical carrier wave indicating or carrying the code or design is transmitted, to the extent that copying, buffering, or re-transmission of the electrical signal is performed, a new copy is made. Thus, a communication provider or a network provider may store on a tangible, machine-readable medium, at least temporarily, an article, such as information encoded into a carrier wave, embodying techniques of embodiments of the present invention.

A module as used herein refers to any combination of hardware, software, and/or firmware. As an example, a module includes hardware, such as a microcontroller, associated with a non-transitory medium to store code adapted to be executed by the micro-controller. Therefore, in reference to a module, in one embodiment, refers to the hardware, which is specifically configured to recognize and/or execute the code to be held in a non-transitory medium. Furthermore, in another embodiment, use of a module refers to the non-transitory medium including the code, which is specifically adapted to be executed by the microcontroller to perform predetermined operations. And as may be inferred, in yet another embodiment, the term module (in this example) may refer to the combination of the microcontroller and the non-transitory medium. Often module boundaries that are illustrated as separate commonly vary and potentially overlap. For example, a first and a second module may share hardware, software, firmware, or a combination thereof, while potentially retaining some independent hardware, software, or firmware. In one embodiment, use of the term logic includes hardware, such as transistors, registers, or other hardware, such as programmable logic devices.

Use of the phrase 'configured to,' in one embodiment, refers to arranging, putting together, manufacturing, offering to sell, importing and/or designing an apparatus, hardware, logic, or element to perform a designated or determined task. In this example, an apparatus or element thereof that is not operating is still 'configured to' perform a designated task if it is designed, coupled, and/or interconnected to perform said designated task. As a purely illustrative example, a logic gate may provide a 0 or a 1 during operation. But a logic gate 'configured to' provide an enable signal to a clock does not include every potential logic gate that may provide a 1 or 0. Instead, the logic gate is one coupled in some manner that during operation the 1 or 0 output is to enable the clock. Note once again that use of the term 'configured to' does not require operation, but instead focus on the latent state of an apparatus, hardware, and/or element, wherein the latent state the apparatus, hardware, and/or element is designed to perform a particular task when the apparatus, hardware, and/or element is operating.

Furthermore, use of the phrases 'to,' capable of/to,' and or 'operable to,' in one embodiment, refers to some apparatus, logic, hardware, and/or element designed in such a way to enable use of the apparatus, logic, hardware, and/or element in a specified manner Note as above that use of to, capable to, or operable to, in one embodiment, refers to the latent state of an apparatus, logic, hardware, and/or element, where the apparatus, logic, hardware, and/or element is not operating but is designed in such a manner to enable use of an apparatus in a specified manner.

A value, as used herein, includes any known representation of a number, a state, a logical state, or a binary logical state. Often, the use of logic levels, logic values, or logical values is also referred to as 1's and 0's, which simply represents binary logic states. For example, a 1 refers to a high logic level and 0 refers to a low logic level. In one embodiment, a storage cell, such as a transistor or flash cell, may be capable of holding a single logical value or multiple logical values. However, other representations of values in computer systems have been used. For example, the decimal number ten may also be represented as a binary value of 1010 and a hexadecimal letter A. Therefore, a value includes any representation of information capable of being held in a computer system.

Moreover, states may be represented by values or portions of values. As an example, a first value, such as a logical one, may represent a default or initial state, while a second value, such as a logical zero, may represent a non-default state. In addition, the terms reset and set, in one embodiment, refer to a default and an updated value or state, respectively. For example, a default value potentially includes a high logical value, i.e. reset, while an updated value potentially includes a low logical value, i.e. set. Note that any combination of values may be utilized to represent any number of states.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In the foregoing specification, a detailed description has been given with reference to specific exemplary embodiments. It will, however, be evident that various modifications and changes may be made thereto without departing from the broader spirit and scope of the invention as set forth in the appended claims. The specification and drawings are, accordingly, to be regarded in an illustrative sense rather than a restrictive sense. Furthermore, the foregoing use of embodiment and other exemplary language does not necessarily refer to the same embodiment or the same example, but may refer to different and distinct embodiments, as well as potentially the same embodiment.

Some portions of the detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared and otherwise manipulated. It has proven convenient at times, principally for reasons of common usage, to refer to these signals as bits, values, elements, symbols, characters, terms, numbers or the like. The blocks described herein may be hardware, software, firmware or a combination thereof.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "defining," "receiving," "determining," "issuing," "linking," "associating," "obtaining," "authenticating," "prohibiting," "executing," "requesting," "communicating," or the like, refer to the actions and processes of a computing system, or similar electronic computing device, that manipulates and transforms data represented as physical (e.g., electronic) quantities within the computing system's registers and memories into other data similarly represented as physical quantities within the computing system memories or registers or other such information storage, transmission or display devices.

The words "example" or "exemplary" are used herein to mean serving as an example, instance or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or." That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Also, the terms "first," "second," "third," "fourth," etc. as used herein are meant as labels to distinguish among different elements and may not necessarily have an ordinal meaning according to their numerical designation.

What is claimed is:

1. A method comprising:
   measuring, by a sensor, a physiological measurement of an individual to obtain trend data correlating to a hydration level of the individual;
   identifying, by a processing device coupled to the sensor, an acclimation period of the individual subsequent to the individual attaching a wearable device to a body part of the individual, wherein:
   the acclimation period is a physiological adjustment of the body part to the wearable device being attached to the body part of the individual, wherein the acclimation period comprises:
      a first conductance between a first impedance pad and a second impedance pad of the wearable device based on a first distance between the body part and the first impedance pad; and
      a second conductance between the first impedance pad and the second impedance pad of the wearable device based on a second distance between the body part and the first impedance pad, wherein:
         the first distance is greater than the second distance; and
         the second conductance is greater than the first conductance; and
      the acclimation period is captured by the sensor during a first period of time during the physiological measurement;
   identifying, by the processing device, a first portion of the trend data that is within a variance range at a first measurement range, wherein:
      the first portion of the trend data is captured by the sensor during a second period of time during the physiological measurement; and
      the first portion of the trend data is indicative of a first activity level of the individual;
   identifying, by the processing device, a second portion of the trend data that exceeds the variance range at a second measurement range, wherein:
      the second portion of the trend data is captured by the sensor during a third period of time during the physiological measurement; and
      the second portion of the trend data is indicative of a second activity level of the individual, wherein the second activity level is different than the first activity level;
   identifying, by the processing device, a third portion of the trend data that is within the variance range at a third measurement range, wherein:
      the third portion of the trend data is captured by the sensor during a fourth period of time between the second period of time and the third period of time, wherein the fourth period of time separates the second period of time and the third period of time; and
      the third portion of the trend data is indicative of a physiological transition by a body of the individual from the first activity level to the second activity level;
   removing, by the processing device, the acclimation period of the trend data from the trend data;
   removing, by the processing device, the third portion of the trend data from the trend data;
   identifying, by the processing device, a trend parameter for at least one of the first portion of the trend data or the second portion of the trend data, the trend parameter indicating a transition of the hydration level of the individual from a first hydration level to a second hydration level; and
   providing a notification of the transition from the first hydration level to the second hydration level to the individual.

2. The method of claim 1, wherein the sensor comprises at least one of a pulse oximeter sensor, an electrocardiography (ECG) sensor, a fluid level sensor, an oxygen saturation sensor, a body temperature sensor, an ambient temperature sensor, a plethysmograph sensor, a respiration sensor, a breath sensor, a cardiac sensor, a heart rate sensor, an impedance sensor, an optical sensor, a spectrographic sensor, a humidity sensor, an altitude sensor, a barometer, a global positioning system (GPS) sensor, a triangulation sensor, a location sensor, a gyroscope sensor, a vibration sensor, an accelerometer sensor, a three-dimensional (3D) accelerometer sensor, a force sensor, a pedometer, a strain gauge, a magnetometer, or a geomagnetic field sensor.

3. The method of claim 1, wherein the physiological measurement comprises at least one of a hydration level measurement, a heart rate measurement, a blood pressure measurement, an oxygen level measurement, or a temperature measurement.

4. The method of claim 1, wherein the sensor comprises at least one of a physiological sensor, an environmental sensor, or a Newtonian sensor.

5. The method of claim 1, further comprising identifying a baseline variance range for the physiological measurement.

6. The method of claim 1, wherein the trend parameter is a coefficient of variation indicating an amount of variability relative to a reference value for the physiological measurement.

7. A wearable user measurement device (UMD) comprising:
  a sensor operable to measure a physiological measurement of an individual, wherein the sensor comprises a porous material facing a body part of the individual; and
  a processor operatively coupled to the sensor, wherein the processor is to:
    measure the physiological measurement of the individual with the sensor to obtain trend data correlating to a hydration level of the individual;
    identify an acclimation period of the individual subsequent to the individual attaching a wearable device to the body part of the individual, wherein the acclimation period is:
    a physiological adjust of the body part to the wearable device being attached to the body part of the individual, wherein the physical adjust comprises filling in gaps of the porous material of the sensor; and
    the acclimation period is during a first period of time during the physiological measurement;
    identify a first portion of the trend data that is within a variance range at a first measurement range, wherein:
      the first portion of the trend data is captured by the sensor during a second period of time during the physiological measurement; and
      the first portion of the trend data is indicative of a first activity level of the individual;
    identify a second portion of the trend data that exceeds the variance range at a second measurement range, wherein:
      the second portion of the trend data is captured by the during a third period of time time during the physiological measurement; and
      the second portion of the trend data is indicative of a second activity level of the individual, wherein the second activity level is different than the first activity level;
    identify a third portion of the trend data that is within the variance range at a third measurement range, wherein:
      the second portion of the trend data is captured by the sensor during a fourth period of time between the second period of time, wherein the fourth period of time separates the second period of time and the third period of time during the physiological measurement; and
      the second portion of the trend data is indicative of a physiological transition by a body of the individual from the first activity level to the second activity level;
    remove the acclimation period of the trend data from the trend data; and
    remove the second portion of the trend data from the trend data, wherein the second portion of the trend data is an acclimation phase of a body of the individual becoming acclimated to wearing the UMD.

8. The wearable UMD of claim 7, wherein the sensor comprises at least one of a pulse oximeter sensor, an electrocardiography (ECG) sensor, a fluid level sensor, an oxygen saturation sensor, a body temperature sensor, an ambient temperature sensor, a plethysmograph sensor, a respiration sensor, a breath sensor, a cardiac sensor, a heart rate sensor, an impedance sensor, an optical sensor, a spectrographic sensor, a humidity sensor, an altitude sensor, a barometer, a global positioning system (GPS) sensor, a triangulation sensor, a location sensor, a gyroscope sensor, a vibration sensor, an accelerometer sensor, a three-dimensional (3D) accelerometer sensor, a force sensor, a pedometer, a strain gauge, a magnetometer, or a geomagnetic field sensor.

9. The wearable UMD of claim 7, wherein the physiological measurement comprises at least one of a hydration level measurement, a heart rate measurement, a blood pressure measurement, an oxygen level measurement, or a temperature measurement.

10. The wearable UMD of claim 7, wherein the sensor comprises at least one of a physiological sensor, an environmental sensor, or a Newtonian sensor.

11. The wearable UMD of claim 7, wherein the processor is further to determine a baseline variance range for the individual.

12. The wearable UMD of claim 7, wherein the processor is further to identify a trend parameter for at least one of the first portion of the trend data or the third portion of the trend data, the trend parameter indicating a transition of the hydration level of the individual from a first hydration level to a second hydration level, wherein the trend parameter is a coefficient of variation indicating an amount of variability relative to a reference value.

13. An apparatus comprising:
  a sensor interface; and
  a processing element coupled to the sensor interface, wherein the processing element is operable to:
    measure a physiological measurement of an individual with a sensor to obtain trend data correlating to a hydration level of the individual;
    identify an acclimation period of the individual subsequent to the individual attaching a wearable device to a body part of the individual, wherein:
      the acclimation period is a physiological adjust of the body part to the wearable device being attached to the body part of the individual;
      the acclimation period is captured by the sensor during a first period of time;

the wearable device applies pressure to a surface of the body part engaged by the wearable device when the wearable device is attached to the body part; and the physiological adjust comprises the surface of the body part engaged by the wearable device compensating to the pressure applied to the surface of the body part by the wearable device;

identify a first portion of the trend data that is within a variance range at a first measurement range, wherein:
  the first portion of the trend data is captured by the sensor at a second point in time; and
  the first portion of the trend data is indicative of a first activity level of the individual;

identify a second portion of the trend data that exceeds the variance range at a second measurement range, wherein:
  the second portion of the trend data is captured by the sensor at a third period of time; and
  the second portion of the trend data is indicative of a second activity level of the individual, wherein the second activity level is different than the first activity level;

identify a third portion of the trend data that is within the variance range at a third measurement range, wherein:
  the third portion of the trend data is captured by the sensor at a fourth period of time between the second period of time and the third period of time; and
  the third portion of the trend data is indicative of a physiological transition by a body of the individual from the first activity level to the second activity level;

remove the acclimation period of the trend data from the trend data; and tag the second portion of the trend data in the trend data with a tag.

14. The apparatus of claim 13, wherein the physiological measurement comprises at least one of a hydration level measurement, a heart rate measurement, a blood pressure measurement, an oxygen level measurement, or a temperature measurement.

15. The apparatus of claim 13, wherein the sensor comprises at least one of a physiological sensor, an environmental sensor, and a Newtonian sensor.

16. The apparatus of claim 13, further comprising displaying a user interface wherein at least a portion of the user interface shows the first portion of the trend data, the second portion of the trend data with the tag, and the third portion of the trend data.

17. The apparatus of claim 13, wherein the variance range is a coefficient of variation indicating an amount of variability relative to a reference value.

18. The method of claim 1, wherein the second portion of the trend data is indicative of the body of individual adjusting to an environmental change or a physiological change.

19. The apparatus of claim 13, wherein the second portion of the trend data is indicative of the individual adjusting to an environmental change or a physiological change.

20. The method of claim 7, wherein the second portion of the trend data is indicative of the body of individual adjusting to an environmental change or a physiological change.

* * * * *